US012806285B2

(12) United States Patent
Kaushal

(10) Patent No.: US 12,806,285 B2
(45) Date of Patent: Nov. 24, 2026

(54) COMPOSITIONS FOR DELIVERY OF mRNA

(71) Applicant: TRANSLATE BIO, INC., Waltham, MA (US)

(72) Inventor: Neha Kaushal, Wellesley, MA (US)

(73) Assignee: TRANSLATE BIO, INC., Waltham, MA (US)

(*) Notice: Subject to any disclaimer, the term of this patent is extended or adjusted under 35 U.S.C. 154(b) by 343 days.

(21) Appl. No.: 18/575,019

(22) PCT Filed: Jun. 30, 2022

(86) PCT No.: PCT/US2022/035801
§ 371 (c)(1),
(2) Date: Dec. 28, 2023

(87) PCT Pub. No.: WO2023/278754
PCT Pub. Date: Jan. 5, 2023

(65) Prior Publication Data
US 2025/0001002 A1 Jan. 2, 2025

Related U.S. Application Data

(60) Provisional application No. 63/217,633, filed on Jul. 1, 2021.

(51) Int. Cl.
*A61K 48/00* (2006.01)
*A61K 47/54* (2017.01)
*A61K 47/60* (2017.01)
*A61K 47/69* (2017.01)
*C12N 15/88* (2006.01)

(52) U.S. Cl.
CPC ........ *A61K 48/0033* (2013.01); *A61K 47/545* (2017.08); *A61K 47/60* (2017.08); *A61K 47/6925* (2017.08); *C12N 15/88* (2013.01)

(58) Field of Classification Search
None
See application file for complete search history.

(56) References Cited

U.S. PATENT DOCUMENTS 4,897,355 A 1/1990 Eppstein et al.
5,171,678 A 12/1992 Behr et al.
5,334,761 A 8/1994 Gebeyehu et al.
8,278,036 B2 10/2012 Kariko et al.
2011/0038941 A1* 2/2011 Lee ........................ C12N 15/88 424/133.1
2012/0195936 A1 8/2012 Rudolph et al.
2015/0376115 A1 12/2015 Ansell et al.
2015/0376220 A1 12/2015 Derosa et al.
2016/0038432 A1 2/2016 Derosa et al.
2016/0040154 A1 2/2016 Heartlein et al.
2018/0153822 A1 6/2018 Karve et al.
2018/0251754 A1 9/2018 Derosa et al.
2018/0251755 A1 9/2018 Abysalh et al.
2018/0258423 A1 9/2018 Dias et al.
2018/0333457 A1* 11/2018 Heartlein ............... A61K 47/26
2019/0111074 A1* 4/2019 Lockhart ................. A61P 11/00
2020/0022921 A1* 1/2020 Karve .................. A61K 9/0073
2020/0197319 A1* 6/2020 Chen .................. A61K 49/1839

FOREIGN PATENT DOCUMENTS

WO 2005121348 A1 12/2005
WO 2009120247 A2 10/2009
WO 2010042877 A1 4/2010
WO 2010053572 A2 5/2010
WO 2010144740 A1 12/2010
WO 2011012316 A2 2/2011
WO 2012170889 A1 12/2012
WO 2013063468 A1 5/2013
WO 2013149140 A1 10/2013
WO 2015095340 A1 6/2015
WO 2015184256 A2 12/2015
WO 2015199952 A1 12/2015
WO 2016004202 A1 1/2016
WO 2016004318 A1 1/2016
WO 2016118724 A1 7/2016
WO 2016118725 A1 7/2016
WO 2016205691 A1 12/2016
WO 2017004143 A1 1/2017
WO 2017049245 A2 3/2017
WO 2017075531 A1 5/2017
WO 2017117528 A1 7/2017
WO 2017173054 A1 10/2017
WO 2018089790 A1 5/2018
WO 2018089801 A1 5/2018
WO 2018213476 A1 11/2018
WO 2020106946 A1 5/2020
WO 2020210901 A1 10/2020
WO 2020257716 A1 12/2020
(Continued)

OTHER PUBLICATIONS

National Human Genome Research Institute, Dec. 27, 2013 (https://www.genome.gov/Genetic-Disorders/Cystic-Fibrosis). (Year: 2013).*
Abysalh et al., "Methods and Composition for Messenger RNA Purification," U.S. Appl. No. 62/757,612, filed Nov. 8, 2018, 65 pages.
Abysalh et al., "Methods for Purification of Messenger RNA," U.S. Appl. No. 62/891,781, filed Aug. 26, 2019, 86 pages.
Athey et al., "A new and updated resource for codon usage tables," BMC Bioinformatics, vol. 18, No. 1, Article 391, Sep. 2, 2017, 10 pages.
Behr et al., "Efficient gene transfer into mammalian primary endocrine cells with lipopolyamine-coated DNA," Proceedings of the National Academy of Sciences USA, vol. 86, Sep. 1989, pp. 6982-6986.
Bloomfield, "Quasi-elastic light scattering applications in biochemistry and biology," Annual Review of Biophysics and Bioengineering, vol. 10, Jun. 1, 1981, pp. 421-450.
Clark, "The use of laser diffraction for the evaluation of the aerosol clouds generated by medical nebulizers," International Journal of Pharmaceutics, vol. 115, Issue 1, Feb. 28, 1995, pp. 69-78.
(Continued)

*Primary Examiner* — Celeste A Roney
(74) *Attorney, Agent, or Firm* — MH2 Technology Law Group, LLP

(57) ABSTRACT

The present invention provides, among other things, improved compositions comprising mRNA lipid nanoparticles and surfactants.

38 Claims, 4 Drawing Sheets

(56) References Cited

FOREIGN PATENT DOCUMENTS

WO 2021202694 A1 10/2021

OTHER PUBLICATIONS

Derosa et al., "Ribose Cationic Lipids," U.S. Appl. No. 62/672,194, filed May 16, 2018, 212 pages.
Derosa et al., "Encapsulation of Messenger RNA," U.S. Appl. No. 62/020,163, filed Jul. 2, 2014, 53 pages.
Felgner et al., "Lipofection: A highly efficient, lipid-mediated DNA-transfection procedure," Proceedings of the National Academy of Sciences USA, vol. 84, Nov. 1987, pp. 7413-7417.
Fulzele et al., Inhalation Delivery and Anti-tumor Activity of Celecoxib in Human Orthotopic Non-Small Cell Lung Cancer Xenograft Model, Pharm. Res. vol. 23, No. 9, Sep. 2006, pp. 2094-2106 (23 pages total).
Heyes et al., "Cationic lipid saturation influences intracellular delivery of encapsulated nucleic acids," Journal of Controlled Release, vol. 107, 2005 (Available online Jul. 28, 2005), pp. 276-287.
Karve et al., "Improve Compositions for Delivery of MRNA," U.S. Appl. No. 63/176,549, filed Apr. 19, 2021, 164 pages.
Lee, Sun Hwa (PCT Authorized Officer), International Preliminary Report on Patentability and Written Opinion of the International Searching Authority for International Application No. PCT/US2022/035801 dated Jan. 11, 2024, 9 pages.
McClellan et al., "Genetic Heterogeneity in Human Disease," Cell, vol. 141, Apr. 16, 2010, pp. 210-217.
Morrissey et al., "Potent and persistent in vivo anti-HBV activity of chemically modified siRNAs," Nature Biotechnology, vol. 23, No. 8, Aug. 2005 (Published Jul. 24, 2005), pp. 1002-1007.
Nakamura et al., "Codon usage tabulated from international DNA sequence databases: status for the year 2000," Nucleic Acids Research, vol. 28, No. 1, 2000, p. 292.
Semple et al., "Rational design of cationic lipids for siRNA delivery," Nature Biotechnology, vol. 28, No. 2, Feb. 2010 (Published online Jan. 17, 2010), pp. 172-176, XP002633693.
Sharp et al., "The codon adaptation index—a measure of directional synonymous codon usage bias, and its potential applications," Nucleic Acids Research, vol. 15, No. 3, 1987, pp. 1281-1295.
Valle et al., "Sildenafil Citrate Liposomes for Pulmonary Delivery by Ultrasonic Nebulization," Applied Sciences, vol. 8, Article 1291, Aug. 2, 2018, 14 pages.
Whitehead et al., "Degradable Lipid Nanoparticles with Predictable In Vivo siRNA Delivery Activity," Nature Communications, vol. 5, No. 4277, Jun. 27, 2014 (Available in PMC Dec. 27, 2014), 10 pages.
Zhang, Y., et al., "Cyclic Amino Acid Lipids," U.S. Appl. No. 62/758,179, filed Nov. 9, 2018, 157 pages.
European Communication pursuant to Rules 161(1) and 162 EPC for European Application No. 22747876.5 dated Feb. 9, 2024, 3 pages.
Christian Felder (Authorized Officer), International Search Report and Written Opinion dated Oct. 11, 2022 from International Application No. PCT/US2022/035801, 12 pages.
Nokhodchi et al. (eds.), "Pulmonary Drug Delivery—Advances and Challenges", 2015, Advances in Pharmaceutical Technology, John Wiley & Sons, Ltd., 383 pages.

* cited by examiner

D-α-Tocopherol PEG 1000 Succinate

COMPOSITIONS FOR DELIVERY OF mRNA

CROSS-REFERENCE TO RELATED APPLICATIONS

This application is a U.S. National Stage application of PCT/US2022/035801, filed on Jun. 30, 222, which claims priority to U.S. Provisional Patent Application Ser. No. 63/217,633, filed on Jul. 1, 2021, the entire disclosure of each application is incorporated by reference herein in its entirety for all purposes.

BACKGROUND

Messenger RNA therapy (MRT) is becoming an increasingly important approach for the treatment of a variety of diseases. MRT involves administration of messenger RNA (mRNA) to a patient in need of the therapy for production of the protein encoded by the mRNA within the patient's body.

Lipid nanoparticles are commonly used to encapsulate mRNA for efficient in vivo delivery of mRNA. To efficiently deliver lipid nanoparticles to the lungs of a subject they are typically nebulized. Lipid nanoparticle compositions that can be nebulized to deliver mRNA to the lungs are described, e.g., in WO 2020/106946, which is incorporated herein by reference.

D-α-tocopheryl polyethylene glycol 1000 succinate (TPGS, also known as vitamin E TPGS) is a water-soluble derivative of natural vitamin E. It has an amphiphilic structure comprising a hydrophilic polar head portion and a lipophilic alkyl tail. TPGS finds use as a solubilizer, emulsifier, as well as a permeation and bioavailability enhancer of hydrophobic drugs. For example, it has previously been used to solubilize corticosteroids in order to form stable micellar solutions that are suitable for administration by inhalation. In some instances, TPGS has also been incorporated into phosphatidylcholine-based liposomes for the delivery of small-molecule drug products.

SUMMARY OF THE INVENTION

The inventors surprisingly found that D-α-tocopheryl polyethylene glycol 1000 succinate (TPGS) can act as an excipient in compositions comprising lipid nanoparticles encapsulating mRNA to improve nebulization. Its surfactant properties and capability to effectively solubilize hydrophobic drugs make TPGS an unlikely choice as an excipient for lipid nanoparticles. For instance, other surfactants such as Tween 20, Tween 80, poloxamers (such as P188) or PEG 400 are also widely used to solubilize hydrophobic drugs, but were found to either be unsuitable for use as an excipient in lipid nanoparticle compositions (e.g., Tween 80, tween 20) or did not improve the nebulization properties of mRNA-lipid nanoparticle compositions (e.g., PEG 400). While not wishing to be bound by any particular theory, the inventors believe that TPGS and similar surfactants which consist of an antioxidant moiety covalently linked via a linker moiety to a PEG moiety provide a particular combination of properties that render them especially suitable as excipient to improve the nebulization output rate of mRNA-lipid nanoparticle compositions. Surprisingly, the inventors also found that the use of such surfactants does not result in an increase in size or a loss in encapsulation efficiency of the lipid nanoparticles upon nebulization.

Accordingly, the present invention provides, among other things, a composition comprising (a) an mRNA encapsulated in a lipid nanoparticle, and (b) one or more surfactants consisting of an antioxidant moiety covalently linked via a linker moiety to a PEG moiety, wherein the one or more surfactant(s) is/are present at a concentration of at least 0.1% weight to volume (w/v). Such composition are capable of being nebulized at a nebulization output rate of at least 10 ml/h. Moreover, nebulization does not result in a significant increase in size or loss encapsulation efficiency of the lipid nanoparticle. As a consequence, a composition in accordance with the invention is highly effective in delivering intact mRNA into the lung to induce expression of the mRNA-encoded protein.

In some embodiments, the PEG moiety in the one or more surfactants present in a composition of the invention is unmodified PEG, methoxy-PEG (mPEG) or carboxylic acid-functionalized PEG (COOH-PEG). In some embodiments, the PEG moiety has an average molecular weight between 1 kDa and 5 kDa, e.g. 1 KDa, 2 KDa, 3 KDa, 3.4 KDa or 5 KDa. In preferred embodiments, the PEG moiety has an average molecular weight of 0.5 kDa, 1 kDa, 1.5 kDa, 2 kDa, 2.5 kDa or 3 kDa. In some embodiments, the linker moiety is succinate, oxalate, adipate, malonate, fumarate, malate, glutarate or maleate. In particular embodiments, the linker moiety is succinate. In some embodiments, the antioxidant moiety is a lipophilic vitamin. In certain embodiments, the lipophilic vitamin is selected from vitamin A, D, E or K. In particular embodiments, the lipophilic vitamin is selected from vitamin E or D.

In some embodiments, the surfactant in a composition of the invention is selected from: D-α-tocopheryl polyethylene glycol 1000 succinate (TPGS); mPEG-2K-succinate-vitamin E; COOH-PEG-3.4 k-succinate-vitamin E; mPEG-2K-succinate-vitamin D; mPEG-2K-succinate-vitamin D; or COOH-PEG-3.4 k-succinate-vitamin D. In particular embodiments, the surfactant is TPGS.

In some embodiments, the one or more surfactants is present in a composition of the invention at a concentration of at least 0.2%, at least 0.5% or at least 1% w/v. In some embodiments, the one or more surfactants is present at a concentration of 0.1-5% w/v. In some embodiments, the one or more surfactants is present at a concentration of 0.1-2% w/v. In some embodiments, the one or more surfactants is present at a concentration of 0.2-1% w/v. In some embodiments, the one or more surfactants is present at a concentration of about 0.1%, about 0.2%, about 0.3%, about 0.4%, about 0.5%, about 0.75%, about 1% or about 1.5% w/v. In some embodiments, the one or more surfactants is present at a concentration of about 0.2% or about 1% w/v.

In some embodiments, a composition of the invention further comprises a buffer. In some embodiments, the buffer is phosphate buffer, MES buffer, PIPES buffer, HePES buffer, maleate and succinate buffer. In some embodiments, the buffer is a phosphate buffer, e.g., phosphate buffered saline (PBS), sodium phosphate buffer or potassium phosphate buffer.

In some embodiments, a composition of the invention further comprises a salt. In some embodiments, salt is at a concentration a concentration of 50 mM-200 mM. In some embodiments, the salt is at a concentration a concentration of at least 10 mM. In some embodiments, the salt is sodium chloride.

In some embodiments, a composition of the invention further comprises an excipient. In some embodiments, the excipient is a sugar. In some embodiments, the sugar is a disaccharide, such as sucrose or trehalose. In some embodiments, the excipient is at a concentration at least 1%, at least 2%, at least 5% or at least 10% w/v. In some embodiments, the excipient is at a concentration of 1%-20% w/v. In some embodiments, the excipient is at a concentration of 2-10% w/v. In some embodiments, the excipient is at a concentration of 2-6% w/v. In some embodiments, the excipient is at a concentration of about 2%, about 4%, about 6%, about 8% or about 10% w/v. In some embodiments, the excipient is trehalose at a concentration a concentration of 2-10% w/v.

The lipid nanoparticle in a composition of the invention can comprise one or more cationic lipids, one or more non-cationic lipids, and one or more PEG-modified lipids. In some embodiments, the cationic lipid is selected from imidazole cholesterol ester (ICE), GL-TES-SA-DMP-E18-2, GL-TES-SA-DME-E18-2, TL1-01D-DMA, TL1-04D-DMA, SY-3-E14-DMAPr, SI-4-E14-DMAPr, SY-010, TL1-10D-DMA, HEP-E3-E10, HEP-E4-E10, and Guan-SS-Chol. In particular embodiments, the cationic lipid is SY-3-E14-DMAPr, SI-4-E14-DMAPr or SY-010. In some embodiments, the non-cationic lipid is DOPE, DEPE, DPPC or DOPC-. In some embodiments, the PEG-modified lipid is DMG-PEG2K. In some embodiments, the lipid nanoparticle further comprises one or more cholesterol-based lipids, e.g., cholesterol. In some embodiments, the molar ratio of cationic lipid to non-cationic lipid to cholesterol to PEG-modified lipid is between about 30-60:10-35:20-30:1-15, respectively. For example, the molar ratio of cationic lipid to non-cationic lipid to cholesterol to PEG-modified lipid may be between about 30-60:25-35:20-30:1-15, respectively. In certain embodiments, the molar ratio of cationic lipid to non-cationic lipid to cholesterol to PEG-modified lipid is between about 41-70:9-18:9-48: 2-6. In some embodiments, the lipid nanoparticle comprises no more than three distinct lipid components. In some embodiments, one distinct lipid component is a sterol-based cationic lipid. In some embodiments, the no more than three distinct lipid components are a cationic lipid, a non-cationic lipid and a PEG-modified lipid. In some embodiments, the cationic lipid is imidazole cholesterol ester (ICE) or Guan-SS-Chol, the non-cationic lipid is 1,2-dioleoyl-sn-glycero-3-phosphoethanolamine (DOPE), and the PEG-modified lipid is 1,2-dimyristoyl-sn-glycerol, methoxypolyethylene glycol (DMG-PEG-2K). In some embodiments, the ICE/Guan-SS-Chol and DOPE are present at a molar ratio of >1:1. In some embodiments, the ICE/Guan-SS-Chol and DMG-PEG-2K are present at a molar ratio of >10:1. In some embodiments, the DOPE and DMG-PEG-2K are present at a molar ratio of >5:1.

In some embodiments, the lipid nanoparticle in a composition of the invention has a size less than about 100 nm, e.g., between 40 nm and 60 nm.

In some embodiments, the mRNA encapsulated in the lipid nanoparticle in a composition of the invention is codon-optimized. In some embodiments, the mRNA comprises at least one nonstandard nucleobase. In some embodiments, the nonstandard nucleobase is a nucleoside analog selected from the group consisting of: 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, pseudouridine (e.g., N-1-methyl-pseudouridine), 2-thiouridine, and 2-thiocytidine.

Compositions of the invention are for pulmonary delivery. In some embodiments, the pulmonary delivery is via nebulization. In some embodiments, the size of the lipid nanoparticle before and after nebulization varies by no more than 400%. In some embodiments, a composition of the invention is capable of being nebulized at a nebulization output rate of at least 12 ml/h. In some embodiments, a composition of the invention is capable of being nebulized at a nebulization rate of at least 15 ml/h. In some embodiments, the nebulization is performed with a vibrating mesh nebulizer.

The invention also provides methods for delivering mRNA in vivo by administering a composition of the invention via pulmonary delivery to a subject. In some embodiments, the pulmonary delivery is intranasal administration or inhalation. In some embodiments, the composition is nebulized prior to inhalation. In some embodiments, the composition is provided in lyophilized form and reconstituted in an aqueous solution prior to nebulization. In some embodiments, the mRNA encodes a protein. In some embodiments, the mRNA is delivered to the lungs. In some embodiments, the protein encoded by the mRNA is expressed in the lung. In some embodiments, the protein is a secreted protein. In some embodiments, the protein is an antibody or an antigen.

The invention also provides methods of treating or preventing a disease or disorder in a subject, the method comprising administering a composition of the invention via pulmonary delivery to the subject. In some embodiments, the pulmonary delivery is via nebulization. In some embodiments, the disease or disorder is selected from a pulmonary disease or disorder (e.g., a chronic respiratory diseases) a protein deficiency (e.g., a protein deficiency affecting the lung), a neoplastic disease, (e.g., a tumour) and an infectious disease. In some embodiments, the disease or disorder is a protein deficiency. In some embodiments, the mRNA encodes the deficient protein. In some embodiments, the protein deficiency is cystic fibrosis. In some embodiments, the mRNA encodes CFTR. In some embodiments, the protein deficiency is primary ciliary dyskinesia. In some embodiments, the mRNA encodes DNAI1. In some embodiments, the protein deficiency is a surfactant deficiency. In some embodiments, the RNA is an mRNA encoding a surfactant protein.

In some embodiments, the pulmonary disease or disorder is a chronic respiratory disease. In some embodiments, the chronic respiratory disease is chronic obstructive pulmonary disease (COPD), asthma, pulmonary arterial hypertension or idiopathic pulmonary fibrosis. In some embodiments, the mRNA encodes a protein for treating a symptom of a pulmonary disease or disorder. In some embodiments, the mRNA encodes an antibody directed against a pro-inflammatory cytokine. In some embodiments, the disease or disorder is a neoplastic disease, e.g. a tumour. In some embodiments, the mRNA encodes an antibody targeting a protein expressed on the surface of neoplastic cells, e.g., the cells making up the tumour.

In some embodiments, the disease or disorder is an infectious disease. In some embodiments, the infectious disease is caused by a virus. In some embodiments, the mRNA encodes a soluble decoy receptor that binds a surface protein of the virus. In some embodiments, the mRNA encodes an antibody directed to a surface protein of the virus. In some embodiments, the infectious disease is caused by a bacterium. In some embodiments, the mRNA encodes an antigen derived from a causative agent of the infections disease. In some embodiments, the mRNA encodes an antibody directed to a surface protein of the bacterium. In some embodiments, the subject is human.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only, not for limitation.

DEFINITIONS

Figure 1A:
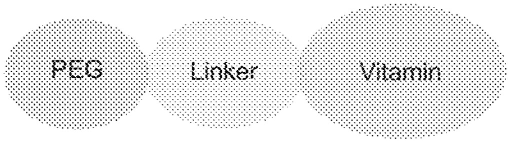
FIG. 1A demonstrates the structure of the surfactants of the invention and FIG. 1B illustrates the structure of TPGS.
Figure 1B:
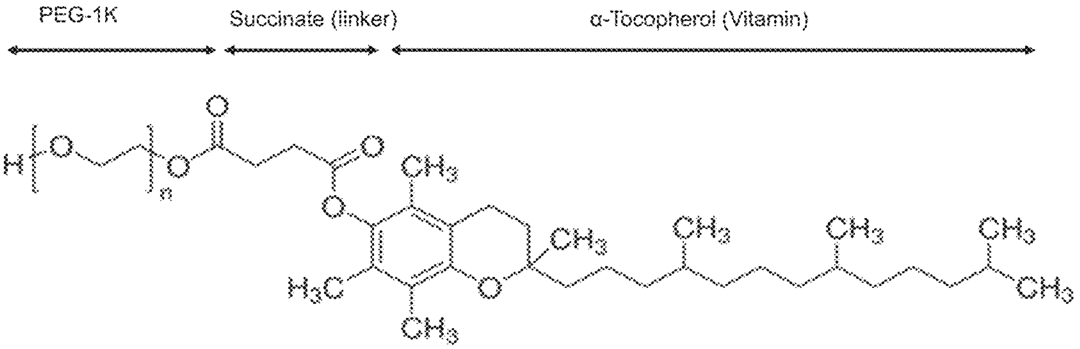

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Approximately or about: As used herein, the term "approximately" or "about," as applied to one or more values of interest, refers to a value that is similar to a stated reference value. In certain embodiments, the term "approximately" or "about" refers to a range of values that fall within 5%, 4%, 3%, 2%, or 1% in either direction (greater than or less than; e.g., ±2.5%) of the stated reference value, unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery). In some embodiments, delivery is pulmonary delivery, e.g., comprising nebulization.

Encapsulation: As used herein, the term "encapsulation," or grammatical equivalent, refers to the process of confining an mRNA molecule within a lipid nanoparticle.

Expression: As used herein, "expression" of an mRNA refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalents, are used interchangeably.

Half-life: As used herein, the term "half-life" is the time required for a quantity such as nucleic acid or protein concentration or activity to fall to half of its value as measured at the beginning of a time period.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Stable: As used herein, the term "stable" refers to a composition that retains its physical stability and/or biological activity. In one embodiment, stability is determined based on the percentage of mRNA which is degraded (e.g., fragmented). In another embodiment, stability is determined based on the percentage of lipid nanoparticles that are no longer in suspension.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. In some embodiments, a subject can be a patient, which refers to a human presenting to a medical provider for diagnosis or treatment of a disease or disorder. The term "subject" is used herein interchangeably with "individual" or "patient." A subject can be afflicted with or is susceptible to a disease or disorder but may or may not display symptoms of the disease or disorder. In some embodiments, a subject may be healthy and receive a lipid nanoparticle or composition of the invention for the prevention of a disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Chemical Definitions

Acyl: As used herein, the term "acyl" refers to $R^Z$—(C═O)—, wherein $R^Z$ is, for example, any alkyl, alkenyl, alkynyl, heteroalkyl or heteroalkylene.

Aliphatic: As used herein, the term aliphatic refers to $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ alkyls (e.g., linear or branched $C_1$-$C_{20}$ saturated alkyls), $C_2$-$C_{20}$ alkenyls (e.g., linear or branched $C_4$-$C_{20}$ dienyls, linear or branched $C_6$-$C_{20}$ trienyls, and the like), and $C_2$-$C_{20}$ alkynyls (e.g., linear or branched $C_2$-$C_{20}$ alkynyls). $C_1$-$C_{20}$ aliphatics can include $C_3$-$C_{20}$ cyclic aliphatics (e.g., $C_3$-$C_{20}$ cycloalkyls, $C_4$-$C_{20}$ cycloalkenyls, or $C_8$-$C_{20}$ cycloalkynyls). In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. An aliphatic group is unsubstituted or substituted with one or more substituent groups as described herein. For example, an aliphatic may be substituted with one or more (e.g., 1, 2, 3, 4, 5, or 6 independently selected substituents) of halogen, —COR", —$CO_2$H, —$CO_2$R", —CN, —OH, —OR", —OCOR', —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the aliphatic is unsubstituted. In embodiments, the aliphatic does not include any heteroatoms. Alkyl: As used herein, the term "alkyl" means acyclic linear and branched hydrocarbon groups, e.g. "$C_1$-$C_{30}$ alkyl" refers to alkyl groups having 1-30 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, isohexyl, etc. The term "lower alkyl" means an alkyl group straight chain or branched alkyl having 1 to 6 carbon atoms. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —COR", —$CO_2$H, —$CO_2$R", —CN, —OH, —OR", —OCOR', —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the alkyl is substituted (e.g., with 1, 2, 3, 4, 5, or 6 substituent groups as described herein). In embodiments, an alkyl group is substituted with a —OH group and may also be referred to herein as a "hydroxyalkyl" group, where the prefix denotes the —OH group and "alkyl" is as described herein.

As used herein, "alkyl" also refers to a radical of a straight-chain or branched saturated hydrocarbon group having from 1 to 50 carbon atoms ("$C_1$-$C_{50}$ alkyl"). In some embodiments, an alkyl group has 1 to 40 carbon atoms ("$C_1$-$C_{40}$ alkyl"). In some embodiments, an alkyl group has 1 to 30 carbon atoms ("$C_1$-$C_{30}$ alkyl"). In some embodiments, an alkyl group has 1 to 20 carbon atoms ("$C_1$-$C_{20}$ alkyl"). In some embodiments, an alkyl group has 1 to 10 carbon atoms ("$C_1$-$C_{10}$ alkyl"). In some embodiments, an alkyl group has 1 to 9 carbon atoms ("$C_1$-$C_9$ alkyl"). In some embodiments, an alkyl group has 1 to 8 carbon atoms ("$C_1$-$C_5$ alkyl"). In some embodiments, an alkyl group has 1 to 7 carbon atoms ("$C_1$-$C_7$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include, without limitation, methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_1$-$C_{50}$ alkyl. In certain embodiments, the alkyl group is a substituted $C_1$-$C_{50}$ alkyl.

Affixing the suffix "-ene" to a group indicates the group is a divalent moiety, e.g., arylene is the divalent moiety of aryl, and heteroarylene is the divalent moiety of heteroaryl.

Alkylene: The term "alkylene," as used herein, represents a saturated divalent straight or branched chain hydrocarbon group and is exemplified by methylene, ethylene, isopropylene and the like. Likewise, the term "alkenylene" as used herein represents an unsaturated divalent straight or branched chain hydrocarbon group having one or more unsaturated carbon-carbon double bonds that may occur in any stable point along the chain, and the term "alkynylene" herein represents an unsaturated divalent straight or branched chain hydrocarbon group having one or more unsaturated carbon-carbon triple bonds that may occur in any stable point along the chain. In certain embodiments, an alkylene, alkenylene, or alkynylene group may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. For example, an alkylene, alkenylene, or alkynylene may be substituted with one or more (e.g., 1, 2, 3, 4, 5, or 6 independently selected substituents) of halogen, —COR", —$CO_2$H, —$CO_2$R", —CN, —OH, —OR", —OCOR", —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In certain embodiments, an alkylene, alkenylene, or alkynylene is unsubstituted. In certain embodiments, an alkylene, alkenylene, or alkynylene does not include any heteroatoms. Alkenyl: As used herein, “alkenyl” means any linear or branched hydrocarbon chains having one or more unsaturated carbon-carbon double bonds that may occur in any stable point along the chain, e.g. “$C_2$-$C_{30}$ alkenyl” refers to an alkenyl group having 2-30 carbons. For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. In embodiments, the alkenyl comprises 1, 2, or 3 carbon-carbon double bond. In embodiments, the alkenyl comprises a single carbon-carbon double bond. In embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —COR", —$CO_2$H, —$CO_2$R", —CN, —OH, —OR", —OCOR", —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the alkenyl is unsubstituted. In embodiments, the alkenyl is substituted (e.g., with 1, 2, 3, 4, 5, or 6 substituent groups as described herein). In embodiments, an alkenyl group is substituted with a —OH group and may also be referred to herein as a “hydroxyalkenyl” group, where the prefix denotes the —OH group and “alkenyl” is as described herein.

As used herein, “alkenyl” also refers to a radical of a straight-chain or branched hydrocarbon group having from 2 to 50 carbon atoms and one or more carbon-carbon double bonds (e.g., 1, 2, 3, or 4 double bonds) (“$C_2$-$C_{50}$ alkenyl”). In some embodiments, an alkenyl group has 2 to 40 carbon atoms (“$C_2$-$C_{40}$ alkenyl”). In some embodiments, an alkenyl group has 2 to 30 carbon atoms (“$C_2$-$C_{30}$ alkenyl”). In some embodiments, an alkenyl group has 2 to 20 carbon atoms (“$C_2$-$C_{20}$ alkenyl”). In some embodiments, an alkenyl group has 2 to 10 carbon atoms (“$C_2$-$C_{10}$ alkenyl”). In some embodiments, an alkenyl group has 2 to 9 carbon atoms (“$C_2$-$C_9$ alkenyl”). In some embodiments, an alkenyl group has 2 to 8 carbon atoms (“$C_2$-$C_8$ alkenyl”). In some embodiments, an alkenyl group has 2 to 7 carbon atoms (“$C_2$-$C_7$ alkenyl”). In some embodiments, an alkenyl group has 2 to 6 carbon atoms (“$C_2$-$C_6$ alkenyl”). In some embodiments, an alkenyl group has 2 to 5 carbon atoms (“$C_2$-$C_5$ alkenyl”). In some embodiments, an alkenyl group has 2 to 4 carbon atoms (“$C_2$-$C_4$ alkenyl”). In some embodiments, an alkenyl group has 2 to 3 carbon atoms (“$C_2$-$C_3$ alkenyl”). In some embodiments, an alkenyl group has 2 carbon atoms (“$C_2$ alkenyl”). The one or more carbon-carbon double bonds can be internal (such as in 2-butenyl) or terminal (such as in 1-butenyl). Examples of $C_2$-$C_4$ alkenyl groups include, without limitation, ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_2$-$C_4$ alkenyl groups as well as pentenyl ($C_5$), pentadienyl ($C_5$), hexenyl ($C_6$), and the like. Additional examples of alkenyl include heptenyl ($C_7$), octenyl ($C_5$), octatrienyl ($C_5$), and the like. Unless otherwise specified, each instance of an alkenyl group is independently unsubstituted (an “unsubstituted alkenyl”) or substituted (a “substituted alkenyl”) with one or more substituents. In certain embodiments, the alkenyl group is an unsubstituted $C_2$-$C_{50}$ alkenyl. In certain embodiments, the alkenyl group is a substituted $C_2$-$C_{50}$ alkenyl.

Alkynyl: As used herein, “alkynyl” means any hydrocarbon chain of either linear or branched configuration, having one or more carbon-carbon triple bonds occurring in any stable point along the chain, e.g., “$C_2$-$C_{30}$ alkynyl”, refers to an alkynyl group having 2-30 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, etc. In embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —COR", —$CO_2$H, —$CO_2$R", —CN, —OH, —OR", —OCOR", —$OCO_2$R", —$NH_2$, —NHR", —N(R")$_2$, —SR" or —$SO_2$R", wherein each instance of R" independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R" independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R" independently is unsubstituted $C_1$-$C_3$ alkyl. In embodiments, the alkynyl is unsubstituted. In embodiments, the alkynyl is substituted (e.g., with 1, 2, 3, 4, 5, or 6 substituent groups as described herein).

As used herein, “alkynyl” also refers to a radical of a straight-chain or branched hydrocarbon group having from 2 to 50 carbon atoms and one or more carbon-carbon triple bonds (e.g., 1, 2, 3, or 4 triple bonds) and optionally one or more double bonds (e.g., 1, 2, 3, or 4 double bonds) (“$C_2$-$C_{50}$ alkynyl”). An alkynyl group that has one or more triple bonds and one or more double bonds is also referred to as an “ene-yne”. In some embodiments, an alkynyl group has 2 to 40 carbon atoms (“$C_2$-$C_{40}$ alkynyl”). In some embodiments, an alkynyl group has 2 to 30 carbon atoms (“$C_2$-$C_{30}$ alkynyl”). In some embodiments, an alkynyl group has 2 to 20 carbon atoms (“$C_2$-$C_{20}$ alkynyl”). In some embodiments, an alkynyl group has 2 to 10 carbon atoms (“$C_2$-$C_{10}$ alkynyl”). In some embodiments, an alkynyl group has 2 to 9 carbon atoms (“$C_2$-$C_9$ alkynyl”). In some embodiments, an alkynyl group has 2 to 8 carbon atoms (“$C_2$-$C_8$ alkynyl”). In some embodiments, an alkynyl group has 2 to 7 carbon atoms (“$C_2$-$C_7$ alkynyl”). In some embodiments, an alkynyl group has 2 to 6 carbon atoms (“$C_2$-$C_6$ alkynyl”). In some embodiments, an alkynyl group has 2 to 5 carbon atoms (“$C_2$-$C_5$ alkynyl”). In some embodiments, an alkynyl group has 2 to 4 carbon atoms (“$C_2$-$C_4$ alkynyl”). In some embodiments, an alkynyl group has 2 to 3 carbon atoms (“$C_2$-$C_3$ alkynyl”). In some embodiments, an alkynyl group has 2 carbon atoms (“$C_2$ alkynyl”). The one or more carbon-triple bonds can be internal (such as in 2-butynyl) or terminal (such as in 1-butynyl). Examples of $C_2$-$C_4$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_2$-$C_6$ alkenyl groups include the aforementioned $C_2$-$C_4$ alkynyl groups as well as pentynyl ($C_5$), hexynyl ($C_6$), and the like. Additional examples of alkynyl include heptynyl ($C_7$), octynyl ($C_5$), and the like. Unless otherwise specified, each instance of an alkynyl group is independently unsubstituted (an “unsubstituted alkynyl”) or substituted (a “substituted alkynyl”) with one or more substituents. In certain embodiments, the alkynyl group is an unsubstituted $C_2$-$C_{50}$ alkynyl. In certain embodiments, the alkynyl group is a substituted $C_2$-$C_{50}$ alkynyl.

Aryl: The term "aryl" used alone or as part of a larger moiety as in "aralkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. In embodiments, an aryl group has 6 ring carbon atoms ("$C_6$ aryl," e.g., phenyl). In some embodiments, an aryl group has 10 ring carbon atoms ("$C_{10}$ aryl," e.g., naphthyl such as 1-naphthyl and 2-naphthyl). In some embodiments, an aryl group has 14 ring carbon atoms ("$C_{14}$ aryl," e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Exemplary aryls include phenyl, naphthyl, and anthracene.

As used herein, "aryl" also refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_6$-$C_{14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_6$-$C_{14}$ aryl. In certain embodiments, the aryl group is a substituted $C_6$-$C_{14}$ aryl.

Arylene: The term "arylene" as used herein refers to an aryl group that is divalent (that is, having two points of attachment to the molecule). Exemplary arylenes include phenylene (e.g., unsubstituted phenylene or substituted phenylene).

Carbocyclyl: As used herein, "carbocyclyl" or "carbocyclic" refers to a radical of a non-aromatic cyclic hydrocarbon group having from 3 to 10 ring carbon atoms ("$C_3$-$C_{10}$ carbocyclyl") and zero heteroatoms in the non-aromatic ring system. In some embodiments, a carbocyclyl group has 3 to 8 ring carbon atoms ("$C_3$-$C_8$ carbocyclyl"). In some embodiments, a carbocyclyl group has 3 to 7 ring carbon atoms ("$C_3$-$C_7$ carbocyclyl"). In some embodiments, a carbocyclyl group has 3 to 6 ring carbon atoms ("$C_3$-$C_6$ carbocyclyl"). In some embodiments, a carbocyclyl group has 4 to 6 ring carbon atoms ("$C_4$-$C_6$ carbocyclyl"). In some embodiments, a carbocyclyl group has 5 to 6 ring carbon atoms ("$C_5$-$C_6$ carbocyclyl"). In some embodiments, a carbocyclyl group has 5 to 10 ring carbon atoms ("$C_5$-$C_{10}$ carbocyclyl"). Exemplary $C_3$-$C_6$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ carbocyclyl groups include, without limitation, the aforementioned $C_3$-$C_6$ carbocyclyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), bicyclo[2.2.1]heptanyl ($C_7$), bicyclo[2.2.2]octanyl ($C_5$), and the like. Exemplary $C_3$-$C_{10}$ carbocyclyl groups include, without limitation, the aforementioned $C_3$-$C_8$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_3$-$C_{10}$ carbocyclyl. In certain embodiments, the carbocyclyl group is a substituted $C_3$-$C_{10}$ carbocyclyl.

In some embodiments, "carbocyclyl" or "carbocyclic" is referred to as a "cycloalkyl", i.e., a monocyclic, saturated carbocyclyl group having from 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$, cycloalkyl"). In some embodiments, a cycloalkyl group has 4 to 6 ring carbon atoms ("$C_4$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 10 ring carbon atoms ("$C_5$-$C_{10}$ cycloalkyl"). Examples of $C_5$-$C_6$ cycloalkyl groups include cyclopentyl ($C_5$) and cyclohexyl ($C_5$). Examples of $C_3$-$C_6$ cycloalkyl groups include the aforementioned $C_5$-$C_6$ cycloalkyl groups as well as cyclopropyl ($C_3$) and cyclobutyl ($C_4$). Examples of $C_3$-$C_5$ cycloalkyl groups include the aforementioned $C_3$-$C_6$ cycloalkyl groups as well as cycloheptyl ($C_7$) and cyclooctyl ($C_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_3$-$C_{10}$ cycloalkyl. In certain embodiments, the cycloalkyl group is a substituted $C_3$-$C_{10}$ cycloalkyl.

Halogen: As used herein, the term "halogen" means fluorine, chlorine, bromine, or iodine.

Heteroalkyl: The term "heteroalkyl" is meant a branched or unbranched alkyl, alkenyl, or alkynyl group having from 1 to 14 carbon atoms in addition to 1, 2, 3 or 4 heteroatoms independently selected from the group consisting of N, O, S, and P. Heteroalkyls include tertiary amines, secondary amines, ethers, thioethers, amides, thioamides, carbamates, thiocarbamates, hydrazones, imines, phosphodiesters, phosphoramidates, sulfonamides, and disulfides. A heteroalkyl group may optionally include monocyclic, bicyclic, or tricyclic rings, in which each ring desirably has three to six members. Examples of heteroalkyls include polyethers, such as methoxymethyl and ethoxyethyl.

Heteroalkylene: The term "heteroalkylene," as used herein, represents a divalent form of a heteroalkyl group as described herein.

Heteroaryl: The term "heteroaryl," as used herein, is fully unsaturated heteroatom-containing ring wherein at least one ring atom is a heteroatom such as, but not limited to, nitrogen and oxygen.

As used herein, "heteroaryl" also refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1 or more (e.g., 1, 2, 3, or 4 ring heteroatoms) ring heteroatoms provided in the aromatic ring system, wherein each heteroatom is independently selected from oxygen, sulfur, nitrogen, boron, silicon, and phosphorus ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-10 membered heteroaryl"). In some embodiments, a heteroaryl group is a 5-8 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-8 membered heteroaryl"). In some embodiments, a heteroaryl group is a 5-6 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-6 membered heteroaryl"). In some embodiments, the 5-6 membered heteroaryl has 1 or more (e.g., 1, 2, or 3) ring heteroatoms selected from oxygen, sulfur, nitrogen, boron, silicon, and phosphorus. In some embodiments, the 5-6 membered heteroaryl has 1 or 2 ring heteroatoms selected from oxygen, sulfur, nitrogen, boron, silicon, and phosphorus. In some embodiments, the 5-6 membered heteroaryl has 1 ring heteroatom selected from oxygen, sulfur, nitrogen, boron, silicon, and phosphorus. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, "heterocyclyl" or "heterocyclic" refers to a radical of a 3- to 14-membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-10 membered heterocyclyl"). In some embodiments, a heterocyclyl group is a 5-8 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-8 membered heterocyclyl"). In some embodiments, a heterocyclyl group is a 5-6 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-6 membered heterocyclyl"). In some embodiments, the 5-6 membered heterocyclyl has 1 or more (e.g., 1, 2, or 3) ring heteroatoms selected from oxygen, sulfur, nitrogen, boron, silicon, and phosphorus. In some embodiments, the 5-6 membered heterocyclyl has 1 or 2 ring heteroatoms selected from oxygen, sulfur, nitrogen, boron, silicon, and phosphorus. In some embodiments, the 5-6 membered heterocyclyl has 1 ring heteroatom selected from oxygen, sulfur, nitrogen, boron, silicon, and phosphorus.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation. tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Heterocycloalkyl: The term "heterocycloalkyl," as used herein, is a non-aromatic ring wherein at least one atom is a heteroatom such as, but not limited to, nitrogen, oxygen, sulfur, or phosphorus, and the remaining atoms are carbon. The heterocycloalkyl group can be substituted or unsubstituted.

As understood from the above, alkyl, alkenyl, alkynyl, acyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or 'unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2$, —$SO_3H$, —OH, —$OR^{aa}$, —$ON(R^{bb})_2$, —$N(R^{bb})_2$, —$N(R^{bb})_3$+$X^-$—, —$N(OR^{cc})R^{bb}$, —SeH, —$SeR^{aa}$, —SH, —$SR^{aa}$, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —OSO2$R^{aa}$, —S(═O)$R^{aa}$, —OS(═O)$R^{aa}$, —$Si(R^{aa})_3$—$OSi(R^{aa})_3$—C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$_2R^{aa}$, —OP(═O)$_2R^{aa}$, —P(═O)$(R^{aa})_2$, —OP(═O)$(R^{aa})_2$, —OP(═O)$(OR^{cc})_2$, —P(═O)$_2N(R^{bb})_2$, —OP(═O)$_2N(R^{bb})_2$, —P(═O)$(NR^{bb})_2$, —OP(═O)$(NR^{bb})_2$, —$NR^{bb}$P(═O)$(OR^{cc})_2$, —$NR^{bb}$P(═O)$(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, $C_1$-$C_{50}$ alkyl, $C_2$-$C_{50}$ alkenyl, $C_2$-$C_{50}$ alkynyl, $C_3$-$C_{14}$ carbocyclyl, 3-14 membered heterocyclyl, $C_6$-$C_{14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group ═O, ═S, ═$NN(R^{bb})_2$, ═$NNR^{bb}$C(═O)$R^{aa}$, ═$NNR^{bb}$C(═O)$OR^{aa}$, ═$NNR^{bb}$S(═O)$_2$R—, ═$NR^{bb}$, or ═$NOR^{cc}$;

each instance of $R^{aa}$ is, independently, selected from $C_1$-$C_{50}$ alkyl, $C_2$-$C_{50}$ alkenyl, $C_2$-$C_{50}$ alkynyl, $C_3$-$C_{10}$ carbocyclyl, 3-14 membered heterocyclyl, $C_6$-$C_{14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$—$N(R^{cc})_2$, —CN, —C(=O)$R^{aa}$, —C(=O)$N(R^{cc})_2$, —$CO_2R^{aa}$, —$SO_2R^{aa}$, —C(=$NR^{cc}$)OR a, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, —P(=O)$_2R^{aa}$, —P(=O)$(R^{aa})_2$, —P(=O)$_2N(R^{cc})_2$, —P(=O)$(NR^{cc})_2$, $C_1$-$C_{50}$ alkyl, $C_2$-$C_{50}$ alkenyl, $C_2$-$C_{50}$ alkynyl, $C_3$-$C_{10}$ carbocyclyl, 3-14 membered heterocyclyl, $C_6$-$C_{14}$ aryl, and 5-14 membered heteroaryl, or two $R^{bb}$ groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_1$-$C_{50}$ alkyl, $C_2$-$C_{50}$ alkenyl, $C_2$-$C_{50}$ alkynyl, $C_3$-$C_{10}$ carbocyclyl, 3-14 membered heterocyclyl, $C_6$-$C_{14}$ aryl, and 5-14 membered heteroaryl, or two $R^{cc}$ groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{cc}$, —$ON(R^{ff})_2$, —$N(R^{ff})_2$, —$N(R^{ff})_3$+$X^-$—, —N($OR^{ee}$)$R^{ff}$, —SH, —$SR^{ee}$, —$SSR^{ee}$—C(=O)$R^{ee}$, —$CO_2H$, —$CO_2R^{ee}$, —OC(=O)$R^{ee}$, —$OCO_2R^{ee}$, —C(=O)$N(R^{ff})_2$, —OC(=O)$N(R^{ff})_2$, —$NR^{ff}$C(=O)$R^{ee}$, —$NR^{ff}CO_2R^{ee}$, —$NR^{ff}$C(=O)$N(R^{ff})_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)$N(R^{ff})_2$, —OC(=$NR^{ff}$)$N(R^{ff})_2$, —$NR^{ff}$C(=$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —$Si(R^{ee})_3$, —$OSi(R^{ee})_3$, —C(=S)$N(R^{ff})_2$, —C(=O)$SR^{ee}$, —C(=S)$SR^{ee}$, —SC(=S)$SR^{ee}$, —P(=O)$_2R^{ee}$, —P(=O)$(R^{ee})_2$, —OP(=O)$(R^{ee})_2$, —OP(=O)$(OR^{ee})_2$, $C_1$-$C_{50}$ alkyl, $C_2$-$C_{50}$ alkenyl, $C_2$-$C_{50}$ alkynyl, $C_3$-$C_{10}$ carbocyclyl, 3-10 membered heterocyclyl, $C_6$-$C_{10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_1$-$C_{50}$ alkyl, $C_2$-$C_{50}$ alkenyl, $C_2$-$C_{50}$ alkynyl, $C_3$-$C_{10}$ carbocyclyl, $C_6$-$C_{10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_1$-$C_{50}$ alkyl, $C_2$-$C_{50}$ alkenyl, $C_2$-$C_{50}$ alkynyl, $C_3$-$C_{10}$ carbocyclyl, 3-10 membered heterocyclyl, $C_6$-$C_{10}$ aryl and 5-10 membered heteroaryl, or two $R^{ff}$ groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_1$-$C_{50}$ alkyl, —ON($C_1$-$C_{50}$ alkyl)$_2$, —N($C_1$-$C_{50}$ alkyl)$_2$, —N($C_1$-$C_{50}$ alkyl)$_3$+$X^-$—, —NH($C_1$-$C_{50}$ alkyl)$_2$+$X^-$—, —$NH_2$($C_1$-$C_{50}$ alkyl)+$X^-$—, —$NH_3$+$X^-$—, —N($OC_1$-$C_{50}$ alkyl)($C_1$-$C_{50}$ alkyl), —N(OH)($C_1$-$C_{50}$ alkyl), —NH(OH), —SH, —$SC_1$-$C_{50}$ alkyl, —SS($C_1$-$C_{50}$ alkyl), —C(=O)($C_1$-$C_{50}$ alkyl), —$CO_2H$, —$CO_2$($C_1$-$C_{50}$ alkyl), —OC(=O)($C_1$-$C_{50}$ alkyl), —$OCO_2$($C_1$-$C_{50}$ alkyl), —C(=O)$NH_2$, —C(=O)N($C_1$-$C_{50}$ alkyl)$_2$, —OC(=O)NH($C_1$-$C_{50}$ alkyl), —NHC(=O)($C_1$-$C_{50}$ alkyl), —N($C_1$-$C_{50}$ alkyl)C(=O)($C_1$-$C_{50}$ alkyl), —NHCO2($C_1$-$C_{50}$ alkyl), —NHC(=O)N($C_1$-$C_{50}$ alkyl)$_2$, —NHC(=O)NH($C_1$-$C_{50}$ alkyl), —NHC(=O)$NH_2$, —C(=NH)O($C_1$-$C_{50}$ alkyl), —OC(=NH)($C_1$-$C_{50}$ alkyl), —OC(=NH)$OC_1$-$C_{50}$ alkyl, —C(=NH)N($C_1$-$C_{50}$ alkyl)$_2$, —C(=NH)NH($C_1$-$C_{50}$ alkyl), —C(=NH)$NH_2$, —OC(=NH)N($C_1$-$C_{50}$alkyl)$_2$, —OC(NH)NH($C_1$-$C_{50}$ alkyl), —OC(NH)$NH_2$, —NHC(NH)N($C_1$-$C_{50}$ alkyl)$_2$, —NHC(=NH)$NH_2$, —$NHSO_2$($C_1$-$C_{50}$ alkyl), —$SO_2$N($C_1$-$C_{50}$ alkyl)$_2$, —$SO_2$NH($C_1$-$C_{50}$ alkyl), —$SO_2NH_2$, —$SO_2$($C_1$-$C_{50}$ alkyl), —$SO_2$O($C_1$-$C_{50}$ alkyl), —$OSO_2$($C_1$-$C_6$ alkyl), —SO($C_1$-$C_6$ alkyl), —Si($C_1$-$C_{50}$ alkyl)$_3$, —OSi($C_1$-$C_6$ alkyl)$_3$, —C(=S)N($C_1$-$C_{50}$ alkyl)$_2$, C(=S)NH($C_1$-$C_{50}$ alkyl), C(=S)$NH_2$, —C(=O)S($C_1$-$C_6$ alkyl), —C(=S)S($C_1$-$C_6$ alkyl), —SC(=S)S($C_1$-$C_6$ alkyl), —P(=O)$_2$($C_1$-$C_{50}$ alkyl), —P(=O)($C_1$-$C_{50}$ alkyl)$_2$, —OP(=O)($C_1$-$C_{50}$ alkyl)$_2$, —OP(=O)($OC_1$-$C_{50}$ alkyl)$_2$, $C_1$-$C_{50}$ alkyl, $C_2$-$C_{50}$ alkenyl, $C_2$-$C_{50}$ alkynyl, $C_3$-$C_{10}$ carbocyclyl, $C_6$-$C_{10}$ aryl, 3-10 membered heterocyclyl, 5-10 membered heteroaryl; or two geminal $R^{99}$ substituents can be joined to form =O or =S; wherein $X^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —$N(R^{cc})_2$, —CN, —C(=O)$R^{aa}$, —C(=O)$N(R^{cc})_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, —P(=O)$_2R^{aa}$, —P(=O)$(R^{aa})_2$, —P(=O)$_2N(R^{cc})_2$, —P(=O)$(NR^{cc})_2$, $C_1$-$C_{50}$ alkyl, $C_2$-$C_{50}$ alkenyl, $C_2$-$C_{50}$ alkynyl, $C_3$-$C_{10}$ carbocyclyl, 3-14 membered heterocyclyl, $C_6$-$C_{14}$ aryl, and 5-14 membered heteroaryl, or two $R^{cc}$ groups, together with the N atom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(═O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary sulfur protecting groups include, but are not limited to, alkyl, benzyl, p-methoxybenzyl, 2,4,6-trimethylbenzyl, 2,4,6-trimethoxybenzyl, o-hydroxybenzyl, p-hydroxybenzyl, o-acetoxybenzyl, p-acetoxybenzyl, p-nitrobenzyl, 4-picolyl, 2-quinolinylmethyl, 2-picolyl N-oxido, 9-anthrylmethyl, 9-fluorenylmethyl, xanthenyl, ferrocenylmethyl, diphenylmethyl, bis(4-methoxyphenyl)methyl, 5-dibenzosuberyl, triphenylmethyl, diphenyl-4-pyridylmethyl, phenyl, 2,4-dinitrophenyl, t-butyl, 1-adamantyl, methoxymethyl (MOM), isobutoxymethyl, benzyloxymethyl, 2-tetrahydropyranyl, benzylthiomethyl, phenylthiomethyl, thiazolidino, acetamidomethyl, trimethylacetamidomethyl, benzamidomethyl, allyloxycarbonylaminomethyl, phenylacetamidomethyl, phthalimidomethyl, acetylmethyl, carboxymethyl, cyanomethyl, (2-nitro-1-phenyl)ethyl, 2-(2,4-dinitrophenyl)ethyl, 2-cyanoethyl, 2-(Trimethylsilyl)ethyl, 2,2-bis(carboethoxy)ethyl, (1-m-nitrophenyl-2-benzoyl)othyl, 2-phenylsulfonylethyl, 2-(4-methylphenylsulfonyl)-2-methylprop-2-yl, acetyl, benzoyl, trifluoroacetyl, N-[[(p-biphenylyl)isopropoxy]carbonyl]-N-methyl]-γ-aminothiobutyrate, 2,2,2-trichloroethoxycarbonyl, t-butoxycarbonyl, benzyloxycarbonyl, p-methoxybenzyloxycarbonyl, N-ethyl, N-methoxymethyl, sulfonate, sulfenylthiocarbonate, 3-nitro-2-pyridinesulfenyl sulfide, oxathiolone.

DETAILED DESCRIPTION

The present invention provides, among other things, improved compositions that comprise an mRNA encapsulated in a lipid nanoparticle, and one or more surfactants consisting of an antioxidant moiety covalently linked via a linker moiety to a PEG moiety, wherein the one or more surfactants is present at a concentration of at least 0.1% weight to volume (w/v), which have higher nebulization rates and the lipid nanoparticles have improved characteristics post-nebulization.

Surfactants

The surfactants according to the present invention consist of an antioxidant moiety covalently linked via a linker moiety to a PEG moiety (see FIG. 1A for illustration). The antioxidant moiety can be a lipophilic vitamin. Examples of lipophilic vitamins include vitamin A, D, E or K. In some embodiments, the lipophilic vitamin is vitamin E or D.

An exemplary surfactant consisting of an antioxidant moiety covalently linked via a linker moiety to a PEG moiety is D-α-tocopheryl polyethylene glycol 1000 succinate (TPGS). TPGS has been used to nebulize hydrophobic small-molecule drugs such as celecoxib (Fulzele et al. 2006 Pharm Res. 23, 9, 2094-2106) and has previously been used as a component of lipid nanoparticles in combination with egg L-α-phosphatidylcholine and lanolin cholesterol (Valle et al. 2018 Appl. Sci. 8, 1291). In light of its use as a solubilizer, emulsifier, as well as a permeation and bioavailability enhancer of hydrophobic drugs, it was thought that TPGS and similar surfactants may not be suitable excipients in a composition comprising lipid nanoparticles encapsulating mRNA. The inventors surprisingly found that surfactants consisting of an antioxidant moiety covalently linked via a linker moiety to a PEG moiety, such as TPGS, can be used in compositions that comprise lipid nanoparticles and that these compositions have advantageous nebulization characteristics (e.g., an improved nebulization output rate).

In some embodiments, the linker moiety in the one or more surfactants included in the compositions of the invention can be succinate, oxalate, adipate, malonate, fumarate, malate, glutarate or maleate. In particular embodiments, the linker moiety in the one or more surfactants included in the compositions of the invention is succinate. Various different forms of PEG are known in the art and can be used in the invention. In some embodiments, the antioxidant moiety can be unmodified PEG, methoxy-PEG (mPEG) or carboxylic acid-functionalized PEG (COOH-PEG). The average molecular weight of the PEG moiety can vary. In some embodiments, the PEG moiety has an average molecular weight of between 0.1 kDa and 10 kDa. In a particular embodiment, PEG moiety has an average molecular weight of between 0.5 kDa and 5 kDa. In specific embodiments, the average molecular weight of the PEG moiety is about 1 KDa, about 2 KDa, about 3 KDa, about 3.4 KDa or about 5 KDa. In further specific embodiments, the PEG moiety has an average molecular weight of about 0.5 kDa, about 1 kDa, about 1.5 kDa, about 2 kDa, about 2.5 kDa or about 3 kDa.

A particularly suitable surfactant for use with a composition of the invention comprises a lipophilic vitamin, e.g., vitamin E or vitamin D, as its antioxidant moiety. Such surfactants typically have an unmodified PEG moiety of between 0.5 kDa and 5 kDa. A commonly used linker moiety is succinate. Accordingly, in some embodiments, the surfactant is selected from the group consisting of PEG-0.5K-succinate-vitamin E, PEG-0.75K-succinate-vitamin E, PEG-1K-succinate-vitamin E, PEG-2K-succinate-vitamin E, PEG-3K-succinate-vitamin E, PEG-3.4K-succinate-vitamin E, PEG-5K-succinate-vitamin E, PEG-0.5K-succinate-vitamin D, PEG-0.75K-succinate-vitamin D, PEG-1K-succinate-vitamin D, PEG-2K-succinate-vitamin D, PEG-3K-succinate-vitamin D, PEG-3.4K-succinate-vitamin D or PEG-5K-succinate-vitamin D.

Other particularly suitable surfactants for use with a composition of the invention comprise a lipophilic vitamin, e.g., vitamin E or vitamin D, as its antioxidant moiety and modified PEG moieties of between 0.5 kDa and 5 kDa. In some embodiments, the modified PEG moiety is mPEG. In some embodiments, the modified PEG moiety is COOH-PEG.

In some embodiments, the surfactant is selected from the group consisting of mPEG-0.5K-succinate-vitamin E, mPEG-0.75K-succinate-vitamin E, mPEG-1K-succinate-vitamin E, mPEG-2K-succinate-vitamin E, mPEG-3K-succinate-vitamin E, mPEG-3.4K-succinate-vitamin E, mPEG-5K-succinate-vitamin E, mPEG-0.5K-succinate-vitamin D, mPEG-0.75K-succinate-vitamin D, mPEG-1K-succinate-vitamin D, mPEG-2K-succinate-vitamin D, mPEG-3K-succinate-vitamin D, mPEG-3.4K-succinate-vitamin D or mPEG-5K-succinate-vitamin D.

In some embodiments, the surfactant is selected from the group consisting of COOH-PEG-0.5K-succinate-vitamin E, COOH-PEG-0.75K-succinate-vitamin E, COOH-PEG-1K-succinate-vitamin E, COOH-PEG-2K-succinate-vitamin E, COOH-PEG-3K-succinate-vitamin E, COOH-PEG-3.4K-succinate-vitamin E, COOH-PEG-5K-succinate-vitamin E, COOH-PEG-0.5K-succinate-vitamin D, COOH-PEG-0.75K-succinate-vitamin D, COOH-PEG-1K-succinate-vitamin D, COOH-PEG-2K-succinate-vitamin D, COOH-PEG-3K-succinate-vitamin D, COOH-PEG-3.4K-succinate-vitamin D or COOH-PEG-5K-succinate-vitamin D.

In a first specific embodiment, the surfactant is D-α-tocopheryl polyethylene glycol 1000 succinate (TPGS). In a second specific embodiment, the surfactant is mPEG-2K-succinate-vitamin E. In a third specific embodiment, the surfactant is COOH-PEG-3.4 k-succinate-vitamin E. In a fourth specific embodiment, the surfactant is mPEG-2K-succinate-vitamin D.

In a fifth specific embodiment, the surfactant is mPEG-2K-succinate-vitamin D. In a sixth specific embodiment, the surfactant is COOH-PEG-3.4 k-succinate-vitamin D. As demonstrated in the exemplified embodiments, TPGS is a particularly suitable surfactant for use in the compositions of the invention.

Surfactant Concentration

Figure 3A:
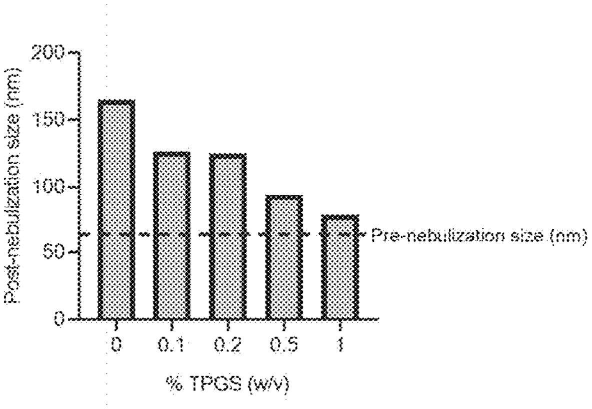
FIG. 3A demonstrates the effect of TPGS concentration on the size of the lipid nanoparticles post-nebulization and FIG. 3B demonstrates the effect of TPGS concentration on the nebulization (neb) flow rate and the post-nebulization encapsulation efficiency (EE %). The bars represent the nebulization flow rate and the triangles represent the encapsulation efficiency.

In some embodiments, the one or more surfactants consisting of an antioxidant moiety covalently linked via a linker moiety to a PEG moiety (e.g., TPGS) is present at concentration which reduces or prevents an increase in size of the lipid nanoparticles in the compositions of the invention upon nebulization (see FIG. 3A). In some embodiments, the one or more surfactants consisting of an antioxidant moiety covalently linked via a linker moiety to a PEG moiety (e.g., TPGS) is present at a concentration that reduces or prevents a loss in encapsulation efficiency of the lipid nanoparticles in the compositions of the invention upon nebulization (see FIG. 3B).

Accordingly, in some embodiments, the one or more surfactants is present at a concentration of at least 0.2%, at least 0.5% or at least 1% w/v. In some embodiments, the one or more surfactants is present at a concentration of 0.1-10% w/v, e.g., 0.1-5% w/v or 0.1-2% w/v. In particular embodiments, the one or more surfactants is present at a concentration of 0.2-1% w/v. In some embodiments, the one or more surfactants is present at a concentration of about 0.1%, about 0.2%, about 0.3%, about 0.4%, about 0.5%, about 0.6%, about 0.7%, about 0.75%, about 0.8%, about 0.9%, about 1%, about 1.25%, about 1.5%, about 1.75% or about 2% w/v. In some embodiments, the one or more surfactants is present at a concentration of about 0.1%, about 0.2%, about 0.3%, about 0.4% or about 0.5% w/v. In specific embodiments, the one or more surfactants are present at a concentration of about 0.5-1% w/v, e.g., at a concentration of about 0.5%, about 0.6%, about 0.7%, about 0.8%, about 0.9% or about 1% w/v.

Additional Excipients

The compositions of the invention can comprise further excipients in addition to the one or more surfactants. For example, the composition may further comprise a buffer, a salt, a sugar or combinations thereof.

Buffer

In some embodiments, the composition further comprises a buffer. In some embodiments, the composition comprises (a) an mRNA encapsulated in a lipid nanoparticle, (b) one or more surfactants consisting of an antioxidant moiety covalently linked via a linker moiety to a PEG moiety, and (c) a buffer, wherein the one or more surfactants is present at a concentration of at least 0.1% weight to volume (w/v).

Exemplary buffers that can be used in the compositions of the invention include a phosphate buffer, a citrate buffer, a Tris buffer, an imidazole buffer, a histidine buffer, a Good's buffer, MES, PIPES, HePES, a maleate buffer or a succinate buffer. In a specific embodiment, the buffer is a phosphate buffer, for example phosphate buffered saline (PBS), sodium phosphate buffer, potassium phosphate buffer or a citrate-phosphate buffer. In one particular embodiment, the buffer used in a composition of the invention is a sodium phosphate buffer. In another particular embodiment, the buffer used in a composition of the invention is a potassium phosphate buffer.

In some embodiments, the pH of the buffer is between pH 5-9. In some embodiments, the buffer has a pH of 5, 5.5, 6, 6.5, 7, 7.5, 8, 8.5 or 9. In some embodiments, the buffer has a pH of 7. The examples demonstrate that buffers with a pH lower than 7 can maintain the encapsulation efficiency after nebulization. Therefore, in particular embodiments the buffer has a pH that is lower than 7. For example, a suitable buffer (e.g., a sodium phosphate buffer or a potassium phosphate buffer) may have a pH of 5-6. In a specific embodiment, the buffer has a pH of about 5.5.

In some embodiments, a composition in accordance with the invention has a pH lower than 7 (e.g., a pH of about 5.5) and comprises a salt (e.g., NaCl), typically at a concentration of between 100 mM and 200 mM (e.g., about 150 mM). As observed in the examples, such composition are capable of being nebulized at nebulization output rates greater than 15 ml/h, while maintaining a high encapsulation efficiency post nebulization.

In some embodiments, the buffer (e.g., a phosphate buffer) is present at a concentration of between 1 mM to 20 mM. In specific embodiments, the buffer (e.g., a phosphate buffer such as a sodium phosphate buffer or a potassium phosphate buffer, typically at a pH of 5-6) is present at a concentration of between 1 mM to 10 mM. For example, the buffer may be present at a concentration of 1 mM, 2 mM, 5 mM, 10 mM, 15 mM or 20 mM. In some embodiments, the buffer has a concentration of 10 mM. In some embodiments, the buffer has a concentration of 5 mM. In some embodiments, the buffer has a concentration of 1 mM. In other embodiments, the buffer (e.g., a Tris or imidazole buffer) is present at a concentration of between 40 mM and 100 mM. For example, the buffer may be present at a concentration of 40 mM, 50 mM, 60 mM, 70 mM, 80 mM, 90 mM or 100 mM.

Salt

In some embodiments, the composition further comprises a salt. In some embodiments, the composition comprises (a) an mRNA encapsulated in a lipid nanoparticle, (b) one or more surfactants consisting of an antioxidant moiety covalently linked via a linker moiety to a PEG moiety and (c) a salt, wherein the one or more surfactants is present at a concentration of at least 0.1% weight to volume (w/v).

Exemplary salts that can be used in the compositions of the invention include sodium chloride (NaCl), potassium chloride (KCl), calcium chloride ($CaCl_2$), guanidine chloride and amino acid salts such as arginine chloride. Accordingly, in some embodiments, the salt is sodium chloride. In some embodiments, the salt is potassium chloride. In some embodiments, the salt is calcium chloride.

Sodium chloride has been found to be useful in the composition of the invention to maintain a suitable osmolality. This is based on the mass to charge ratio of sodium chloride which results in a dialectic constant that is particularly suitable for ionization during nebulization. The osmolality of the blood and body fluids is approximately 300 mOsmol/kg. It is advantageous to maintain the osmolality of a composition of the invention such that is either isotonic or hypertonic. Hypotonic solutions that having a lower osmotic pressure than the fluid in the lungs can cause lung irritation. Accordingly, in some embodiments, the osmolality of a composition of the invention is between 250-600 mOsmol/kg, for example 280-400 mOsmol/kg (isotonic to slightly hypertonic) or 500-600 mOsmol/kg (hypertonic).

In some embodiments, the salt has a concentration of between 50 mM to 200 mM. In some embodiments, the salt has a concentration of between 50 mM to 200 mM. In some embodiments, the salt is at a concentration of at least 10 mM, 20 mM, 50 mM or 100 mM. In some embodiments, the salt is at a concentration of 10 mM, 20 mM, 30 mM, 40 mM, 50 mM, 75 mM, 100 mM, 125 mM or 150 mM. The examples demonstrate that it is advantageous to have higher concentrations of salt in the composition, because this improves the rate of nebulization. Therefore, in particular embodiments, the salt is at a concentration of at least 75 mM, 100 mM or 150 mM.

In a typical embodiment, the compositions of the invention comprise a salt (e.g., sodium chloride) in combination with a buffer (e.g., a phosphate buffer). As demonstrated in the examples, the presence of a salt and a buffer in the compositions of the invention improves the nebulisation rates of the composition. Therefore in some embodiments, the composition comprises (a) an mRNA encapsulated in a lipid nanoparticle, (b) one or more surfactants consisting of an antioxidant moiety covalently linked via a linker moiety to a PEG moiety, wherein the one or more surfactants is present at a concentration of at least 0.1% weight to volume (w/v) (c) a salt (e.g., sodium chloride) and (d) a buffer (e.g., a phosphate buffer).

In particular embodiments, a composition in accordance with the present invention comprises a buffer and a salt, e.g., in order to enhance the stability of the composition during storage. In some embodiments, the total concentration of the buffer and the salt is selected from about 40 mM phosphate buffer and about 75-125 mM NaCl, about 50 mM phosphate buffer and about 50 mM-100 mM NaCl, about 100 mM phosphate buffer and about 100 mM-200 mM NaCl, about 40 mM sodium or potassium phosphate and about 100 mM-125 mM NaCl, and about 50 mM sodium or potassium phosphate and 75 mM-100 mM NaCl.

Sugar

In some embodiments, the composition further comprises a sugar. In some embodiments, the composition comprises (a) an mRNA encapsulated in a lipid nanoparticle, (b) one or more surfactants consisting of an antioxidant moiety covalently linked via a linker moiety to a PEG moiety and (c) a sugar, wherein the one or more surfactants is present at a concentration of at least 0.1% weight to volume (w/v). In some embodiments, the sugar is a disaccharide, such as sucrose or trehalose.

In some embodiments, the sugar is present at a concentration of at least 1%, at least 2%, at least 5% or at least 10% (w/v). In some embodiments, the sugar is at a concentration of 1%-20% (w/v). In some embodiments, the sugar is at a concentration of 2-10% (w/v). In particular embodiments, the sugar is at a concentration of 2-6% (w/v). In specific embodiments, the sugar is at a concentration of about 2%, about 4%, about 6%, about 8% or about 10% (w/v). The examples demonstrate that compositions that comprise a lower concentration of sugar have higher nebulization rates. Therefore, a sugar concentration of about 2%, about 4% or about 6% (w/v) has been found to be particularly suitable for the compositions of the invention.

Disaccharides such as trehalose have been found to be particularly suitable excipients for mRNA-lipid nanoparticle compositions, especially because they also can act as lyoprotectant, e.g., during lyophilization. Accordingly, a composition of the invention may comprise trehalose present at a concentration of 2-10% (w/v), e.g., 3-6% (w/v). In particular embodiments, trehalose is present at a concentration of about 2%, about 3%, about 4%, about 6%, about 8% or about 10% (w/v). A trehalose concentration of about 2%, about 3%, about 4% or about 6% (w/v) has been found to be particularly suitable for use with compositions of the invention.

In some embodiments, trehalose can be substituted with sucrose at the same concentration. Accordingly, in some embodiments, a composition of the invention comprises sucrose at a concentration of 2-10% (w/v). In particular embodiments, sucrose is present at a concentration of about 2%, about 3%, about 4%, about 6%, about 8% or about 10% (w/v).

In a typical embodiment, a composition of the invention comprises a surfactant consisting of an antioxidant moiety covalently linked via a linker moiety to a PEG moiety (e.g., TPGS) at a concentration (w/v) of about 0.1-1% in combination with a sugar (e.g., a disaccharide such as trehalose) at a concentration (w/v) of about 3-6%. In combination, the findings in the examples suggest that compositions which comprise one or more surfactants consisting of an antioxidant moiety covalently linked via a linker moiety to a PEG moiety (e.g., TPGS) at a concentration of 0.1%-0.2% (w/v) and a sugar (e.g., a disaccharide such as trehalose) at a concentration of 4-6% (w/v) have particularly improved nebulization rates. Such compositions may further comprise a buffer (e.g., a phosphate buffer) and optionally a salt (e.g., sodium chloride). The buffer may be present at a concentration of 10 mM (e.g., 10 mM sodium phosphate at pH 5.5.). The salt may be present at a concentration of 50 mM to 150 mM. Such compositions are particular suitable for nebulization and can improve nebulization rates.

Other Excipients

In some embodiments, the compositions of the invention also include an excipient selected from a group consisting of DMSO, ethylene glycol, glycerol, 2-Methyl-2,4-pentanediol (MPD), propylene glycol, and combinations thereof.

In some embodiments, the excipient is at a concentration at least 1%, at least 2%, at least 5% or at least 10% w/v. In some embodiments, the excipient is at a concentration of 1%-20% w/v. In some embodiments, the excipient is at a concentration of 2-10% w/v. In some embodiments, the excipient is at a concentration of 2-6% w/v. In some embodiments, the excipient is at a concentration of about 2%, about 4%, about 6%, about 8% or about 10% w/v. In some embodiments, the composition comprises 1%, 2%, 3%, 4%, 5%, 6%, 7%, 8%, 9%, 10%, 11%, 12%, 13%, 14%, 15%, 16%, 17%, 18%, 19% or 20% of the excipient.

Exemplary Compositions of the Invention

In some embodiments, a composition of the invention comprises an mRNA encapsulated in a lipid nanoparticle, TPGS at a concentration (w/v) of about 0.1-1%, and a disaccharide such as trehalose at a concentration (w/v) of about 3-10%. In particular embodiments, a composition of the invention comprises an mRNA encapsulated in a lipid nanoparticle, TPGS at a concentration (w/v) of about 0.5% and trehalose at a concentration (w/v) of about 8%. In particular embodiments, a composition of the invention comprises an mRNA encapsulated in a lipid nanoparticle, TPGS at a concentration (w/v) of about 0.1%-0.3% in combination with trehalose at a concentration (w/v) of about 3-6%.

In some embodiments, a composition of the invention comprises an mRNA encapsulated in a lipid nanoparticle, TPGS at a concentration (w/v) of about 0.1-1% and sodium chloride. In particular embodiments, a composition of the invention comprises an mRNA encapsulated in a lipid nanoparticle, TPGS at a concentration (w/v) of about 0.1-1% and sodium chloride at a concentration of at least 75 mM (e.g. about 75 mM to 200 mM).

In some embodiments, a composition of the invention comprises an mRNA encapsulated in a lipid nanoparticle, TPGS at a concentration (w/v) of about 0.1-1%, sodium chloride and a phosphate buffer. In particular embodiments, a composition of the invention comprises an mRNA encapsulated in a lipid nanoparticle, TPGS at a concentration (w/v) of about 0.1-1%, sodium chloride at a concentration of at least 50 mM (e.g. about 50 mM to 200 mM) and a phosphate buffer with a pH of about 5.5.

Messenger RNA (mRNA)

The compositions of the invention comprise any mRNA encapsulated in a lipid nanoparticle. mRNA is typically thought of as the type of RNA that carries information from DNA to the ribosome. Typically, in eukaryotic organisms, mRNA processing comprises the addition of a "cap" on the 5' end, and a "tail" on the 3' end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The additional of a tail is typically a polyadenylation event whereby a polyadenylyl moiety is added to the 3' end of the mRNA molecule. The presence of this "tail" serves to protect the mRNA from exonuclease degradation. mRNA is translated by the ribosomes into a series of amino acids that make up a protein.

In some embodiments, a composition in accordance with the invention comprises an mRNA encapsulated in the lipid nanoparticle, wherein the mRNA is present in the composition at a concentration ranging from about 0.5 mg/mL to about 1.0 mg/mL. In some embodiments, the mRNA is present at a concentration of at least 0.5 mg/mL. In some embodiments, the mRNA is present at a concentration of at least 0.6 mg/mL. In some embodiments, the mRNA is present at a concentration of at least 0.7 mg/mL. In some embodiments, the mRNA is present at a concentration of at least 0.8 mg/mL. In some embodiments, the mRNA is present at a concentration of at least 0.9 mg/mL. In some embodiments, the mRNA is present at a concentration of at least 1.0 mg/mL. In a typical embodiment, the mRNA is present at a concentration of about 0.6 mg/mL to about 0.8 mg/mL.

mRNA Encoding a Therapeutic Protein

In certain embodiments, the encapsulated mRNA encodes a therapeutic protein. The term "therapeutic protein" as used herein may refer to a protein, polypeptide or peptide. In a typical embodiment, a therapeutic protein is an enzyme, a membrane protein, an antibody or an antigen.

In some embodiments, the encapsulated mRNA encodes for cystic fibrosis transmembrane conductance regulator (CFTR), ATP-binding cassette sub-family A member 3 protein, dynein axonemal intermediate chain 1 (DNAI1) protein, dynein axonemal heavy chain 5 (DNAH5) protein, alpha-1-antitrypsin protein, forkhead box P3 (FOXP3) protein, or a surfactant protein, e.g., surfactant A protein, surfactant B protein, surfactant C protein, and surfactant D protein.

In certain embodiments, the encapsulated mRNA encodes an antigen. In certain embodiments, the encapsulated mRNA encodes an antigen associated with a cancer of a subject or identified from a cancer cell of a subject. In certain embodiments, the encapsulated mRNA encodes an antigen determined from a subject's own cancer cell (e.g., a tumour neoantigen), i.e., to provide a personalized cancer vaccine.

In certain embodiments, the encapsulated mRNA encodes an antibody. In certain embodiments, the antibody can be a bi-specific antibody. In certain embodiments, the antibody can be part of a fusion protein. In certain embodiments, the codon optimized mRNA encapsulated in such lipid nanoparticle encodes for an antibody to OX40. In certain embodiments, the codon optimized mRNA encapsulated in such lipid nanoparticle encodes for an antibody to VEGF. In certain embodiments, the encapsulated mRNA encodes an antibody to tissue necrosis factor alpha. In certain embodiments, the encapsulated mRNA encodes an antibody to CD3. In certain embodiments, the encapsulated mRNA encodes an antibody to CD19.

In certain embodiments, the encapsulated mRNA encodes an immunomodulator. In certain embodiments, the encapsulated mRNA encodes Interleukin 12. In certain embodiments, the encapsulated mRNA encodes Interleukin 23. In certain embodiments, the encapsulated mRNA encodes Interleukin 36 gamma. In certain embodiments, the encapsulated mRNA encodes a constitutively active variant of one or more stimulator of interferon genes (STING) proteins.

In certain embodiments, the encapsulated mRNA encodes an endonuclease. In certain embodiments, the encapsulated mRNA encodes an RNA-guided DNA endonuclease protein, such as Cas 9 protein. In certain embodiments, the encapsulated mRNA encodes meganuclease protein. In certain embodiments, the encapsulated mRNA encodes a transcription activator-like effector nuclease protein. In certain embodiments, the encapsulated mRNA encodes a zinc finger nuclease protein.

Typically, mRNA encapsulated in a lipid nanoparticle in the compositions of the invention comprises a poly-A tail. In some embodiments, the mRNA comprises a poly-A tail of at least 70 residues in length. In some embodiments, the mRNA comprises a poly-A tail of at least 100 residues in length. In some embodiments, the mRNA comprises a poly-A tail of at least 120 residues in length. In some embodiments, the mRNA comprises a poly-A tail of at least 150 residues in length. In some embodiments, the mRNA comprises a poly-A tail of at least 200 residues in length. In some embodiments, the mRNA comprises a poly-A tail of at least 250 residues in length.

mRNA Synthesis mRNAs may be synthesized according to any of a variety of known methods. Various methods are described in published U.S. Application No. US 2018/0258423, and can be used to practice the present invention, all of which are incorporated herein by reference. For example, mRNAs for use with the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application. In some embodiments, mRNA may be further purified for use with the present invention. In some embodiments, in vitro synthesized mRNA may be purified before formulation and encapsulation to remove undesirable impurities including various enzymes and other reagents used during mRNA synthesis.

Various methods may be used to purify mRNA for use with the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol:chloroform:isoamyl alcohol solution, well known to one of skill in the art.

In particular embodiments, the mRNA is purified using Tangential Flow Filtration (TFF). Suitable purification methods include those described in published U.S. Application No. US 2016/0040154, published U.S. Application No. US 2015/0376220, published U.S. Application No. US 2018/0251755, published U.S. Application No. US 2018/0251754, U.S. Provisional Application No. 62/757,612 filed on Nov. 8, 2018, and U.S. Provisional Application No. 62/891,781 filed on Aug. 26, 2019, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing. In some embodiments, the mRNA is purified either before or after or both before and after capping and tailing, by centrifugation. In some embodiments, the mRNA is purified either before or after or both before and after capping and tailing, by filtration. In some embodiments, the mRNA is purified either before or after or both before and after capping and tailing, by TFF. In some embodiments, the mRNA is purified either before or after or both before and after capping and tailing by chromatography.

Various naturally-occurring or modified nucleosides may be used to produce an mRNA for use with the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("ΨU"), and/or 2-thio-uridine ("2sU"). See, e.g., U.S. Pat. No. 8,278,036 or WO 2011/012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO 2011/012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

The encapsulated mRNAs may vary in length. In some embodiments, the encapsulated in vitro synthesized mRNA may have a length of or greater than about 0.5 kb, 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, 20 kb, 30 kb, 40 kb, or 50 kb in length. In some embodiments, the encapsulated in vitro synthesized mRNA ranges from about 1-20 kb, about 1-15 kb, about 1-10 kb, about 5-20 kb, about 5-15 kb, about 5-12 kb, about 5-10 kb, about 8-20 kb, about 8-15 kb, or about 8-50 kb in length.

Codon Optimized mRNA

In some embodiments, the compositions of the present invention are for delivering codon optimized mRNA encoding a therapeutic protein to a subject for the treatment of a disease. A suitable codon optimized mRNA encodes any full length, fragment or portion of a protein which can be substituted for naturally-occurring protein activity and/or reduce the intensity, severity, and/or frequency of one or more symptoms associated with the disease.

Generation of Optimized Nucleotide Sequences

The compositions of the present invention may comprise encapsulated mRNAs that comprise optimized nucleotide sequence encoding a therapeutic protein. These mRNAs are modified relative to their naturally occurring counterparts to (a) improve the yield of full-length mRNAs during in vitro synthesis, and (b) to maximize expression of the encoded polypeptide after delivery of the mRNA to a target cell in vivo. Sequence motifs that favour rapid degradation of the mRNA in the target cell have also been removed.

An exemplary process for generating optimized nucleotide sequences for mRNA encapsulated by a lipid nanoparticle for use in the compositions of the present invention first generates a list of codon-optimized sequences and then applies three filters to the list. Specifically, it applies a motif screen filter, guanine-cytosine (GC) content analysis filter, and codon adaptation index (CAI) analysis filter to produce an updated list of optimized nucleotide sequences. The updated list no longer includes nucleotide sequences containing features that are expected to interfere with effective transcription and/or translation of the encoded polypeptide.

Codon Optimization

The genetic code has 64 possible codons. Each codon comprises a sequence of three nucleotides. The usage frequency for each codon in the protein-coding regions of the genome can be calculated by determining the number of instances that a specific codon appears within the protein-coding regions of the genome, and subsequently dividing the obtained value by the total number of codons that encode the same amino acid within protein-coding regions of the genome.

A codon usage table contains experimentally derived data regarding how often, for the particular biological source from which the table has been generated, each codon is used to encode a certain amino acid. This information is expressed, for each codon, as a percentage (0 to 100%), or fraction (0 to 1), of how often that codon is used to encode a certain amino acid relative to the total number of times a codon encodes that amino acid.

Codon usage tables are stored in publically available databases, such as the Codon Usage Database (Nakamura et al. (2000) Nucleic Acids Research 28(1), 292; available online at https://www.kazusa.or.jp/codon/), and the High-performance Integrated Virtual Environment-Codon Usage Tables (HIVE-CUTs) database (Athey et al., (2017), BMC Bioinformatics 18(1), 391; available online at http://hive.biochemistry.gwu.edu/review/codon).

During the first step of codon optimization, codons are removed from a first codon usage table which reflects the frequency of each codon in a given organism (e.g., a mammal or human) if they are associated with a codon usage frequency which is less than a threshold frequency (e.g., 10%). The codon usage frequencies of the codons not removed in the first step are normalized to generate a normalized codon usage table. An optimized nucleotide sequence encoding an amino acid sequence of interest is generated by selecting a codon for each amino acid in the amino acid sequence based on the usage frequency of the one or more codons associated with a given amino acid in the normalized codon usage table. The probability of selecting a certain codon for a given amino acid is equal to the usage frequency associated with the codon associated with this amino acid in the normalized codon usage table.

The codon-optimized sequences of the mRNA encapsulated by the lipid nanoparticle are generated by a computer-implemented method for generating an optimized nucleotide sequence. The method comprises: (i) receiving an amino acid sequence, wherein the amino acid sequence encodes a peptide, polypeptide, or protein; (ii) receiving a first codon usage table, wherein the first codon usage table comprises a list of amino acids, wherein each amino acid in the table is associated with at least one codon and each codon is associated with a usage frequency; (iii) removing from the codon usage table any codons associated with a usage frequency which is less than a threshold frequency; (iv) generating a normalized codon usage table by normalizing the usage frequencies of the codons not removed in step (iii); and (v) generating an optimized nucleotide sequence encoding the amino acid sequence by selecting a codon for each amino acid in the amino acid sequence based on the usage frequency of the one or more codons associated with the amino acid in the normalized codon usage table. The threshold frequency can be in the range of 5%-30%, in particular 5%, 10%, 15%, 20%, 25%, or 30%. In the context of the present invention, the threshold frequency is typically 10%.

The step of generating a normalized codon usage table comprises: (a) distributing the usage frequency of each codon associated with a first amino acid and removed in step (iii) to the remaining codons associated with the first amino acid; and (b) repeating step (a) for each amino acid to produce a normalized codon usage table. In some embodiments, the usage frequency of the removed codons is distributed equally amongst the remaining codons. In some embodiments, the usage frequency of the removed codons is distributed amongst the remaining codons proportionally based on the usage frequency of each remaining codon. “Distributed” in this context may be defined as taking the combined magnitude of the usage frequencies of removed codons associated with a certain amino acid and apportioning some of this combined frequency to each of the remaining codons encoding the certain amino acid.

The step of selecting a codon for each amino acid comprises: (a) identifying, in the normalized codon usage table, the one or more codons associated with a first amino acid of the amino acid sequence; (b) selecting a codon associated with the first amino acid, wherein the probability of selecting a certain codon is equal to the usage frequency associated with the codon associated with the first amino acid in the normalized codon usage table; and (c) repeating steps (a) and (b) until a codon has been selected for each amino acid in the amino acid sequence.

The step of generating an optimized nucleotide sequence by selecting a codon for each amino acid in the amino acid sequence (step (v) in the above method) is performed n times to generate a list of optimized nucleotide sequences.

Motif Screen

A motif screen filter is applied to the list of optimized nucleotide sequences. Optimized nucleotide sequences encoding any known negative cis-regulatory elements and negative repeat elements are removed from the list to generate an updated list.

For each optimized nucleotide sequence in the list, it is also determined whether it contains a termination signal. Any nucleotide sequence that contains one or more termination signals is removed from the list generating an updated list. In some embodiments, the termination signal has the following nucleotide sequence: 5'-X1ATCTX2TX3-3', wherein X1, X2 and X3 are independently selected from A, C, T or G. In some embodiments, the termination signal has one of the following nucleotide sequences: TATCTGTT; and/or TTTTTT; and/or AAGCTT; and/or GAAGAGC; and/or TCTAGA. In a typical embodiment, the termination signal has the following nucleotide sequence: 5'-X1AUCUX2UX3-3', wherein X1, X2 and X3 are independently selected from A, C, U or G. In a specific embodiment, the termination signal has one of the following nucleotide sequences: UAUCUGUU; and/or UUUUUU; and/or AAGCUU; and/or GAAGAGC; and/or UCUAGA.

Guanine-Cytosine (GC) Content

The method further comprises determining a guanine-cytosine (GC) content of each of the optimized nucleotide sequences in the updated list of optimized nucleotide sequences. The GC content of a sequence is the percentage of bases in the nucleotide sequence that are guanine or cytosine. The list of optimized nucleotide sequences is further updated by removing any nucleotide sequence from the list, if its GC content falls outside a predetermined GC content range.

Determining a GC content of each of the optimized nucleotide sequences comprises, for each nucleotide sequence: determining a GC content of one or more additional portions of the nucleotide sequence, wherein the additional portions are non-overlapping with each other and with the first portion, and wherein updating the list of optimized sequences comprises: removing the nucleotide sequence if the GC content of any portion falls outside the predetermined GC content range, optionally wherein determining the GC content of the nucleotide sequence is halted when the GC content of any portion is determined to be outside the predetermined GC content range. In some embodiments, the first portion and/or the one or more additional portions of the nucleotide sequence comprise a predetermined number of nucleotides, optionally wherein the predetermined number of nucleotides is in the range of: 5 to 300 nucleotides, or 10 to 200 nucleotides, or 15 to 100 nucleotides, or 20 to 50 nucleotides. In the context of the present invention, the predetermined number of nucleotides is typically 30 nucleotides. The predetermined GC content range can be 15%-75%, or 40%-60%, or, 30%-70%. In the context of the present invention, the predetermined GC content range is typically 30%-70%.

A suitable GC content filter in the context of the invention may first analyze the first 30 nucleotides of the optimized nucleotide sequence, i.e., nucleotides 1 to 30 of the optimized nucleotide sequence. Analysis may comprise determining the number of nucleotides in the portion with are either G or C, and determining the GC content of the portion may comprise dividing the number of G or C nucleotides in the portion by the total number of nucleotides in the portion. The result of this analysis will provide a value describing the proportion of nucleotides in the portion that are G or C, and may be a percentage, for example 50%, or a decimal, for example 0.5. If the GC content of the first portion falls outside a predetermined GC content range, the optimized nucleotide sequence may be removed from the list of optimized nucleotide sequences.

If the GC content of the first portion falls inside the predetermined GC content range, the GC content filter may then analyze a second portion of the optimized nucleotide sequence. In this example, this may be the second 30 nucleotides, i.e., nucleotides 31 to 60, of the optimized nucleotide sequence. The portion analysis may be repeated for each portion until either: a portion is found having a GC content falling outside the predetermined GC content range, in which case the optimized nucleotide sequence may be removed from the list, or the whole optimized nucleotide sequence has been analyzed and no such portion has been found, in which case the GC content filter retains the optimized nucleotide sequence in the list and may move on to the next optimized nucleotide sequence in the list.

Codon Adaptation Index (CAI)

The method further comprises determining a codon adaptation index of each of the optimized nucleotide sequences in the most recently updated list of optimized nucleotide sequences. The codon adaptation index of a sequence is a measure of codon usage bias and can be a value between 0 and 1. The most recently updated list of optimized nucleotide sequences is further updated by removing any nucleotide sequence if its codon adaptation index is less than or equal to a predetermined codon adaptation index threshold. The codon adaptation index threshold can 0.7, or 0.75, or 0.8, or 0.85, or 0.9. The inventors have found that optimized nucleotide sequences with a codon adaptation index equal to or greater than 0.8 deliver very high protein yield. Therefore in the context of the invention, the codon adaptation index threshold is typically 0.8.

A codon adaptation index may be calculated, for each optimized nucleotide sequence, in any way that would be apparent to a person skilled in the art, for example as described in "The codon adaptation index-a measure of directional synonymous codon usage bias, and its potential applications" (Sharp and Li, 1987. Nucleic Acids Research 15(3), p. 1281-1295); available online at https://www.ncbi.nlm.nih.gov/pmc/articles/PMC340524/.

Implementing a codon adaptation index calculation may include a method according to, or similar to, the following. For each amino acid in a sequence, a weight of each codon in a sequence may be represented by a parameter termed relative adaptiveness (wi). Relative adaptiveness may be computed from a reference sequence set, as the ratio between the observed frequency of the codon fi and the frequency of the most frequent synonymous codon fj for that amino acid. The codon adaptation index of a sequence may then be calculated as the geometric mean of the weight associated to each codon over the length of the sequence (measured in codons). The reference sequence set used to calculate a codon adaptation index may be the same reference sequence set from which a codon usage table used with the codon optimization methods described herein is derived.

Lipid Nanoparticle

The compositions of the present invention comprise mRNA encapsulated in a lipid nanoparticle. In the context of the present invention, a lipid nanoparticle typically serves to transport a desired mRNA to a target cell or tissue. Typically, the lipid nanoparticle comprises a cationic lipid, a non-cationic lipid (DOPE or DSPC) and a PEG-modified lipid (e.g., DMG-PEG2K), and optionally a cholesterol-based lipids (e.g., cholesterol, β-sitosterol or stigmastanol). For example, the lipid nanoparticle may comprise a lipid component consisting of (i) a cationic lipid, (ii) a non-cationic lipid, (iii) a PEG-modified lipid, and (iv) cholesterol or a cholesterol analogue (e.g., β-sitosterol or stigmastanol). In some embodiments, a lipid nanoparticle comprises no more than three distinct lipid components. In some embodiments, one distinct lipid component is a sterol-based cationic lipid (e.g., Guan-SS-Chol). In some embodiments, the no more than three distinct lipid components are a cationic lipid (e.g., a sterol-based cationic lipid such as Guan-SS-Chol), a non-cationic lipid (e.g., DOPE) and a PEG-modified lipid (e.g., DMG-PEG2K).

nent consisting of the following lipids with molar ratios of: a) 41%-70% of a cationic lipid, b) 9%-18% of a non-cationic lipid, c) 2%-6% of a PEG-modified lipid, and d) 9%-48% of cholesterol or a cholesterol analogue. In one specific embodiment, the molar ratios of the lipids in a lipid nanoparticle in accordance with the invention are: a. 50%-60% cationic lipid, b. 9%-18% non-cationic lipid, c. 4%-6% PEG-modified lipid, and d. 20-35% cholesterol or cholesterol analogue. In another specific embodiment, the molar ratios of the lipids in a lipid nanoparticle in accordance with the invention are: a. 50%-60% cationic lipid, b. 9%-15% non-cationic lipid, c. 4%-6% PEG-modified lipid, and d. 25-30% cholesterol or cholesterol analogue.

As used herein, the molar ratios of the lipids of the lipid nanoparticle sum to 100%. For example, for a lipid nanoparticle comprising a lipid component consisting of the following lipids with molar ratios of: a) 41%-70% of a cationic lipid, b) 9%-18% of a non-cationic lipid, c) 2%-6% of a PEG-modified lipid, and d) 9%-48% of cholesterol or a cholesterol analogue, if the molar ratio of the cationic lipid is 70%, the molar ratio of the non-cationic lipid may be 9% and the molar ratio of the PEG-modified lipid may be 2%, then the molar ratio of the cholesterol or a cholesterol analogue may be 19% (70%+9%+2%+19%=100%).

In some embodiments, where the molar ratio is defined as a range, e.g. 2%-6% of a PEG-modified lipid, the limits of the range are the exact values specified. For example, the lower limit 2% of the molar ratio 2%-6% for the PEG-modified lipid is 2%.

Cationic Lipid

As used herein, the term "cationic lipid" refers to an ionizable lipid that has a net positive charge at a pH lower than at a physiological pH (e.g., about pH 5.5, about 6.0, or about 6.5).

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

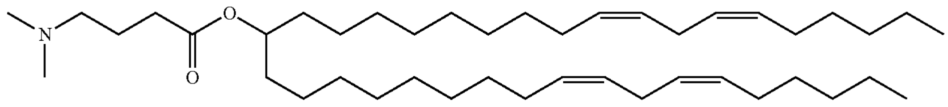 [SMILES: CCCCC/C=C\C/C=C\CCCCCCCCC(CCCCCCCC/C=C\C/C=C\CCCCC)OC(=O)CCCN(C)C]

Molar Ratios

In some embodiments, a lipid nanoparticle in a composition of the invention comprises a lipid component consisting of the following lipids with molar ratios of: a) 30%-60% of a cationic lipid, b) 25%-35% of a non-cationic lipid, c) 1%-15% of a PEG-modified lipid, and d) 20%-30% of cholesterol or a cholesterol analogue.

mRNA encapsulating lipid nanoparticles with a lipid component consisting of a cationic lipid, a non-cationic lipid, a PEG-modified lipid and a cholesterol or cholesterol analogue may be more effective for pulmonary administration by nebulization when a lower molar ratio of the non-cationic lipid is used than is typically present in lipid nanoparticles delivered via this route of administration. Accordingly, in some embodiments, a lipid nanoparticle in a composition of the invention comprising a lipid compo- and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

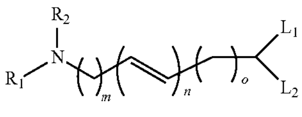

,

-continued

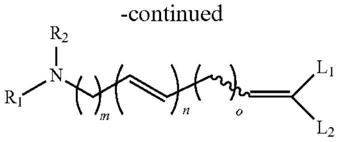

or a pharmaceutically acceptable salt thereof, wherein R1 and R2 are each independently selected from the group consisting of hydrogen, an optionally substituted, variably saturated or unsaturated C1-C20 alkyl and an optionally substituted, variably saturated or unsaturated C6-C20 acyl; wherein L1 and L2 are each independently selected from the group consisting of hydrogen, an optionally substituted C1-C30 alkyl, an optionally substituted variably unsaturated C1-C30 alkenyl, and an optionally substituted C1-C30 alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z,18Z)—N,N-dimethyl-6-(9Z,12Z)-octadeca-9,12-dien-1-yl) tetracosa-15,18-dien-1-amine ("HGT5000"), having a compound structure of:

(HGT-5000)

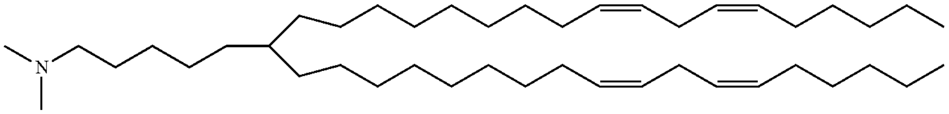

and pharmaceutically acceptable salts thereof. In certain embodiments, the compositions and methods of the present invention include the cationic lipid (15Z,18Z)—N,N-dimethyl-6-((9Z,12Z)-octadeca-9,12-dien-1-yl) tetracosa-4,15,18-trien-1-amine ("HGT5001"), having a compound structure of:

(HGT-5001)

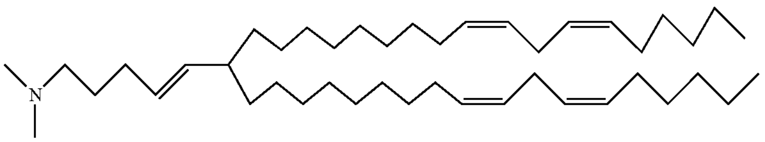

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

(HGT-5002)

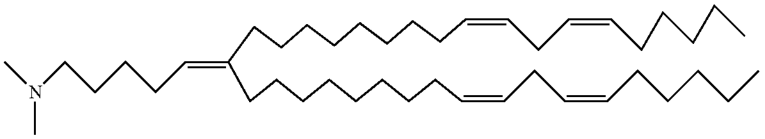

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

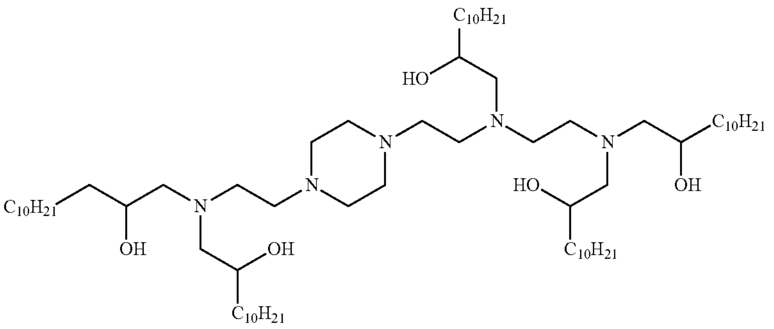

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

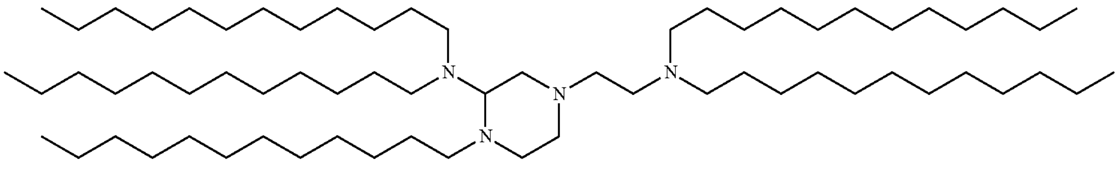 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

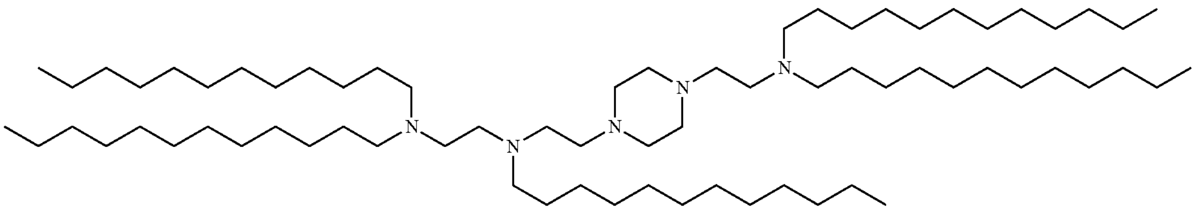 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

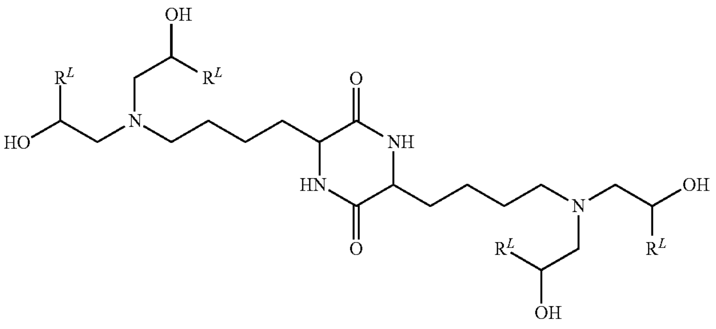

or pharmaceutically acceptable salts thereof, wherein each instance of RL is independently optionally substituted C6-C40 alkenyl. In certain embodiments, the compositions and methods of the present invention include a cationic lipid having a compound structure of:

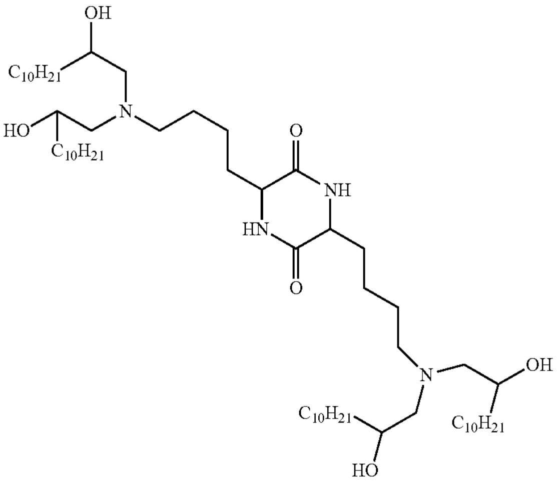

and pharmaceutically acceptable salts thereof. In certain embodiments, the compositions and methods of the present invention include a cationic lipid having a compound structure of:

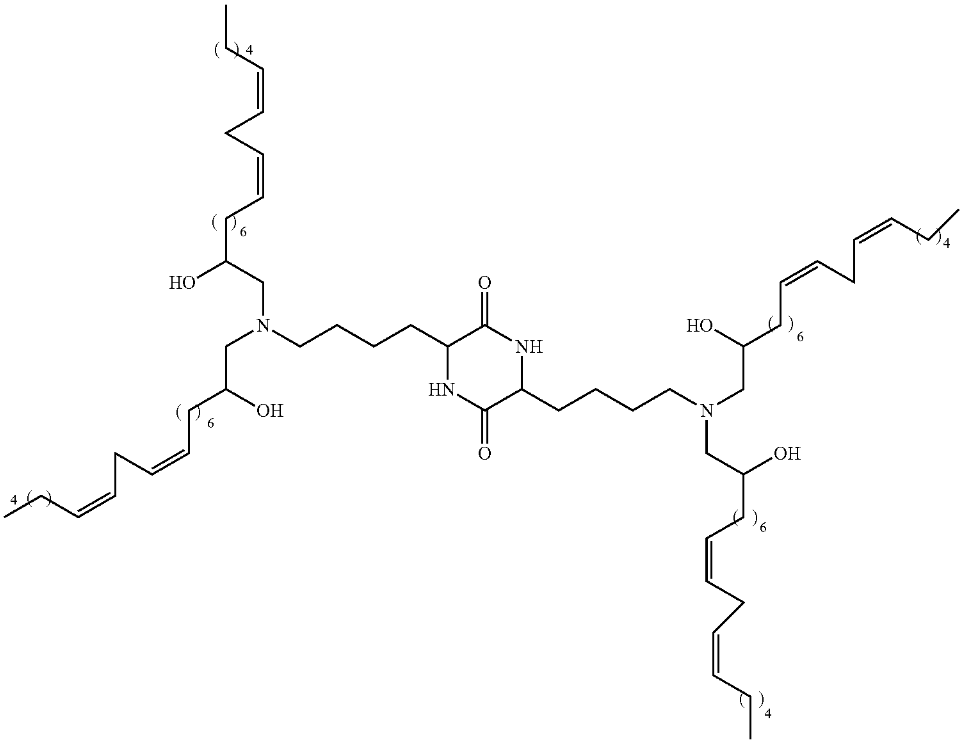

and pharmaceutically acceptable salts thereof. In certain embodiments, the compositions and methods of the present invention include a cationic lipid having a compound structure of:

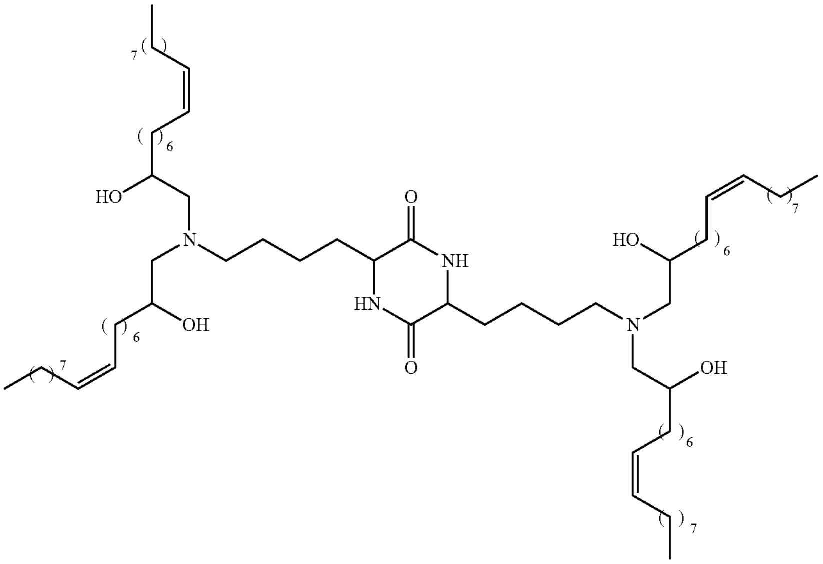

and pharmaceutically acceptable salts thereof. In certain embodiments, the compositions and methods of the present invention include a cationic lipid having a compound structure of:

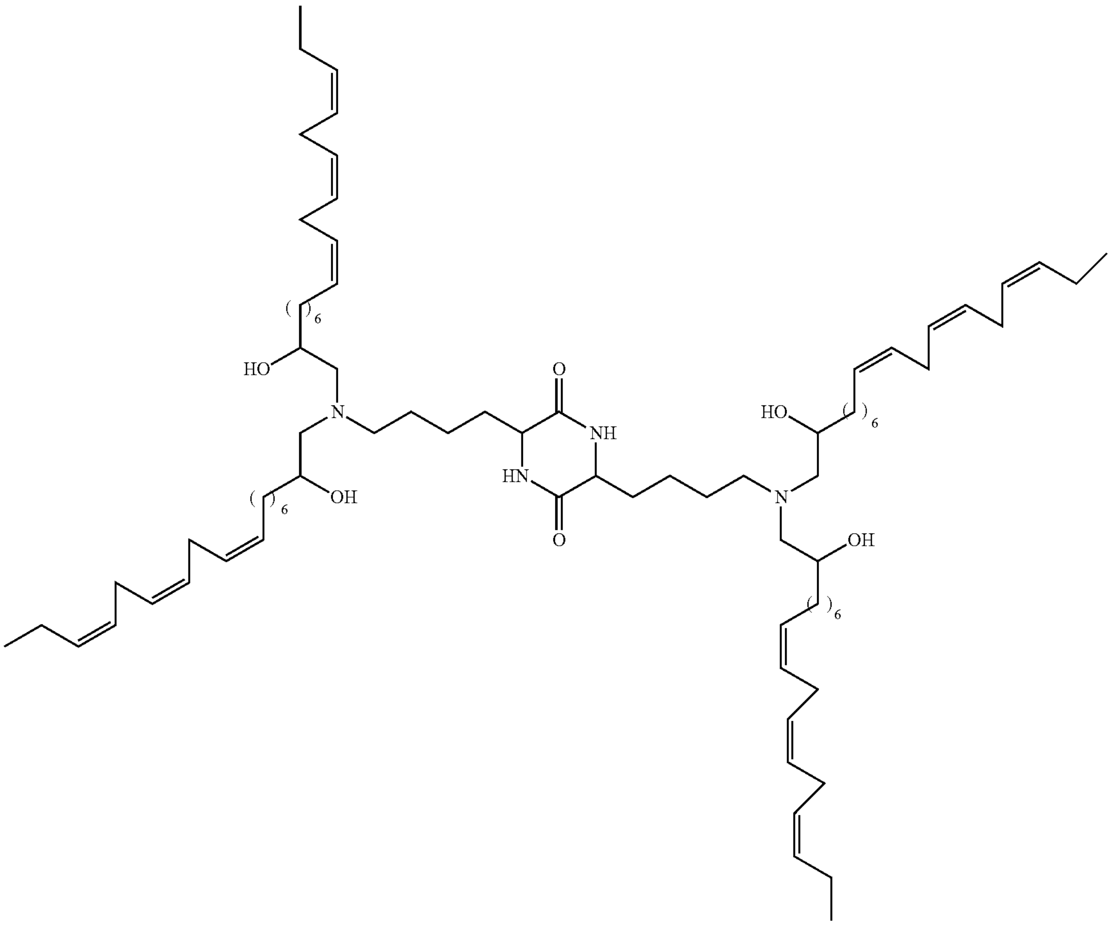

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

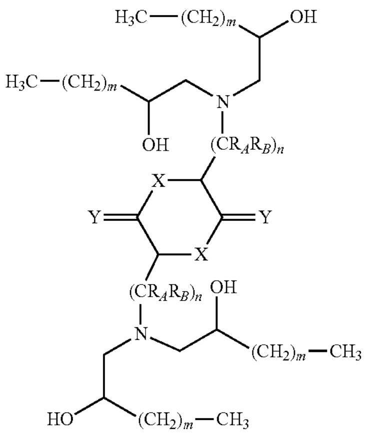

or a pharmaceutically acceptable salt thereof, wherein each X independently is O or S; each Y independently is O or S; each m independently is 0 to 20; each n independently is 1 to 6; each RA is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each RB is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, “Target 23”, having a compound structure of:

(Target 23)

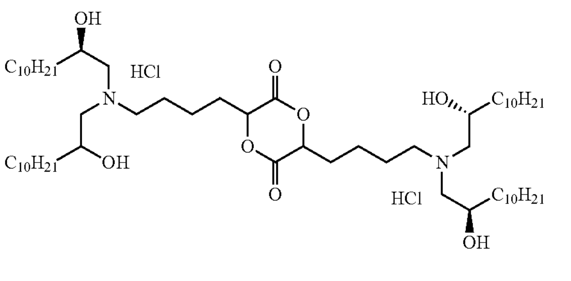

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

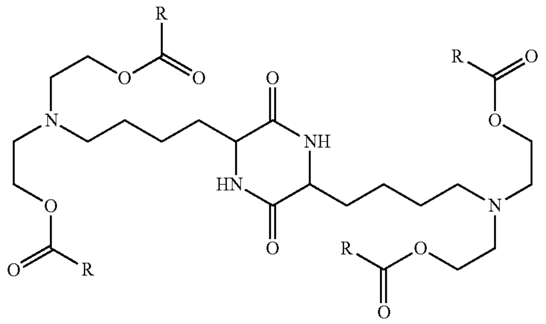

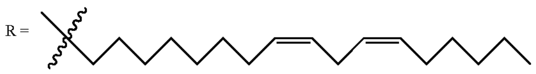

or a pharmaceutically acceptable salt thereof. In some embodiments, the compositions and methods of the present invention include a cationic lipid having the compound structure:

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

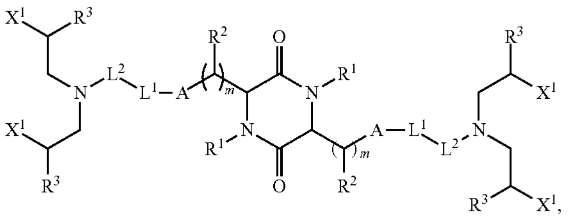

or a pharmaceutically acceptable salt thereof, wherein each R1 and R2 is independently H or C1-C6 aliphatic; each m is independently an integer having a value of 1 to 4; each A is independently a covalent bond or arylene; each L1 is independently an ester, thioester, disulfide, or anhydride group; each L2 is independently C2-C10 aliphatic; each X1 is independently H or OH; and each R3 is independently C6-C20 aliphatic. In some embodiments, the compositions and methods of the present invention include a cationic lipid of the following formula:

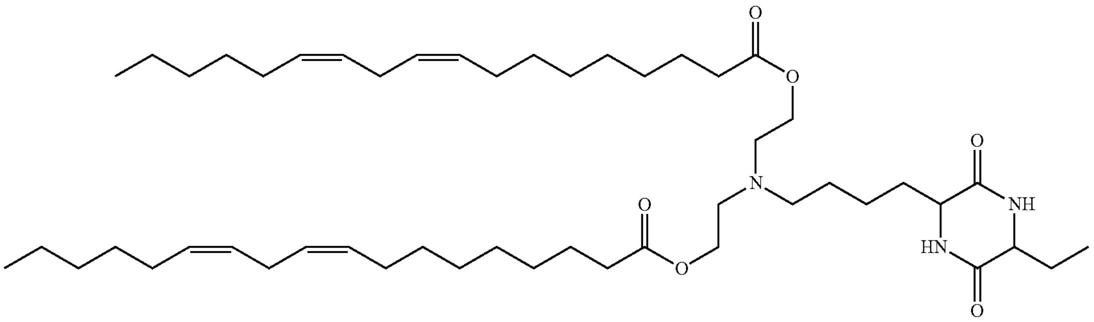 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

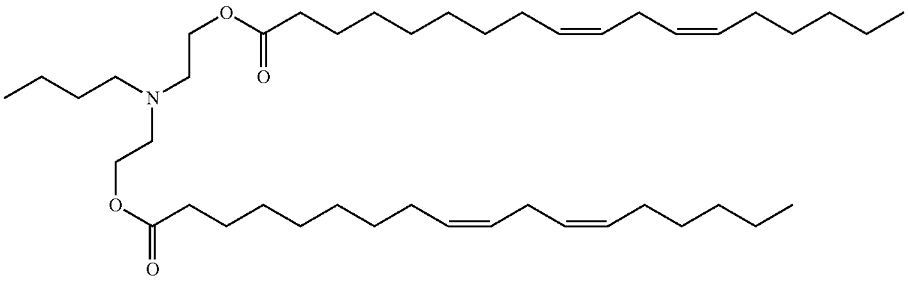 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

(Compound 1)

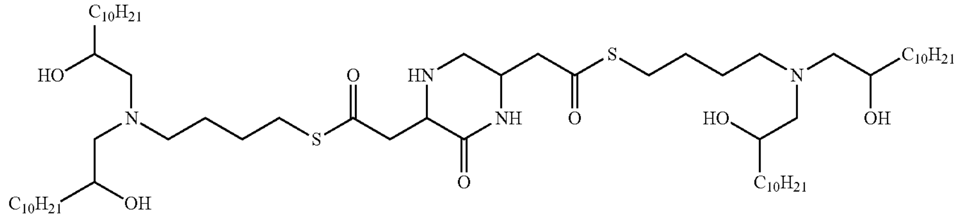

or a pharmaceutically acceptable salt thereof. In some embodiments, the compositions and methods of the present invention include a cationic lipid of the following formula:

(Compund 2)

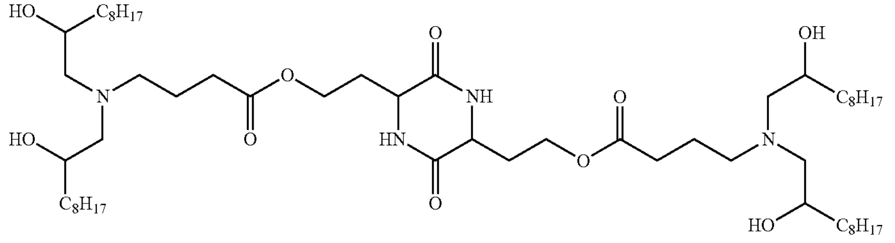

or a pharmaceutically acceptable salt thereof. In some embodiments, the compositions and methods of the present invention include a cationic lipid of the following formula:

(Compund 3)

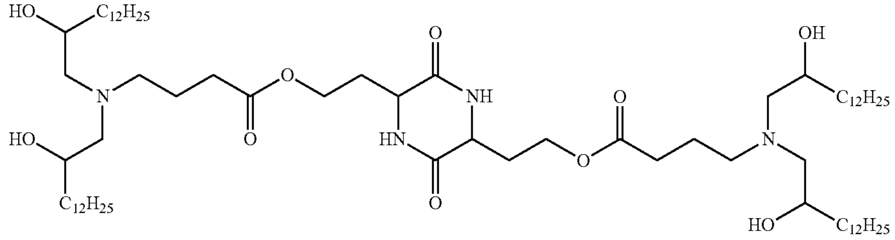

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

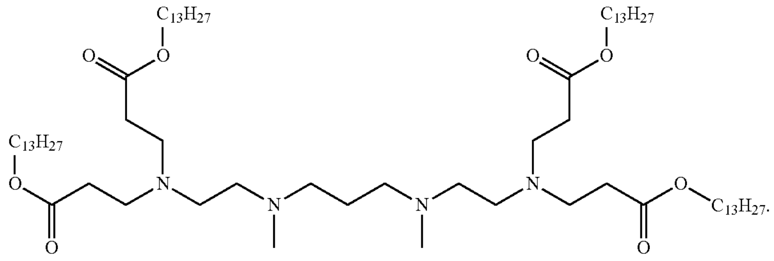

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

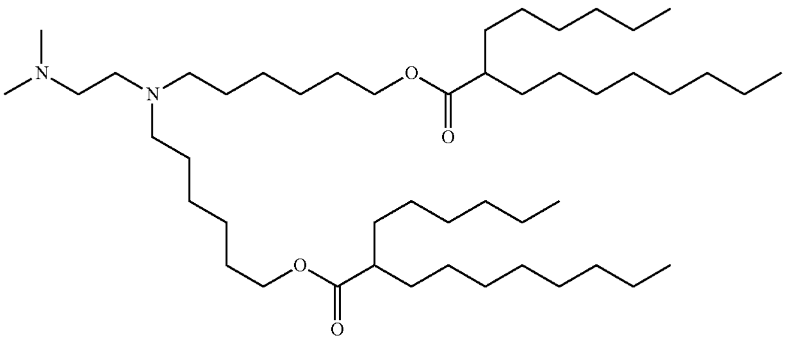 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

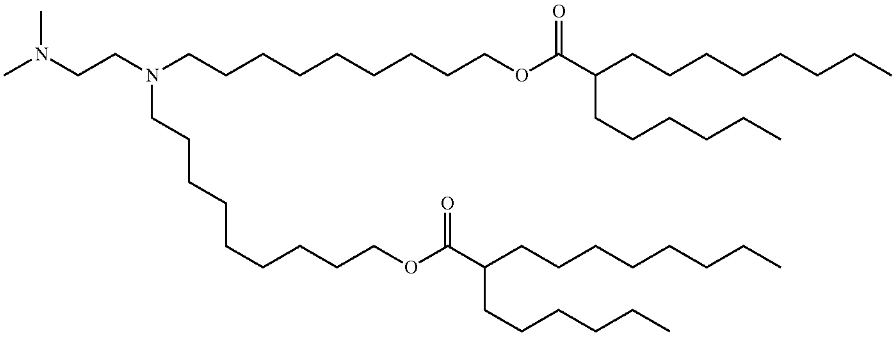 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

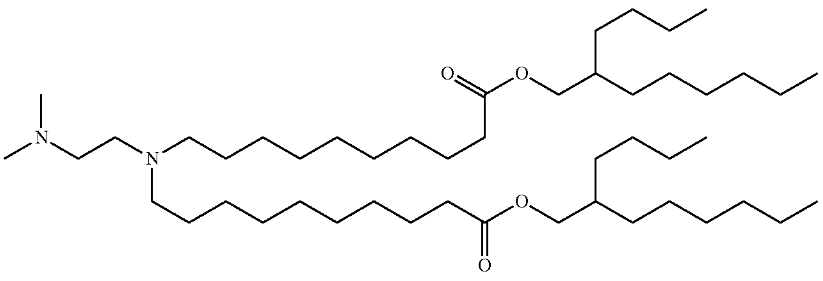 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

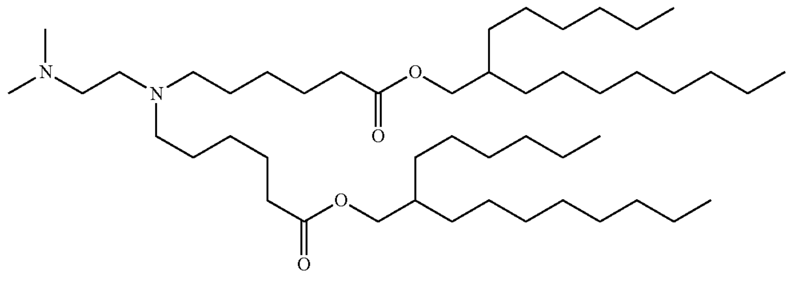 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

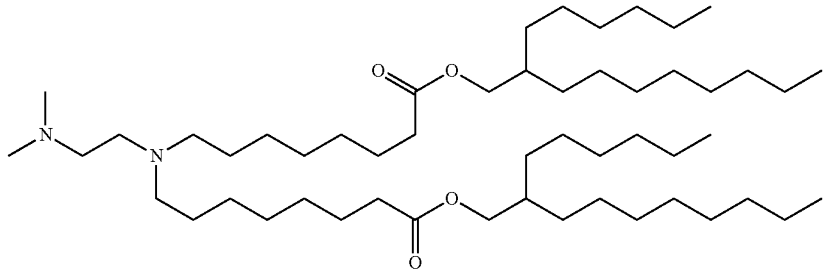 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

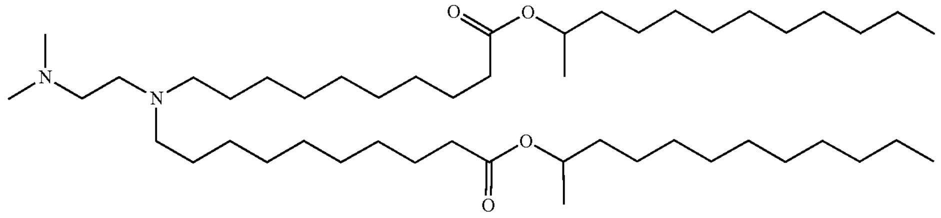 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

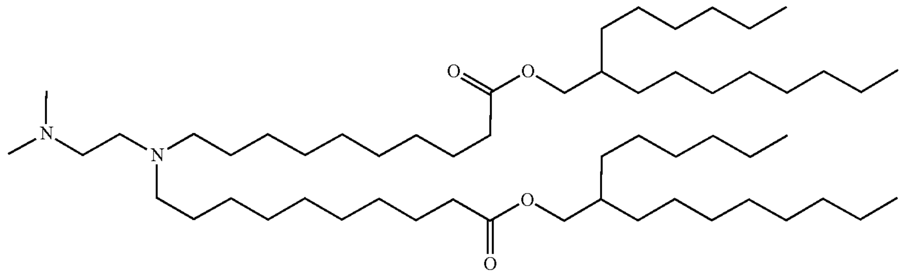 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

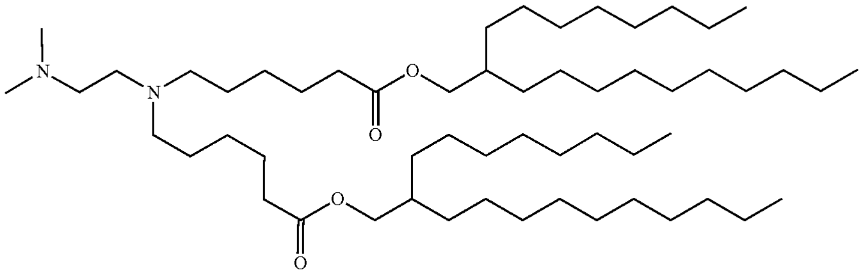 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

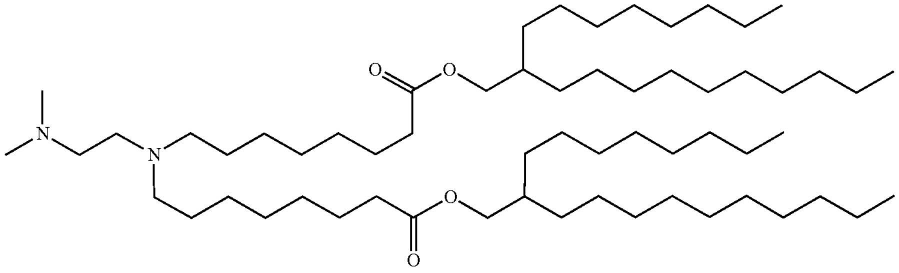 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

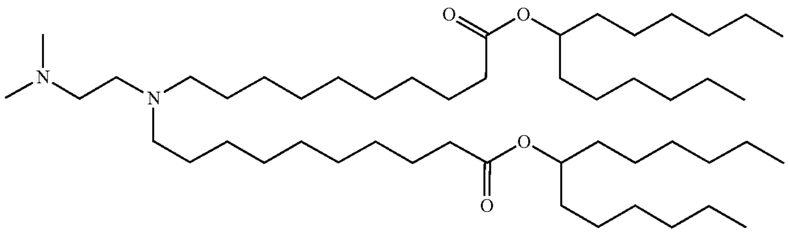 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

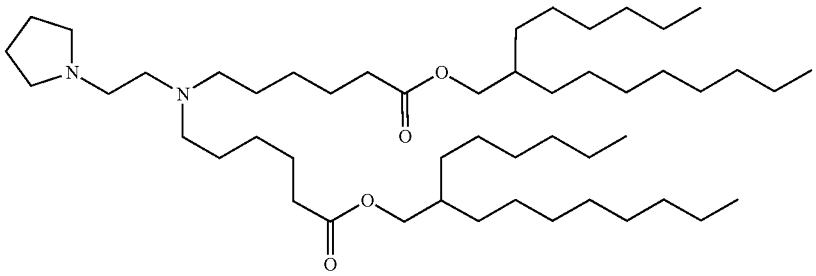 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

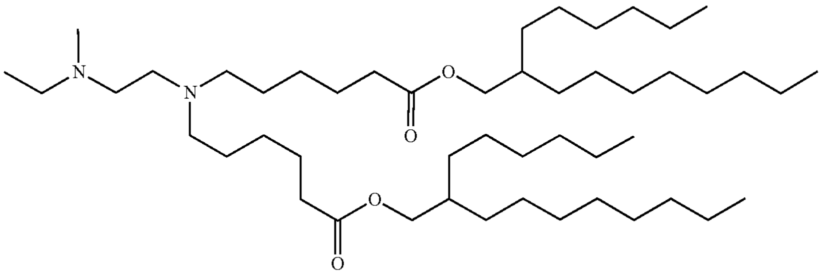 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

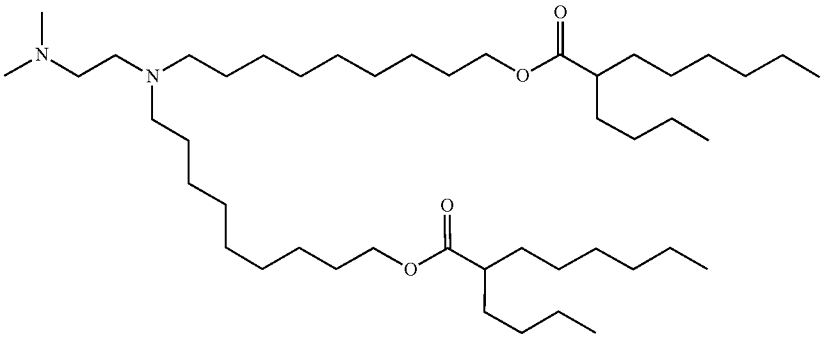 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

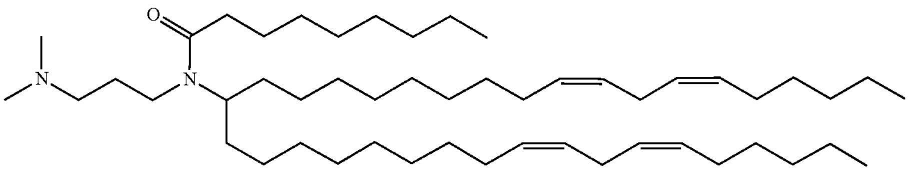 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

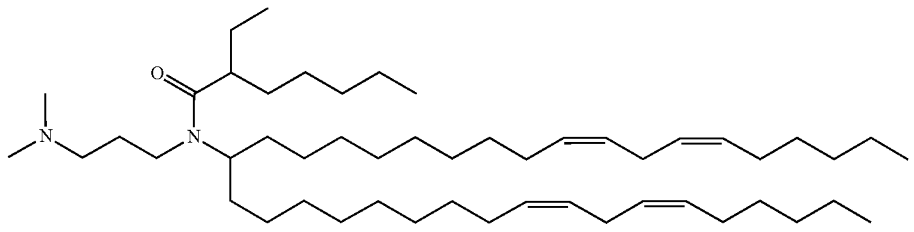 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

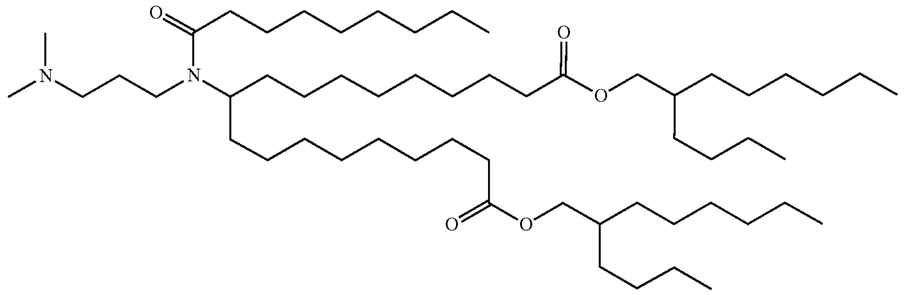 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

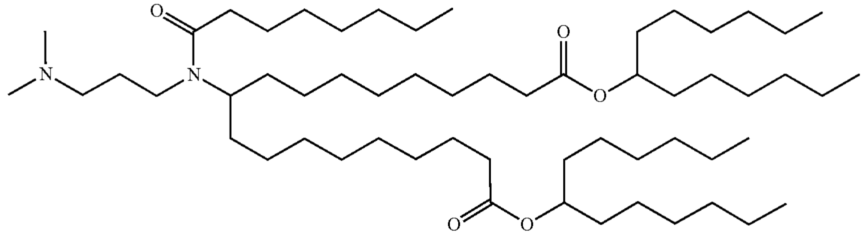 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

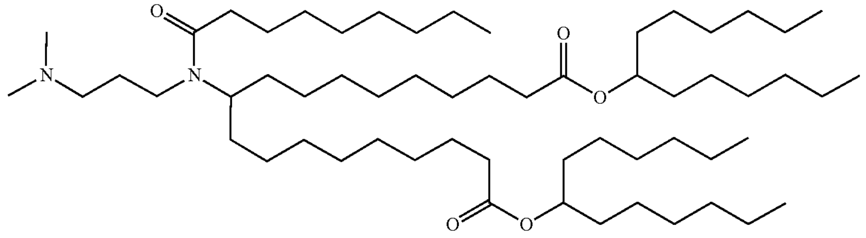 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

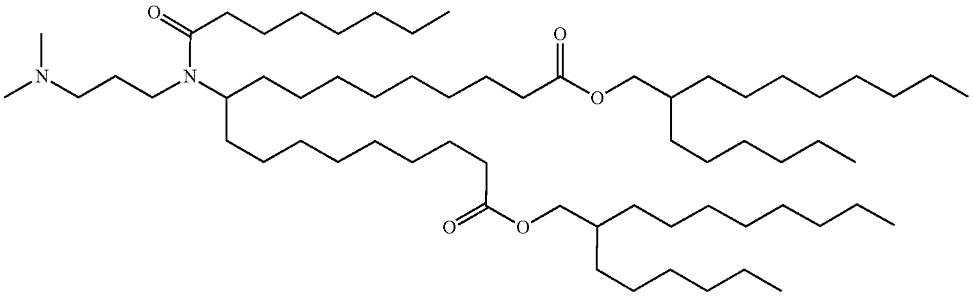 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

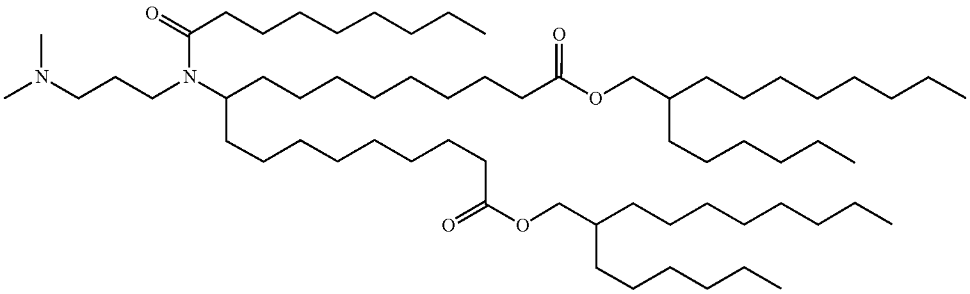 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

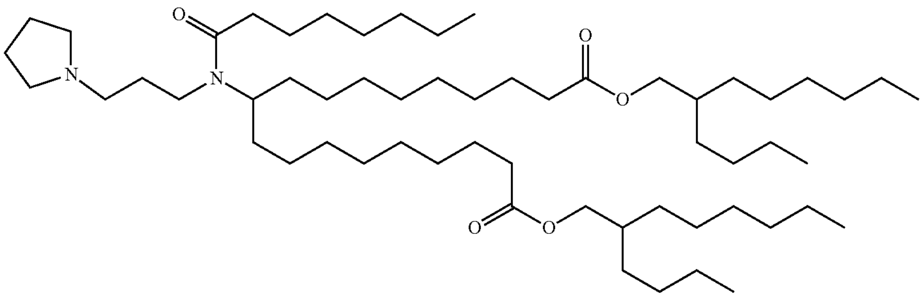 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

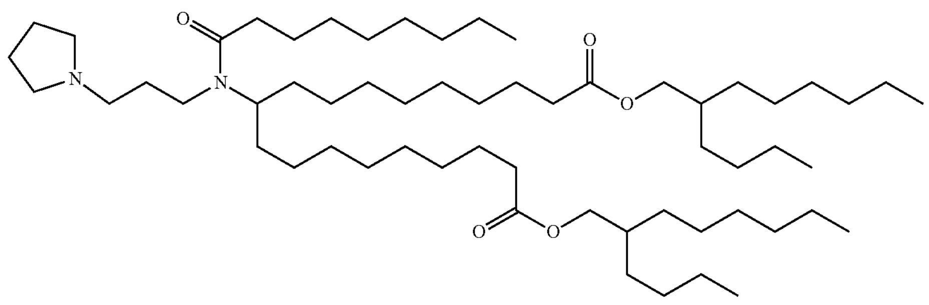 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

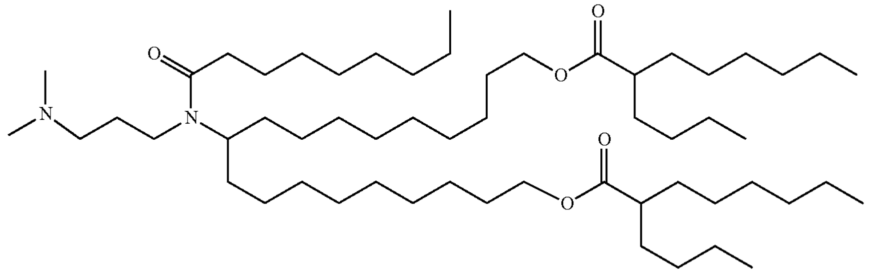 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

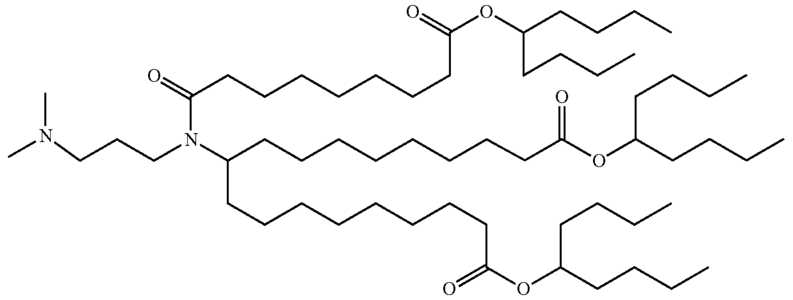 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

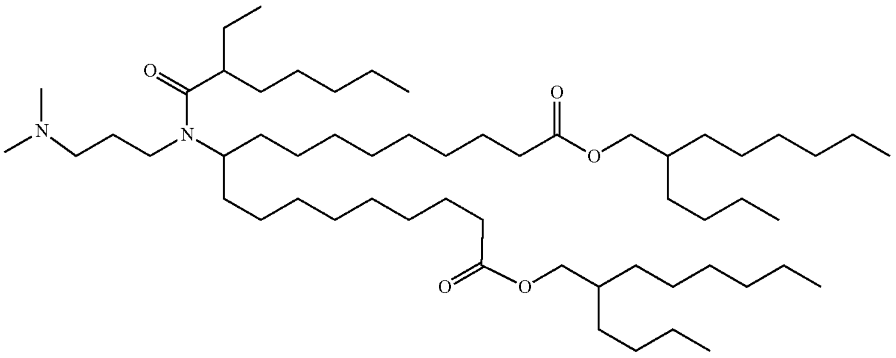 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

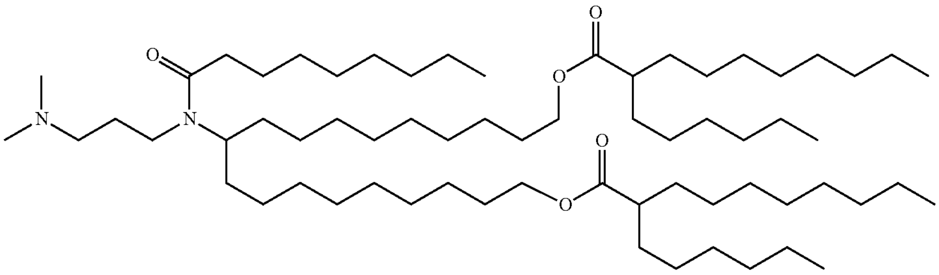 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

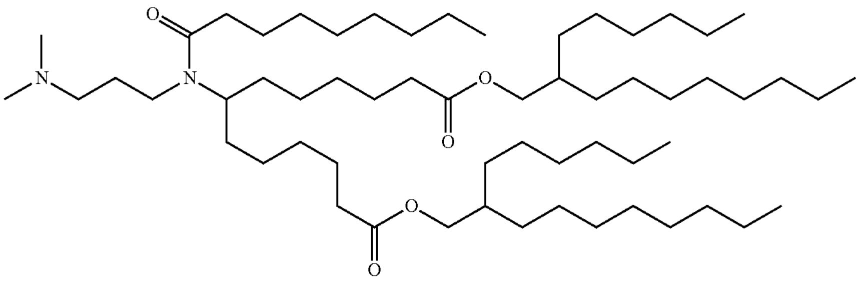 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

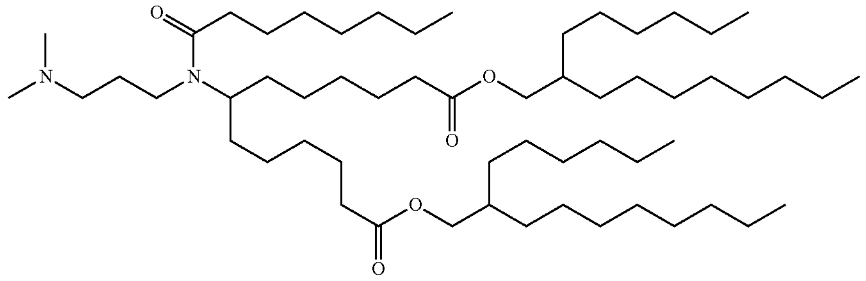 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

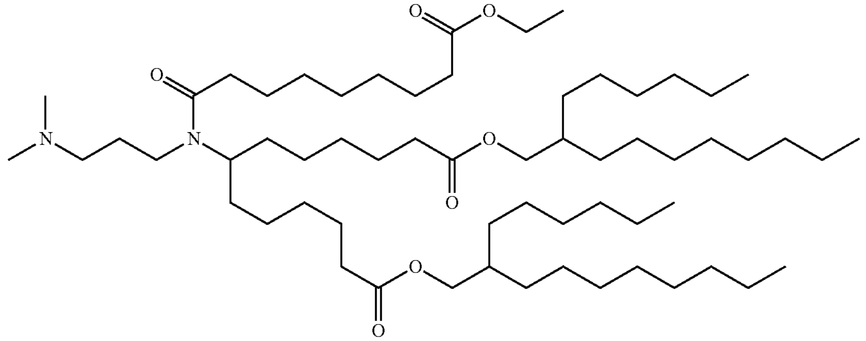 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

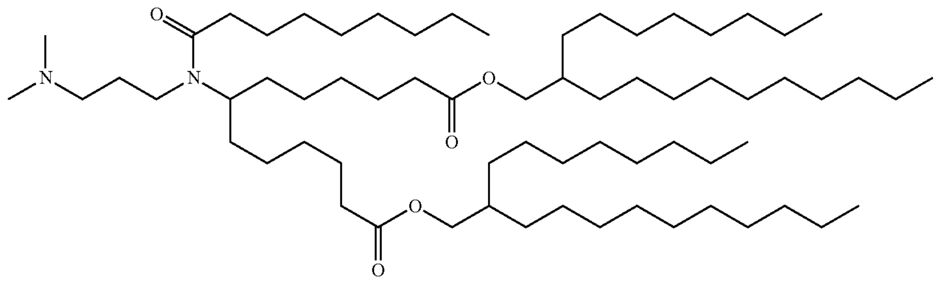 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

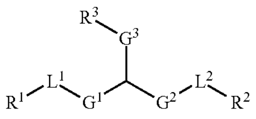

or a pharmaceutically acceptable salt thereof, wherein one of L1 or L2 is —O(C═O)—, —(C═O)O—, —C(═O)—, —O—, —S(O)x, —S—S—, —C(═O)S—, —SC(═O)—, —NRaC(═O)—, —C(═O)NRa—, NRaC(═O)NRa—, —OC(═O)NRa—, or —NRaC(═O)O—; and the other of L1 or L2 is —O(C═O)—, —(C═O)O—, —C(═O)—, —O—, —S(O)x, —S—S—, —C(═O)S—, SC(═O)—, —NRaC(═O)—, —C(═O)NRa—, NRaC(═O)NRa—, —OC(═O)NRa- or —NRaC(═O)O— or a direct bond; G1 and G2 are each independently unsubstituted C1-C12 alkylene or C1-C12 alkenylene; G3 is C1-C24 alkylene, C1-C24 alkenylene, C3-C8 cycloalkylene, C3-C8 cycloalkenylene; Ra is H or C1-C12 alkyl; R1 and R2 are each independently C6-C24 alkyl or C6-C24 alkenyl; R3 is H, OR5, CN, —C(═O)OR4, —OC(═O)R4 or —NR5 C(═O) R4; R4 is C1-C12 alkyl; R5 is H or C1-C6 alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

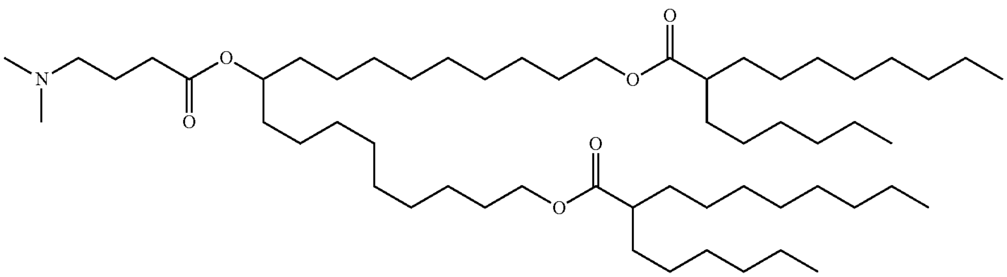 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

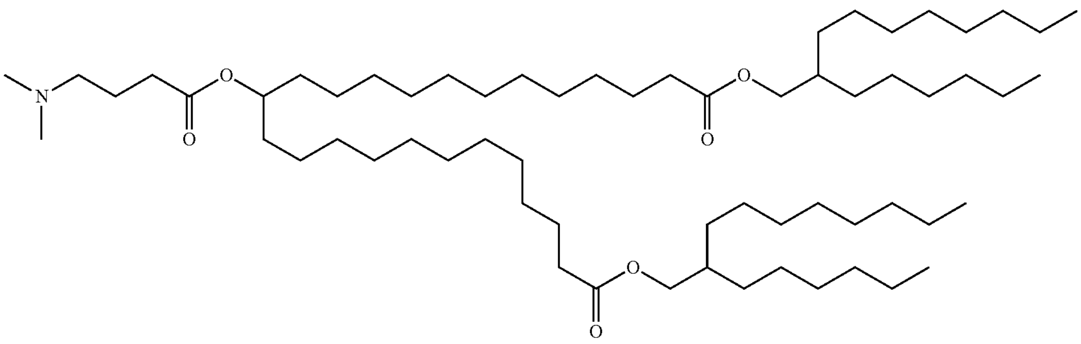 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

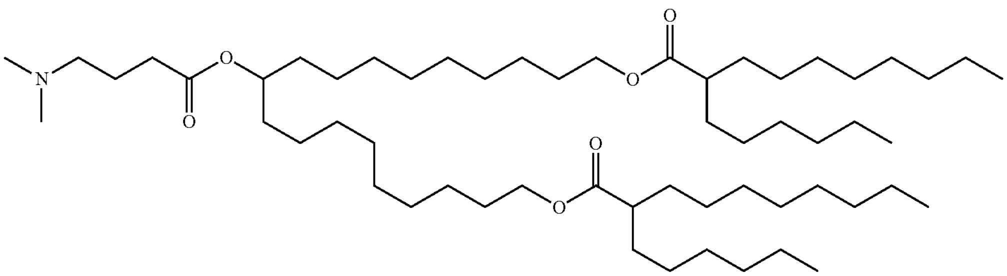 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

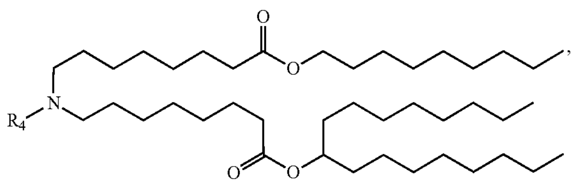
,

-continued

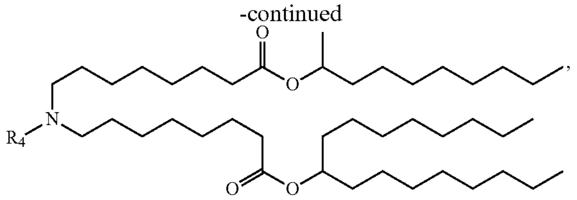

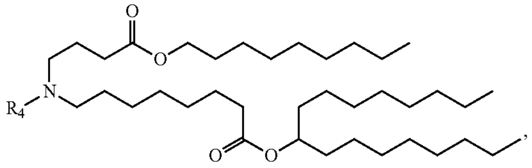

, and

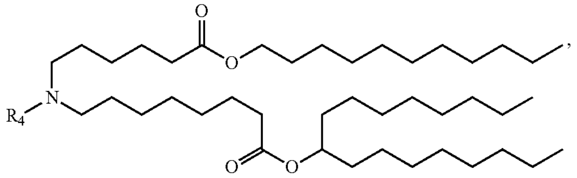

and pharmaceutically acceptable salts thereof. For any one of these four formulas, R4 is independently selected from —$(CH_2)$nQ and —$(CH_2)$ nCHQR; Q is selected from the group consisting of —OR, —OH, —O(CH2)nN(R)2, —OC(O)R, —CX3, —CN, —N(R)C(O)R, —N(H)C(O)R, —N(R)S(O)2R, —N(H)S(O)2R, —N(R)C(O)N(R)2, —N(H)C(O)N(R)2, —N(H)C(O)N(H)(R), —N(R)C(S)N(R)2, —N(H)C(S)N(R)2, —N(H)C(S)N(H)(R), and a heterocycle; and n is 1, 2, or 3. In certain embodiments, the compositions and methods of the present invention include a cationic lipid having a compound structure of:

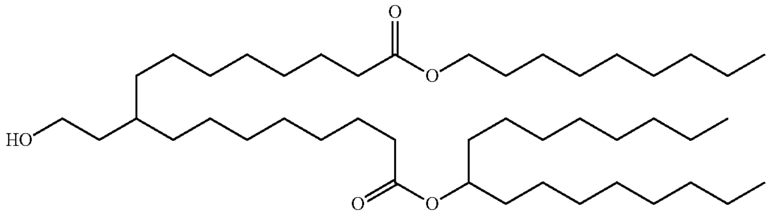 [SMILES: CCCCCCCCCOC(=O)CCCCCCCC(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

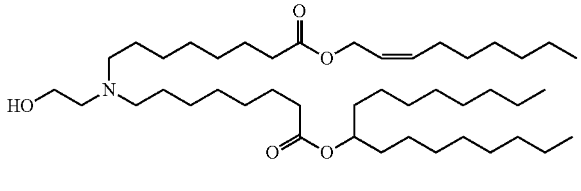 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

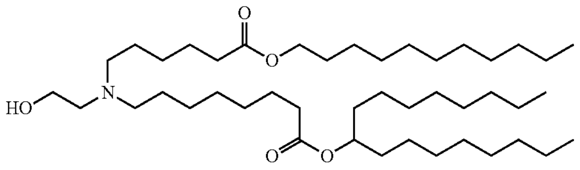 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

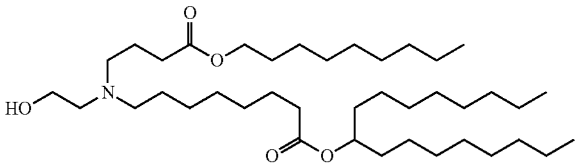 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

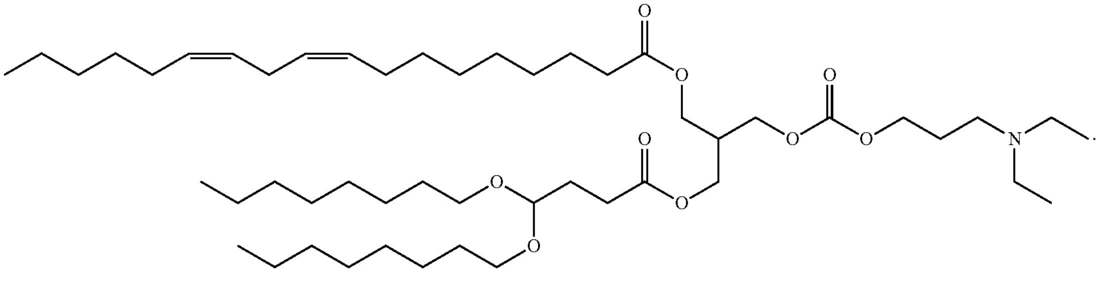 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

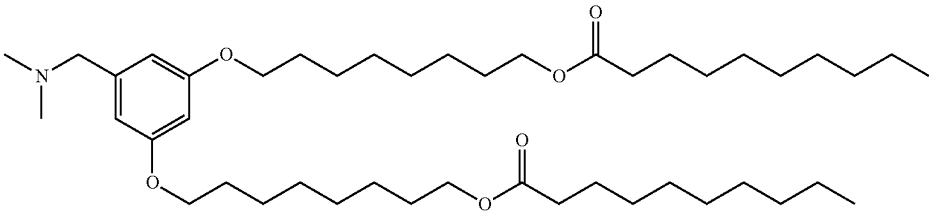 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

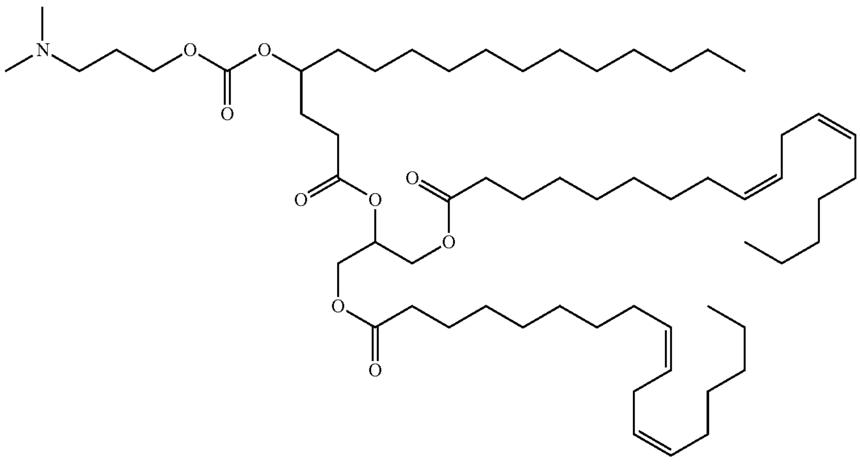 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

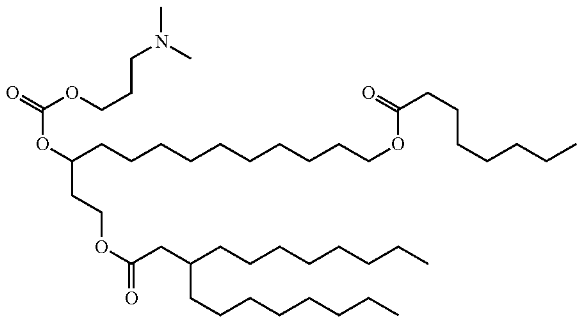 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

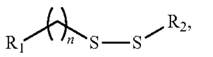

wherein R1 is selected from the group consisting of imidazole, guanidinium, amino, imine, enamine, an optionally-substituted alkyl amino (e.g., an alkyl amino such as dimethylamino) and pyridyl; wherein R2 is selected from the group consisting of one of the following two formulas:

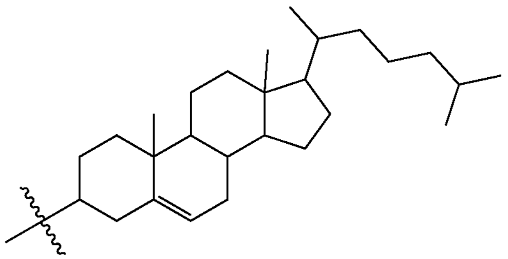

and

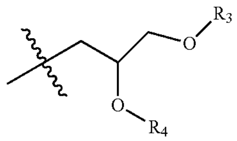

and wherein R3 and R4 are each independently selected from the group consisting of an optionally substituted, variably saturated or unsaturated C6-C20 alkyl and an optionally substituted, variably saturated or unsaturated C6-C20 acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

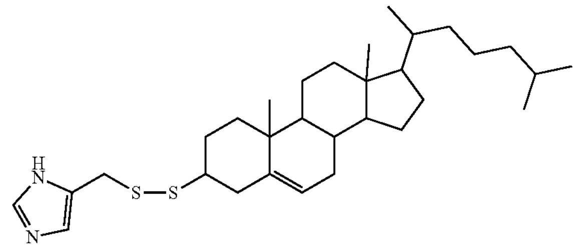

and pharmaceutically acceptable salts thereof. In certain embodiments, the compositions and methods of the present invention include a cationic lipid, "HGT4002" (also referred to herein as "Guan-SS-Chol"), having a compound structure of:

(HGT4002)

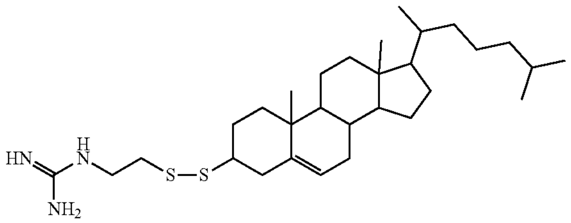

and pharmaceutically acceptable salts thereof. In certain embodiments, the compositions and methods of the present invention include a cationic lipid, "HGT4003", having a compound structure of:

(HGT4003)

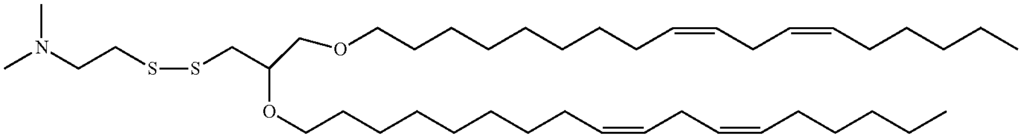

and pharmaceutically acceptable salts thereof. In certain embodiments, the compositions and methods of the present invention include a cationic lipid, "HGT4004", having a compound structure of:

(HGT4004)

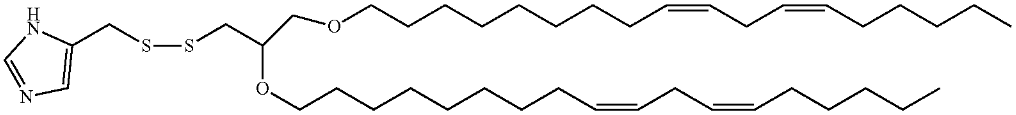

and pharmaceutically acceptable salts thereof. In certain embodiments, the compositions and methods of the present invention include a cationic lipid "HGT4005", having a compound structure of:

(HGT4005)

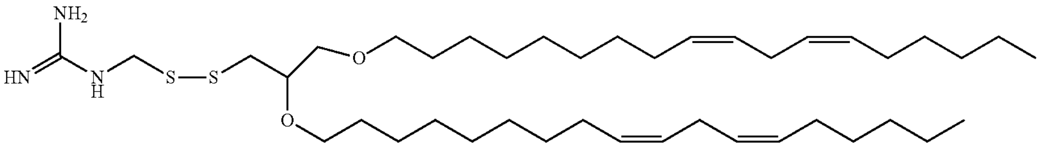

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'), (I')

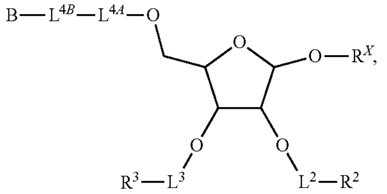

wherein:

RX is independently —H, -L1-R1, or -L5A-L5B—B';

each of L1, L2, and L3 is independently a covalent bond, —C(O)—, —C(O)O—, —C(O)S—, or —C(O)NRL-;

each L4A and L5A is independently —C(O)—, —C(O)O—, or —C(O)NRL-;

each L4B and L5B is independently C1-C20 alkylene; C2-C20 alkenylene; or C2-C20 alkynylene;

each B and B' is NR4R5 or a 5- to 10-membered nitrogen-containing heteroaryl;

each R1, R2, and R3 is independently C6-C30 alkyl, C6-C30 alkenyl, or C6-C30 alkynyl;

each R4 and R5 is independently hydrogen, C1-C10 alkyl; C2-C10 alkenyl; or C2-C10 alkynyl; and each RL is independently hydrogen, C1-C20 alkyl, C2-C20 alkenyl, or C2-C20 alkynyl.

In certain embodiments, the compositions and methods of the present invention include a cationic lipid that is Compound (139) of 62/672,194, having a compound structure of:

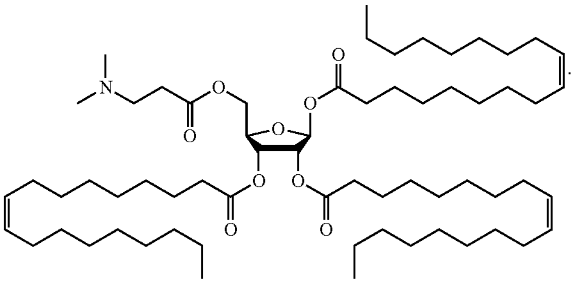

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethyl-1-(cis,cis-9',1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z,12Z)-octadeca-9,12-dien-1-yloxy]propane-1-amine ("Octyl-CLinDMA"); (2R)-2-((8-[(3beta)-cholest-5-en-3-yloxy]octyl)oxy)-N,N-dimethyl-3-[(9Z,12Z)-octadeca-9,12-dien-1-yloxy]propan-1-amine ("Octyl-CLinDMA (2R)"); (2S)-2-((8-[(3P)-cholest-5-en-3-yloxy]octyl)oxy)-N, fsl-dimethyh3-[(9Z,12Z)-octadeca-9,12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3]-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety. In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z,12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, one or more cationic lipids suitable for the compositions and methods of the present invention include a cationic lipid that is TL1-04D-DMA, having a compound structure of:

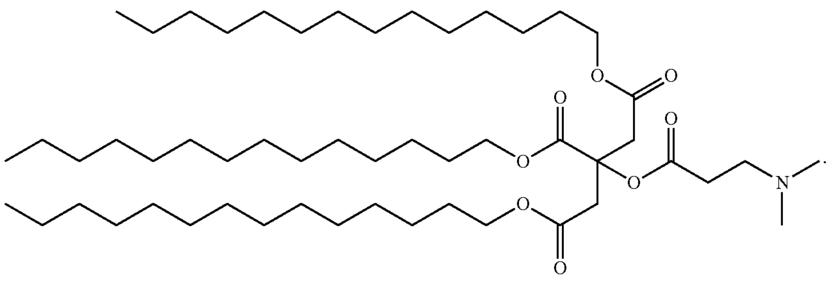

("TL1-04D-DMA")

In some embodiments, one or more cationic lipids suitable for the compositions and methods of the present invention include a cationic lipid that is GL-TES-SA-DME-E18-2, having a compound structure of:

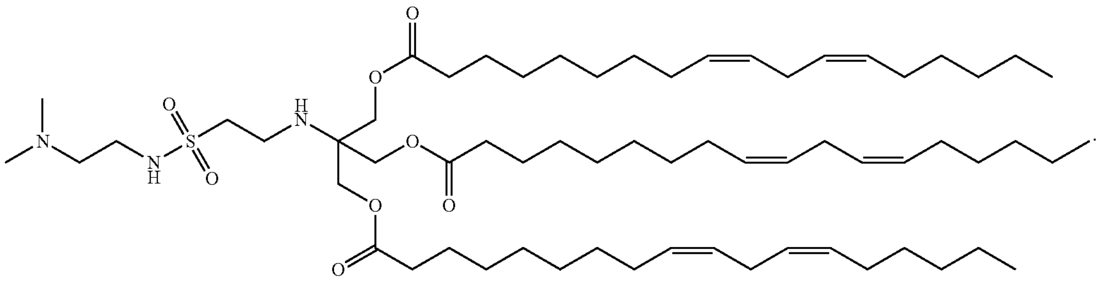

("GL-TES-SA-DME-E18-2")

In some embodiments, one or more cationic lipids suitable for the compositions and methods of present invention include a cationic lipid that has a structure according to Formula (IIA):

(IIA)

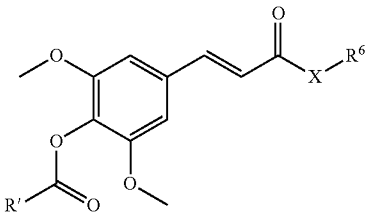

wherein X is O or S;
wherein R' is

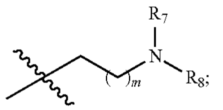

wherein $R^6$ is

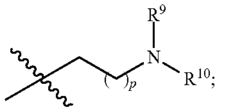

wherein m and p are each independently 0, 1, 2, 3, 4 or 5;

wherein $R^7$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_kR^A$ or $—(CH_2)_kCH(OR^{11})R^A$;

wherein $R^8$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_nR^B$ or $—(CH_2)_nCH(OR^{12})R^B$;

wherein $R^9$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_qR^C$ or $—(CH_2)_qCH(OR^{13})R^C$;

wherein $R^{10}$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $—(CH_2)_rR^D$ or $—(CH_2)_rCH(OR^{14})R^D$;

wherein k, n, q and r are each independently 1, 2, 3, 4, or 5;

or wherein (i) $R^7$ and $R^8$ or (ii) $R^9$ and $R^{10}$ together form an optionally substituted 5- or 6-membered heterocycloalkyl or heteroaryl wherein the heterocycloalkyl or heteroaryl comprises 1 to 3 heteroatoms selected from N, O and S;

wherein $R^{11}$, $R^{12}$, $R^{13}$ and $R^{14}$ are each independently selected from H, methyl, ethyl or propyl wherein $R^A$, $R^B$, $R^C$ and $R^D$ are each independently selected from optionally substituted $(C_6\text{-}C_{20})$alkyl, optionally substituted $(C_6\text{-}C_{20})$alkenyl, optionally substituted $(C_6\text{-}C_{20})$alkynyl, optionally substituted $(C_6\text{-}C_{20})$acyl, optionally substituted —OC(O)alkyl, optionally substituted —OC(O)alkenyl, optionally substituted $(C_1\text{-}C_6)$ monoalkylamino, optionally substituted $(C_1\text{-}C_6)$ dialkylamino, optionally substituted $(C_1\text{-}C_6)$ alkoxy, —OH, $—NH_2$;

wherein at least one of $R^7$, $R^8$, $R^9$, $R^{10}$ comprises a $R^A$, $R^B$, $R^C$ or $R^D$ moiety respectively wherein that $R^A$, $R^B$, $R^C$ or $R^D$ is independently selected from optionally substituted $(C_6\text{-}C_{20})$alkyl, optionally substituted $(C_6\text{-}C_{20})$alkenyl, optionally substituted $(C_6\text{-}C_{20})$alkynyl, optionally substituted $(C_6\text{-}C_{20})$acyl, optionally substituted $—OC(O)(C_6\text{-}C_{20})$alkyl or optionally substituted $—OC(O)(C_6\text{-}C_{20})$alkenyl;

or a pharmaceutically acceptable salt thereof.

In some embodiments, the one or more cationic lipids suitable for the compositions and methods of present invention include a cationic lipid that has a structure according to Formula (IIID):

(IIID)

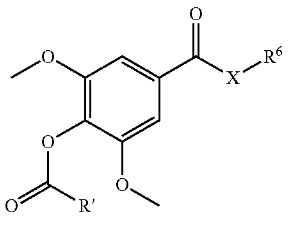

wherein X is O or S;

wherein R' is

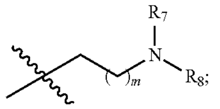

wherein $R^6$ is

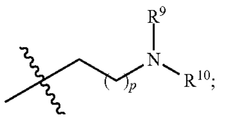

wherein m and p are each independently 0, 1, 2, 3, 4 or 5;

wherein $R^7$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $-(CH_2)_kR^A$ or $-(CH_2)_kCH(OR'')R^A$;

wherein $R^8$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $-(CH_2)_nR^B$ or $-(CH_2)_nCH(OR^{12})R^B$;

wherein $R^9$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $-(CH_2)_qR^C$ or $-(CH_2)_qCH(OR^{13})R^C$;

wherein $R^{10}$ is selected from H, optionally substituted $(C_1\text{-}C_6)$alkyl, optionally substituted $(C_2\text{-}C_6)$alkenyl, optionally substituted $(C_2\text{-}C_6)$alkynyl, optionally substituted $(C_1\text{-}C_6)$acyl, $-(CH_2)_rR^D$ or $-(CH_2)_rCH(OR^{14})R^D$;

wherein k, n, q and r are each independently 1, 2, 3, 4, or 5;

or wherein (i) $R^7$ and $R^8$ or (ii) $R^9$ and $R^{10}$ together form an optionally substituted 5- or 6-membered heterocycloalkyl or heteroaryl wherein the heterocycloalkyl or heteroaryl comprises 1 to 3 heteroatoms selected from N, O and S;

wherein $R^{11}$, $R^{12}$, $R^{13}$ and $R^{14}$ are each independently selected from H, methyl, ethyl or propyl wherein $R^A$, $R^B$, $R^C$ and $R^D$ are each independently selected from optionally substituted $(C_6\text{-}C_{20})$alkyl, optionally substituted $(C_6\text{-}C_{20})$alkenyl, optionally substituted $(C_6\text{-}C_{20})$alkynyl, optionally substituted $(C_6\text{-}C_{20})$acyl, optionally substituted —OC(O)alkyl, optionally substituted —OC(O)alkenyl, optionally substituted $(C_1\text{-}C_6)$ monoalkylamino, optionally substituted $(C_1\text{-}C_6)$ dialkylamino, optionally substituted $(C_1\text{-}C_6)$ alkoxy, —OH, $-NH_2$;

wherein at least one of $R^7$, $R^8$, $R^9$, $R^{10}$ comprises a $R^A$, $R^B$, $R^C$ or $R^D$ moiety respectively wherein that $R^A$, $R^B$, $R^C$ or $R^D$ is independently selected from optionally substituted $(C_6\text{-}C_{20})$alkyl, optionally substituted $(C_6\text{-}C_{20})$alkenyl, optionally substituted $(C_6\text{-}C_{20})$alkynyl, optionally substituted $(C_6\text{-}C_{20})$acyl, optionally substituted $-OC(O)(C_6\text{-}C_{20})$alkyl or optionally substituted $-OC(O)(C_6\text{-}C_{20})$alkenyl;

or a pharmaceutically acceptable salt thereof.

In some embodiments of Formula (IIA) or Formula (IIID), X is 0.

In some embodiments of Formula (IIA) or Formula (IIID), m is 1, 2 or 3.

In some embodiments of Formula (IIA) or Formula (IIID), p is 1, 2 or 3.

In some embodiments of Formula (IIA) or Formula (IIID), R' is:

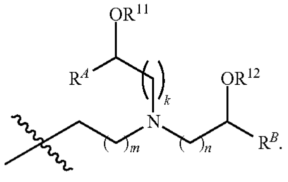

In some embodiments of Formula (IIA) or Formula (IIID), i) k, m and n=1; or ii) k, m and n=1 and $R^{11}$ and $R^{12}$=H; or iii) k and n=1, and m=2; or iv) k and n=1, m=2 and $R^{11}$ and $R^{12}$=H; or v) k and n=1, and m=3; or vi) k and n=1, m=3 and $R^{11}$ and $R^{12}$=H.

In some embodiments of Formula (IIA) or Formula (IIID), $R^6$ is

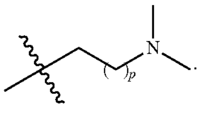

In some embodiments of Formula (IIA) or Formula (IIID), $R^6$ is

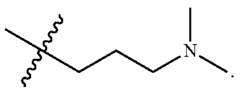 [SMILES: *CCCN(C)C]

In some embodiments of Formula (IIA) or Formula (IIID), $R^6$ is selected from the group consisting of:

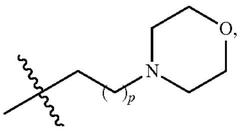

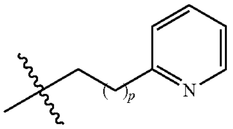

or

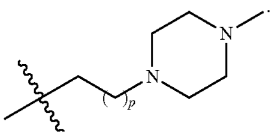

In some embodiments of Formula (IIA) or Formula (IIID), $R^6$ is selected from the group consisting of:

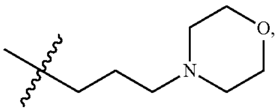

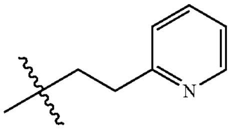

or

-continued

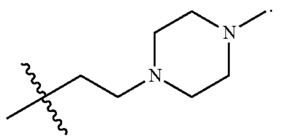

In some embodiments of Formula (IIA) or Formula (IIID), $R^6$ is

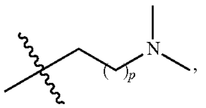

R' is

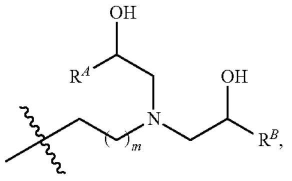

m is 2 and p is 2.

In some embodiments of Formula (IIA) or Formula (IIID), $R^6$ is

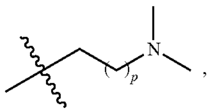

P R' is

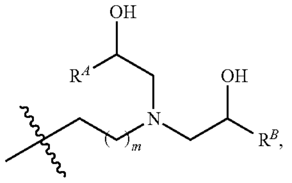

m is 3 and p is 2.

In some embodiments of Formula (IIA) or Formula (IIID), $R^A$ and $R^B$ are each independently selected from optionally substituted $(C_6-C_{20})$alkyl, optionally substituted $(C_6-C_{20})$alkenyl, optionally substituted $(C_6-C_{20})$alkynyl. In some embodiments of Formula (IIA) or Formula (IIID), $R^A$ and $R^B$ are the same and selected from optionally substituted $(C_6-C_{20})$alkyl, optionally substituted $(C_6-C_{20})$alkenyl, optionally substituted $(C_6-C_{20})$alkynyl. In some embodiments of Formula (IIA) or Formula (IIID), $R^A$ and $R^B$ are each independently optionally substituted $(C_6-C_{20})$alkyl. In some embodiments of Formula (IIA) or Formula (IIID), $R^A$ and $R^B$ are the same and are optionally substituted $(C_6-C_{20})$alkyl. In some embodiments of Formula (IIA) or Formula (IIID), $R^A$ and $R^B$ are each independently optionally substituted $(C_6-C_{20})$alkenyl. In some embodiments of Formula (IIA) or Formula (IIID), $R^A$ and $R^B$ are the same and are optionally substituted $(C_6-C_{20})$alkenyl. In some embodiments of Formula (IIA) or Formula (IIID), $R^A$ and $R^B$ are each independently optionally substituted $(C_6-C_{20})$alkynyl. In some embodiments of Formula (IIA) or Formula (IIID), $R^A$ and $R^B$ are the same and are optionally substituted $(C_6-C_{20})$alkynyl. In some embodiments of Formula (IIA) or Formula (IIID), $R^A$ and $R^B$ are each independently optionally substituted $(C_6-C_{20})$acyl. In some embodiments of Formula (IIA) or Formula (IIID), $R^A$ and $R^B$ are the same and are optionally substituted $(C_6-C_{20})$acyl. In some embodiments of Formula (IIA) or Formula (IIID), $R^A$ and $R^B$ are each independently optionally substituted $—OC(O)(C_6-C_{20})$alkyl. In some embodiments of Formula (IIA) or Formula (IIID), $R^A$ and $R^B$ are the same and are optionally substituted $—OC(O)(C_6-C_{20})$alkyl. In some embodiments of Formula (IIA) or Formula (IIID), $R^A$ and $R^B$ are each independently optionally substituted $—OC(O)(C_6-C_{20})$alkenyl. In some embodiments of Formula (IIA) or Formula (IIID), $R^A$ and $R^B$ are the same and are optionally substituted $—OC(O)(C_6-C_{20})$alkenyl.

In some embodiments, the substituents in Formula (IIA) and Formula (IIID) are as defined in PCT/US21/25128, which is incorporated herein by reference.

In some embodiments, the chemical definitions for the substituents in Formula (IIA) and Formula (IIID) are as defined in paragraphs [044]-[089] of PCT/US21/25128, which is incorporated herein by reference.

In some embodiments, the substituents in Formula (IIA) and Formula (IIID) are as defined in U.S. 63/176,549, which is incorporated herein by reference.

In some embodiments, the chemical definitions for the substituents in Formula (IIA) and Formula (IIID) are as defined in paragraphs [0018]-[0028] of U.S. 63/176,549, which is incorporated herein by reference.

In some embodiments, the cationic lipid is any of the cationic lipids disclosed in PCT/US21/25128, which is incorporated herein by reference, for example, any of Formulae (I), (II), (IIA), (IIB), (IIC), (IID), (IIE), (IIF), (IIG), (IIH), (IIJ), (IIK), (III), (IIIA), (IIIB), (IIIC), (IIID), (IIIE), (IIIF), (IIIG), (IIIH), (IIII), (IIIJ), (IIIK), (IIIL), (IIIM), (IV), (VI), (VII), (VIII), (IX), and/or (X).

In some embodiments, the one or more cationic lipids suitable for the compositions and methods of present invention include a cationic lipid that has a structure according to Formula (I), (I)

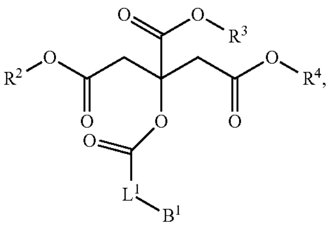

or a pharmaceutically acceptable salt thereof, wherein $B^1$ is an ionizable nitrogen-containing group;

each of $R^2$, $R^3$, and $R^4$ is independently $C_6-C_{30}$ alkyl, $C_6-C_{30}$ alkenyl, or $C_6-C_{30}$ alkynyl; and $L^1$ is $C_1-C_{10}$ alkylene.

In embodiments of Formula (I), $R^{1A}$ is H.

In embodiments of Formula (I), $L^1$ is unsubstituted $C_1-C_{10}$ alkylene.

In embodiments of Formula (I), $L^1$ is $(CH_2)_2$, $(CH_2)_3$, $(CH_2)_4$, or $(CH_2)_5$.

In embodiments of Formula (I), $B^1$ is independently $NH_2$, guanidine, amidine, a mono- or dialkylamine, 5- to 6-membered nitrogen-containing heterocycloalkyl, or 5- to 6-membered nitrogen-containing heteroaryl.

In embodiments of Formula (I), $B^1$ is independently

, 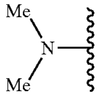, 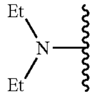, 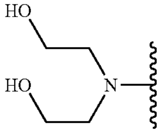, 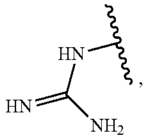, 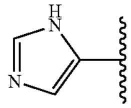, 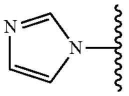, or 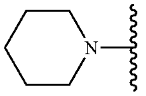.

In embodiments of Formula (I), $B^1$ is independently

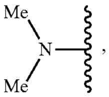, 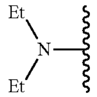, 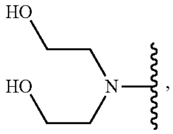, or 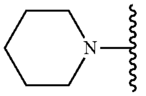.

In embodiments of Formula (I), each of $R^2$, $R^3$, and $R^4$ is independently unsubstituted linear $C_6$-$C_{22}$ alkyl, unsubstituted linear $C_6$-$C_{22}$ alkenyl, unsubstituted linear $C_6$-$C_{22}$ alkynyl, unsubstituted branched $C_6$-$C_{22}$ alkyl, unsubstituted branched $C_6$-$C_{22}$ alkenyl, or unsubstituted branched $C_6$-$C_{22}$ alkynyl.

In embodiments of Formula (I), each of $R^2$, $R^3$, and $R^4$ is unsubstituted $C_6$-$C_{22}$ alkyl.

In embodiments of Formula (I), each of $R^2$, $R^3$, and $R^4$ is independently $C_6$-$C_{12}$ alkyl substituted by —$O(CO)R^5$ or —$C(O)OR^5$, wherein $R^5$ is unsubstituted $C_6$-$C_{14}$ alkyl.

In embodiments of Formula (I), each of $R^2$, $R^3$, and $R^4$ is unsubstituted $C_6$-$C_{22}$ alkenyl. In embodiments of Formula (I), said $C_6$-$C_{22}$ alkenyl is a monoalkenyl, a dienyl, or a trienyl.

In embodiments of Formula (I), each of $R^2$, $R^3$, and $R^4$ is

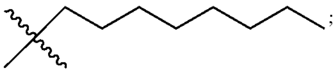; 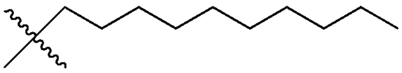;

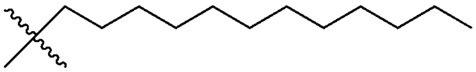; 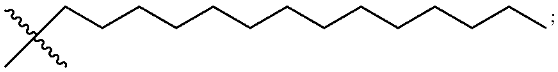;

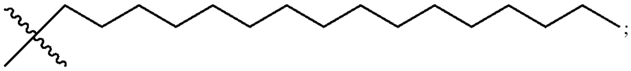;

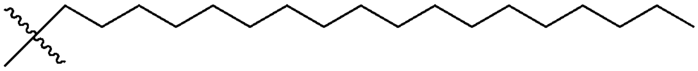;

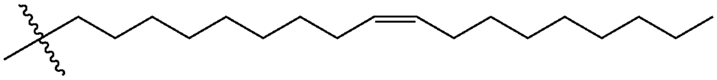;

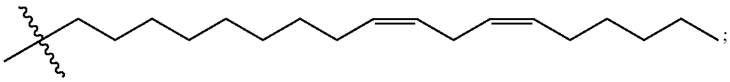;

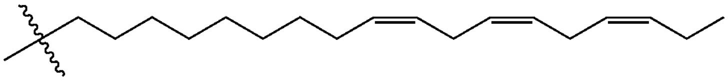;

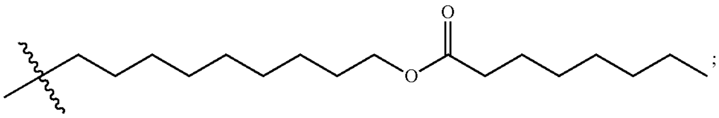;

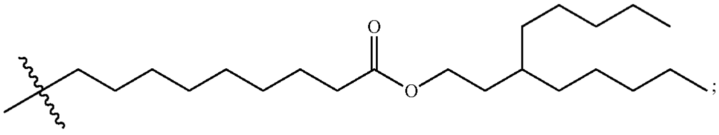; and

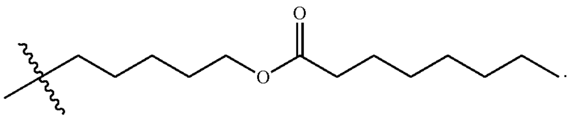.

In embodiments of Formula (I), each of $R^2$, $R^3$, and $R^4$ is

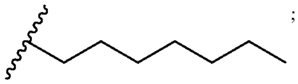
;
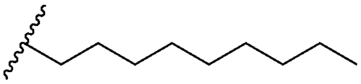
;
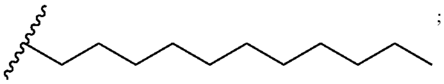
;
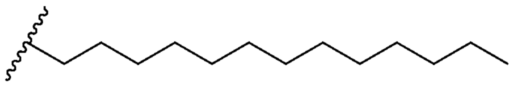
;
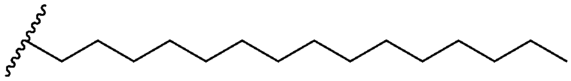
;
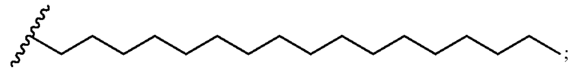
;
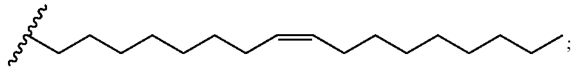
;
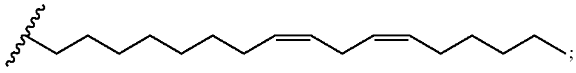
;

-continued

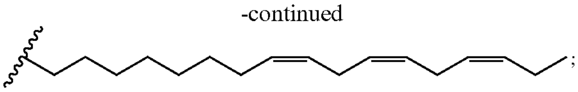
;
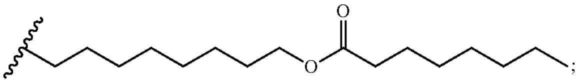
;
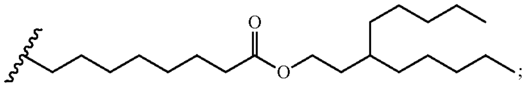
; and
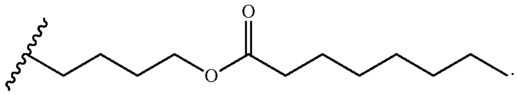
.

In some embodiments, the substituents in Formula (I) are as defined in WO 2020/257716, which is incorporated herein by reference.

In some embodiments, the chemical definitions for the substituents in Formula (I) are as defined in paragraphs [0105]-[0118], [0122] and [0123] of WO 2020/257716, which is incorporated herein by reference.

In some embodiments, the cationic lipid is any of the cationic lipids disclosed in WO 2020/257716, which is incorporated herein by reference, for example, any of Formulae (A), (I), (II), (AI), (AII), (AIII), (IIa), (IIb), (IIc), (IId), (III), (IV), (V) and/or (VI).

In some embodiments, the cationic lipid suitable for the compositions and methods of the present invention is SY-3-E14-DMAPr, having a compound structure of:

("SY-3-E14-DMAPr")

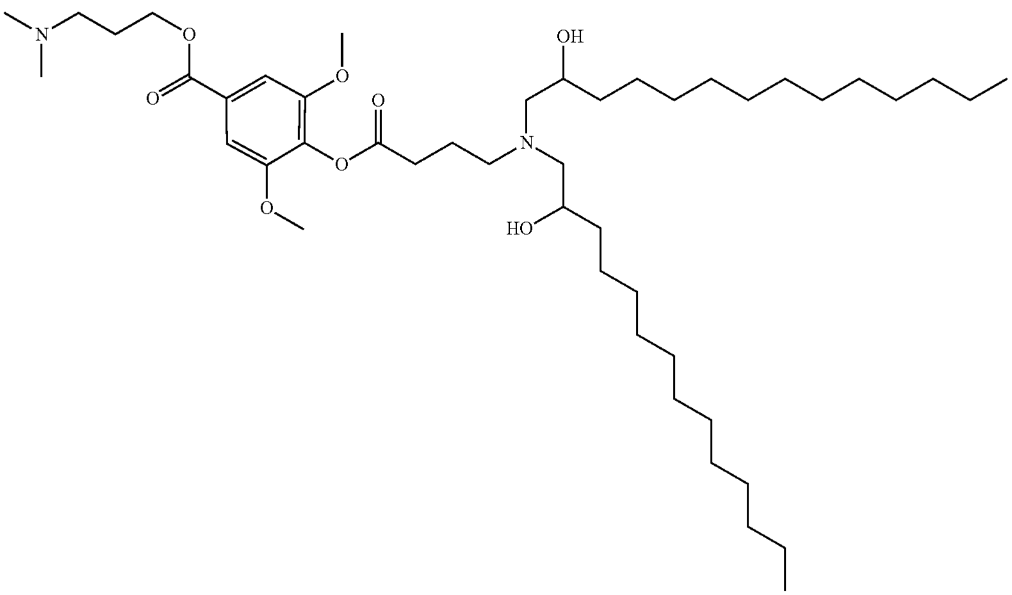
.

In some embodiments, the cationic lipid suitable for the compositions and methods of the present invention is TL1-01D-DMA, having a compound structure of:

("TL1-01D-DMA")

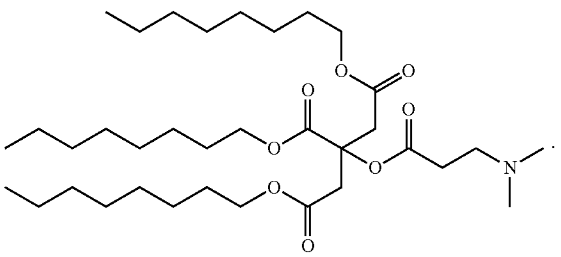

In some embodiments, the cationic lipid suitable for the compositions and methods of the present invention is TL1-10D-DMA, having a compound structure of:

("TL1-10D-DMA")

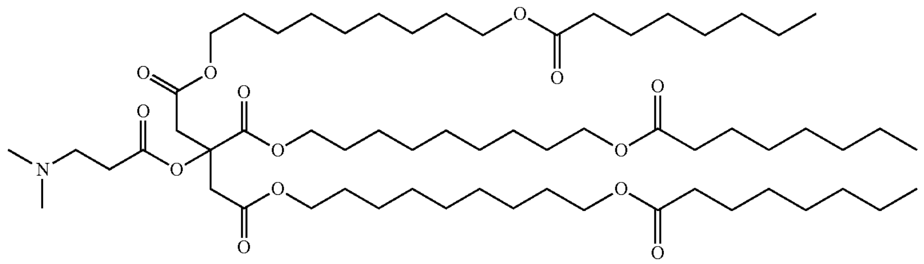

In some embodiments, the cationic lipid suitable for the compositions and methods of the present invention is GL-TES-SA-DMP-E18-2, having a compound structure of:

("GL-TES-SA-DMP-E18-2")

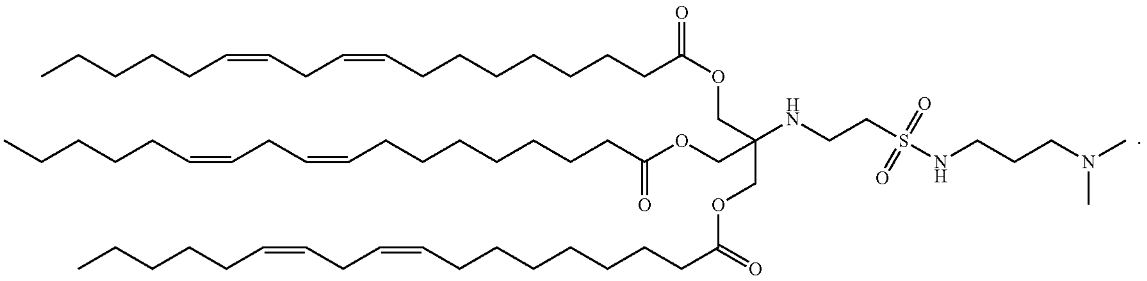

In some embodiments, the cationic lipid suitable for the compositions and methods of the present invention is HEP-E4-E10, having a compound structure of:

("HEP-E4-E10")
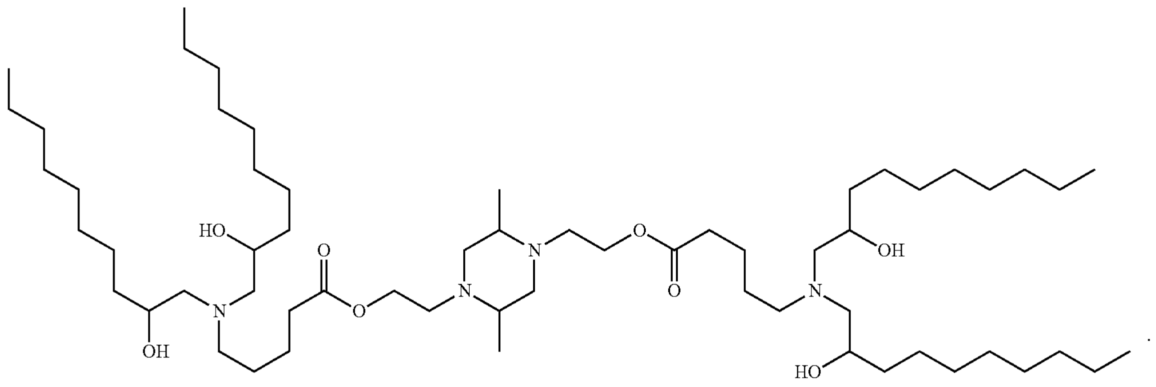
In some embodiments, the cationic lipid suitable for the compositions and methods of the present invention is HEP-E3-E10, having a compound structure of:
("HEP-E3-E10")
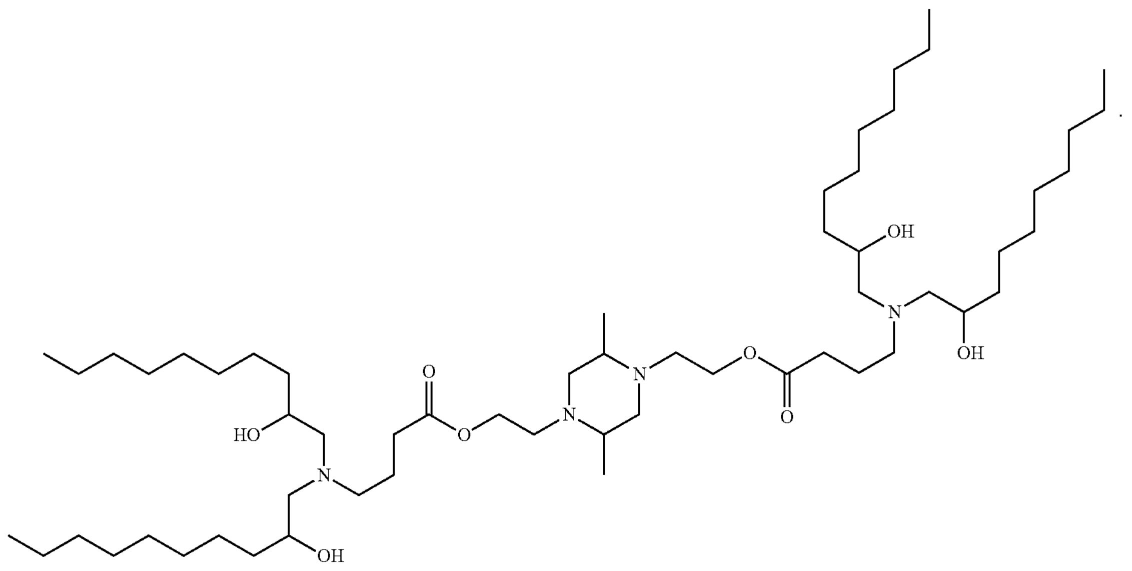
In some embodiments, the cationic lipid suitable for the compositions and methods of the present invention is SI-4-E14-DMAPr, having a compound structure of:

(SI-4-E14-DMAPr)

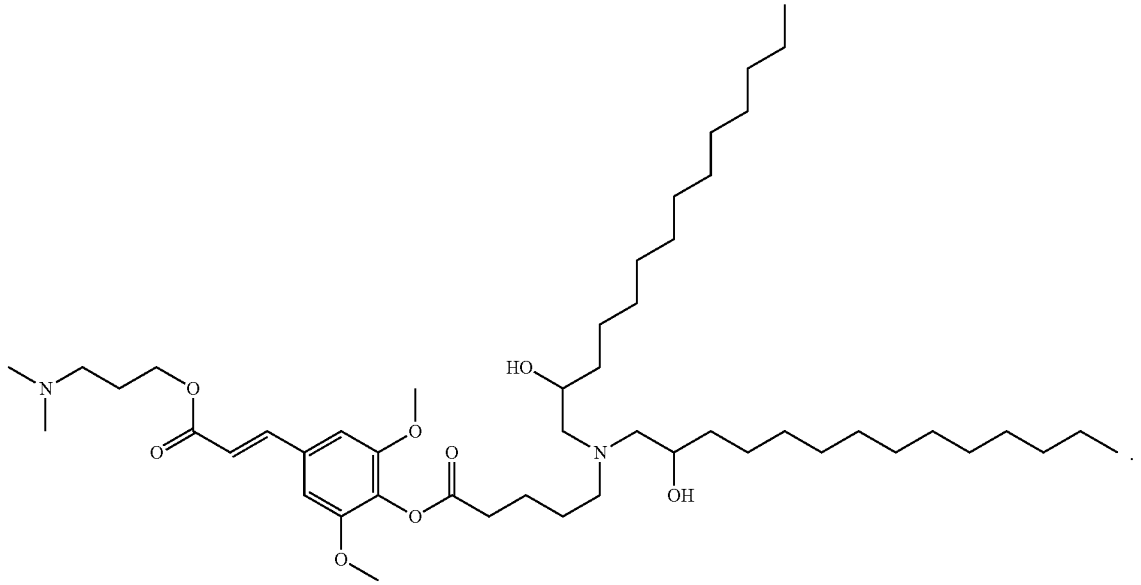

In some embodiments, the cationic lipid suitable for the compositions and methods of the present invention is SY-010, having a compound structure of:

(SY-010)

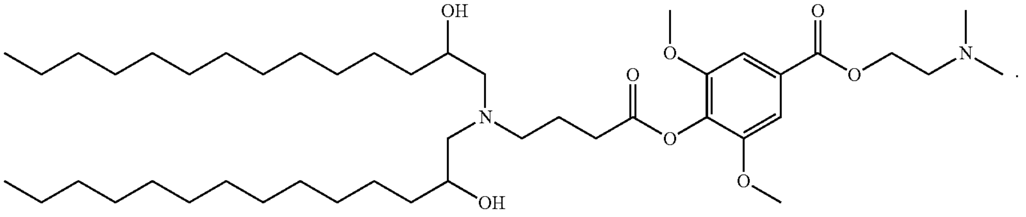

In some embodiments, the cationic lipid suitable for the lipid nanoparticles and compositions of the present invention is TL1-12D-DMA, having a compound structure of:

TL1-12D-DMA (TL1-12D-DMA)

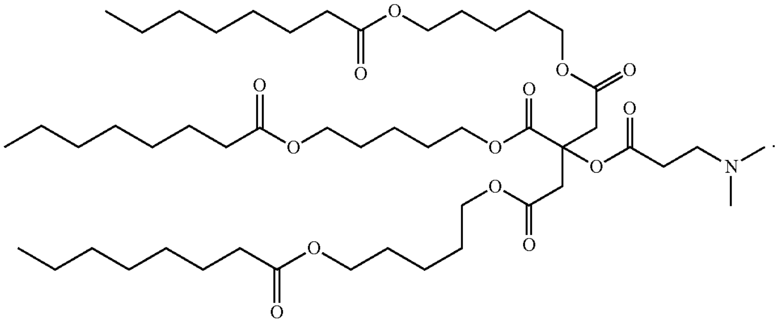

In some embodiments, the cationic lipid is selected from imidazole cholesterol ester (ICE), GL-TES-SA-DMP-E18-2, GL-TES-SA-DME-E18-2, TL1-01D-DMA, TL1-04D-DMA, SY-3-E14-DMAPr, SI-4-E14-DMAPr, SY-010, HEP-E3-E10, HEP-E4-E10, and Guan-SS-Chol. In particular embodiments, the cationic lipid is TL1-01D-DMA or SY-3-E14-DMAPr. In other particular embodiments, the cationic lipid is SY-3-E14-DMAPr, SI-4-E14-DMAPr or SY-010.

In some embodiments, the cationic lipid in a lipid nanoparticle in the composition of the invention is any of the cationic lipids disclosed in PCT/US21/25128, which is incorporated herein by reference.

In some embodiments, the cationic lipid in a lipid nanoparticle in the composition of the invention is any of the cationic lipids disclosed in WO2020257716, which is incorporated herein by reference.

Non-Cationic Helper Lipids

As used herein, the phrase "non-cationic lipid" refers to neutral, zwitterionic or anionic lipid. Specific non-cationic lipids which are suitable for use in the lipid nanoparticles of the invention are distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), 1,2-dioleoyl-sn-glycero-3-phospho-L-serine (DOPS), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 1,2-dierucoyl-sn-glycero-3-phosphoethanolamine (DEPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), 1,2-dimyristelaidoyl-sn-glycero-3-phosphocholine (14:1PC), 1,2-dipalmitelaidoyl-sn-glycero-3-phosphocholine (16:1PC), or 1,2-dimyristoyl-sn-glycero-3-phosphocholine (DMPC).

In some embodiments, a lipid nanoparticle in the composition of the invention includes DOPE or DEPE as the non-cationic lipid component. In other embodiments, a lipid nanoparticle in the composition of the invention includes include DPPC or DOPC as the non-cationic lipid component. In yet other embodiments, a lipid nanoparticle in the composition of the invention includes DSPC as the non-cationic lipid component.

PEG-Modified Lipids

The lipid nanoparticle in a composition of the invention can include a polyethylene glycol (PEG)-modified lipid. In one embodiment, the PEG-modified lipid is a PEG-modified phospholipid or other derivatized lipid such as a derivatized ceramide (PEG-CER), e.g., N-Octanoyl-Sphingosine-1-[Succinyl(Methoxy Polyethylene Glycol)-2000] (C8 PEG-2000 ceramide).

PEG-modified lipids typically include a polyethylene glycol chain of up to 5 kDa in length covalently attached to a lipid with alkyl chain(s) of C6-C20 length. Particularly useful are PEG-modified exchangeable lipids having shorter acyl chains (e.g., C14 or C18). In some embodiments, a PEG-modified (or PEGylated lipid) is a PEGylated cholesterol. Lipid nanoparticles in accordance with the invention typically include a PEG-modified lipid such as 1,2-dimyristoyl-rac-glycero-3-methoxypolyethylene glycol-2000 (DMG-PEG2K). Alternatively, they may include [(polyethylene glycol)-2000]—N,N-ditetradecylacetamide or DSPE-PEG2K—COOH.

The inclusion of such PEG-modified lipids prevents complex aggregation (e.g., during storage and nebulization). Their presence may also increase the mucopenetrating capacity of the lipid nanoparticles of the invention, once they have been delivered into the lung.

In some embodiments, the molar ratio of the PEG-modified lipid in a lipid nanoparticle in a composition of the invention is 2%-6%, e.g., 3%-6% or 4%-6%. In particular embodiments, the molar ratio of the PEG-modified lipid is 3%-5%. Lipid nanoparticles with a molar ratio of the PEG-modified lipid falling within this range have been found to be particularly effective in delivering their mRNA cargo through the mucus layer to the underlying epithelium of the lungs. Accordingly, in one specific embodiment, the molar ratio of the PEG-modified lipid is about 5%. In another specific embodiment, the molar ratio of the PEG-modified lipid is about 4%. In yet a further specific embodiment, the molar ratio of the PEG-modified lipid is about 3%.

For certain applications, lipid nanoparticles in which the PEG-modified lipid component constitutes about 5% of the total lipids by molar ratio have been found to be particularly suitable.

Cholesterol and Cholesterol Analogues

Lipid nanoparticles in a composition of the invention typically include cholesterol as one of the four lipids of their lipid component. In some embodiments, it may be advantageous to use a cholesterol analogue in place of cholesterol. As used herein, the term "cholesterol analogue" encompasses compounds that have a similar structure to cholesterol but differ in one or more atoms, functional groups and/or substructures. In some embodiments, the cholesterol analogue is a functional analogue of cholesterol, for example, it has similar physical, chemical, biochemical and/or pharmacological properties to cholesterol. Examples of cholesterol analogues include but are not limited to: β-sitosterol, stigmastanol, campesterol, fucosterol, stigmasterol, and dexamethasone.

Both β-sitosterol and stigmastanol have been found to be particularly suitable in the preparation of lipid nanoparticles with improved nebulization properties. Accordingly, in one specific embodiment, the cholesterol analogue used in place of cholesterol in a lipid nanoparticle of the invention is β-sitosterol. In another specific embodiment, the cholesterol analogue used in place of cholesterol in a lipid nanoparticle of the invention is stigmastanol.

Exemplary Lipid Nanoparticle Formulations

A lipid nanoparticle in a composition of the invention may include any of the cationic lipids, non-cationic lipids, cholesterol lipids, and PEG-modified lipids described herein.

Cationic lipids particularly suitable for inclusion in such lipid nanoparticles include GL-TES-SA-DME-E18-2, TL1-01D-DMA, SY-3-E14-DMAPr, SI-4-E14-DMAPr, SY-010, GL-TES-SA-DMP-E18-2, HEP-E4-E10, HEP-E3-E10, and TL1-04D-DMA. These cationic lipids have been found to be particularly suitable for use in lipid nanoparticles that are administered through pulmonary delivery via nebulization. Amongst these, TL1-01D-DMA performed particularly well. In addition, SY-3-E14-DMAPr, SI-4-E14-DMAPr and SY-010 also performed particularly well.

Non-cationic lipids particularly suitable for inclusion in such lipid nanoparticles include DOPE, DEPE, DOPC, DSPC and DPPC.

PEG-modifed lipids particularly suitable for inclusion in such lipid nanoparticles include DMG-PEG2K and DSPE-PEG2K—COOH.

Cholesterol analogues particularly suitable for inclusion in such lipid nanoparticles include β-sitosterol and stigmastanol.

Exemplary lipid nanoparticles include one of GL-TES-SA-DME-E18-2, TL1-01D-DMA, SY-3-E14-DMAPr, SI-4-E14-DMAPR, SY-010, GL-TES-SA-DMP-E18-2, HEP-E4-E10, HEP-E3-E10 and TL1-04D-DMA as a cationic lipid component, DOPE, DPPC or DOPC as anon-cationic lipid component, cholesterol as a helper lipid component, and DMG-PEG2K as a PEG-modified lipid component.

In one specific embodiment, the lipid nanoparticle includes DMG-PEG2K, SY-3-E14-DMAPr, cholesterol and DOPE. In one specific embodiment, the lipid nanoparticle includes DMG-PEG2K, SI-4-E14-DMAPr, cholesterol and DOPE. In one specific embodiment, the lipid nanoparticle includes DMG-PEG2K, SY-010, cholesterol and DOPE. In a particular embodiment, the lipid nanoparticle includes 5% DMG-PEG2K, 40% SY-3-E14-DMAPr, 25% cholesterol and 30% DOPE. In another specific embodiments, the lipid nanoparticle includes DMG-PEG2K, TL1-01D-DMA, cholesterol and DOPE. In a particular embodiment, the lipid nanoparticle includes 3% DMG-PEG2K, 40% TL1-01D-DMA, 25% cholesterol and 32% DOPE.

In one specific embodiment, the lipid nanoparticle includes DMG-PEG2K, SY-3-E14-DMAPr, cholesterol and DPPC. In one specific embodiment, the lipid nanoparticle includes DMG-PEG2K, SI-4-E14-DMAPr, cholesterol and DPPC. In one specific embodiment, the lipid nanoparticle includes DMG-PEG2K, SY-010, cholesterol and DPPC. In one specific embodiment, the lipid nanoparticle includes DMG-PEG2K, SY-3-E14-DMAPr, cholesterol and DOPC. In one specific embodiment, the lipid nanoparticle includes DMG-PEG2K, SI-4-E14-DMAPr, cholesterol and DOPC. In one specific embodiment, the lipid nanoparticle includes DMG-PEG2K, SY-010, cholesterol and DOPC.

In some embodiments, the lipid component of a lipid nanoparticle particularly suitable for pulmonary delivery consists of HGT4002 (also referred to herein as Guan-SS-Chol), DOPE and DMG-PEG2K. In some embodiments, the molar ratio of cationic lipid to non-cationic lipid to PEG-modified lipid is approximately 60:35:5.

It was previously discovered that mRNA encapsulating lipid nanoparticles with a lipid component consisting of a cationic lipid, a non-cationic lipid, a PEG-modified lipid and a cholesterol or cholesterol analogue are more effective for pulmonary administration by nebulization when a lower molar ratio of the non-cationic lipid is used than is typically present in lipid nanoparticles delivered via this route of administration. Such mRNA-encapsulating lipid nanoparticles are described in detail in U.S. Provisional Application No. 63/176,549 filed on Apr. 19, 2021, the contents of which is incorporated herewith by reference. Accordingly, in some embodiments, the molar ratio of cationic lipid to non-cationic lipid to cholesterol (or cholesterol analogue) to PEG-modified lipid is between about 41-70: 9-18: 9-48: 2-6. A lipid nanoparticle with such a composition is advantageous because it is capable of being nebulized, e.g., at a nebulization output rate of greater than 12 ml/h or at a nebulization output rate of greater than 15 ml/h.

In some embodiments, the molar ratio of the cationic lipid in a lipid nanoparticle in accordance with the invention is 45%-70%. In some embodiments, the molar ratio of the cationic lipid is 45%-65%. In some embodiments, the molar ratio of the cationic lipid is 50%-70%. In some embodiments, the molar ratio of the cationic lipid is 50%-65%. In particular embodiments, the molar ratio of the cationic lipid is 50%-60%. In one specific embodiment, the molar ratio of the cationic lipid is about 50%. In another specific embodiment, the molar ratio of the cationic lipid is about 55%. In yet a further specific embodiment, the molar ratio of the cationic lipid is about 60%.

In some embodiments, the molar ratio of the non-cationic lipid in a lipid nanoparticle in accordance with the invention is 9%-15%. In particular embodiments, the molar ratio of the non-cationic lipid is 10%-15%. In a specific embodiment, the molar ratio of the non-cationic lipid is about 15%. In another specific embodiment, the molar ratio of the non-cationic lipid is about 12.5%. In yet a further specific embodiment, the molar ratio of the non-cationic lipid is about 10%.

In some embodiments, the molar ratio of the PEG-modified lipid in a lipid nanoparticle in accordance with the invention is 3%-6%. In particular embodiments, the molar ratio of the PEG-modified lipid is 4%-6%. In a specific embodiment, the molar ratio of the PEG-modified lipid is about 5%. In another specific embodiment, the molar ratio of the PEG-modified lipid is about 3%.

In some embodiments, the molar ratio of the cholesterol or cholesterol analogue in a lipid nanoparticle in accordance with the invention is 10%-45%. In particular embodiments, the molar ratio of the cholesterol or cholesterol analogue is 10%-30%. In one particular embodiment, the molar ratio of the cholesterol or cholesterol analogue is 25%-30%. In a specific embodiment, the molar ratio of the cholesterol or cholesterol analogue is about 25%. In another specific embodiment, the molar ratio of the cholesterol or cholesterol analogue is about 30%.

In one specific embodiment, the molar ratios of the lipids in a lipid nanoparticle in accordance with the invention are: a. 50%-60% cationic lipid, b. 9%-18% non-cationic lipid, c. 4%-6% PEG-modified lipid, and d. 20-35% cholesterol or cholesterol analogue. In another specific embodiment, the molar ratios of the lipids in a lipid nanoparticle in accordance with the invention are: a. 50%-60% cationic lipid, b. 9%-15% non-cationic lipid, c. 4%-6% PEG-modified lipid, and d. 25-30% cholesterol or cholesterol analogue.

In exemplary embodiments, the molar ratios of the lipids in a lipid nanoparticle in accordance with the invention are:

1) a. about 50% cationic lipid, b. about 15% non-cationic lipid, c. about 5% PEG-modified lipid, and d. about 30% cholesterol or cholesterol analogue.
2) a. about 60% cationic lipid, b. about 10% non-cationic lipid, c. about 5% PEG-modified lipid, and d. about 25% cholesterol or cholesterol analogue.
3) a. about 50% cationic lipid, b. about 10% non-cationic lipid, c. about 5% PEG-modified lipid, and d. about 35% cholesterol or cholesterol analogue.
4) a. about 50% cationic lipid, b. about 12.5% non-cationic lipid, c. about 5% PEG-modified lipid, and d. about 32.5% cholesterol or cholesterol analogue.
5) a. about 50% cationic lipid, b. about 17.5% non-cationic lipid, c. about 5% PEG-modified lipid, and d. about 27.5% cholesterol or cholesterol analogue.
6) a. about 55% cationic lipid, b. about 10% non-cationic lipid, c. about 5% PEG-modified lipid, and d. about 30% cholesterol or cholesterol analogue.
7) a. about 55% cationic lipid, b. about 12.5% non-cationic lipid, c. about 5% PEG-modified lipid, and d. about 27.5% cholesterol or cholesterol analogue. In some embodiments, the molar ratios of the lipids are: a. about 55% cationic lipid, b. about 15% non-cationic lipid, c. about 5% PEG-modified lipid, and d. about 25% cholesterol or cholesterol analogue.
8) a. about 55% cationic lipid, b. about 17.5% non-cationic lipid, c. about 5% PEG-modified lipid, and d. about 22.5% cholesterol or cholesterol analogue.
9) a. about 60% cationic lipid, b. about 12.5% non-cationic lipid, c. about 5% PEG-modified lipid, and d. about 22.5% cholesterol or cholesterol analogue.
10) a. about 60% cationic lipid, b. about 15% non-cationic lipid, c. about 5% PEG-modified lipid, and d. about 20% cholesterol or cholesterol analogue.

Methods of Producing Lipid Nanoparticles

Various processes can be used to prepare an mRNA-encapsulating lipid nanoparticle. Typically, the first step in preparing such a suspension is to provide a lipid solution. The lipid solution contains a mixture of the lipids that form the lipid nanoparticle. The lipid solution can be mixed with an mRNA solution, without first pre-forming the lipids into lipid nanoparticles, for encapsulation of mRNA (as described in U.S. patent application Ser. No. 14/790,562 entitled "Encapsulation of messenger RNA", filed Jul. 2, 2015 and its provisional U.S. patent application Ser. No. 62/020,163, filed Jul. 2, 2014, and in International Patent Application WO 2016/004318, and in US 2016/0038432, both of which are hereby incorporated by reference in its entirety). Alternatively, a lipid solution is used to prepare lipid nanoparticles. The preformed lipid nanoparticles can then be mixed with an mRNA solution to encapsulate the mRNA in the preformed lipid nanoparticles, e.g., as described in International Patent Application WO 2018/089801, and in US 2018/0153822, both of which are hereby incorporated by reference in its entirety. These exemplary processes result in the effective encapsulation of mRNA in lipid nanoparticles. Typically, the processes can be optimized to achieve an encapsulation efficiency of at least about 90%, e.g., at least about 95%, at least about 96%, at least about 97%, at least about 98%, or at least about 99%.

As used herein, the term "encapsulation," or grammatical equivalent, refers to the process of confining an mRNA molecule within a lipid nanoparticle. As used herein, this typically means that all, or substantially all, of the mRNA is encapsulated in the lipid nanoparticle.

The inventors have discovered that the encapsulation efficiency of the lipid nanoparticles in the compositions of the invention remain relatively unaffected by nebulization, e.g. when a lipid nanoparticle in the compositions of the invention is aerosolized by means of a vibrating mesh nebulizer. Accordingly, in some embodiments, the lipid nanoparticle has an encapsulation efficiency before and after nebulization of at least about 90%. In some embodiments, the lipid nanoparticle has an encapsulation efficiency before and after nebulization of at least about 95%. In some embodiments, the lipid nanoparticle has an encapsulation efficiency before and after nebulization of at least about 96%. In some embodiments, the lipid nanoparticle has an encapsulation efficiency before and after nebulization of at least about 97%. In some embodiments, the lipid nanoparticle has an encapsulation efficiency before and after nebulization of at least about 98%. In some embodiments, the lipid nanoparticle has an encapsulation efficiency before and after nebulization of at least about 99%.

The skilled artisan will appreciate that small loss in encapsulation efficiency upon nebulization of a lipid nanoparticle in the compositions of the invention is acceptable, as long as the majority of the lipid nanoparticles (e.g., at least 80% of the lipid nanoparticles) in a composition of the invention effectively encapsulate the mRNA after they have been nebulized. Accordingly, in some embodiments, the encapsulation efficiency of the lipid nanoparticle changes less than about 20% upon nebulization. In particular embodiments, the encapsulation efficiency of the lipid nanoparticle changes less than about 15% upon nebulization. In a specific embodiment, the encapsulation efficiency of the lipid nanoparticle changes less than about 10% upon nebulization. For example, in some embodiments, the encapsulation efficiency of the lipid nanoparticle after nebulization is no more than about 20% lower than the encapsulation efficiency of the lipid nanoparticle before nebulization. In particular embodiments, the encapsulation efficiency of the lipid nanoparticle after nebulization is no more than about 15% lower than the encapsulation efficiency of the lipid nanoparticle before nebulization. In a specific embodiment, the encapsulation efficiency of the lipid nanoparticle after nebulization is no more than about 10% lower than the encapsulation efficiency of the lipid nanoparticle before nebulization. It is particularly desirable that the encapsulation efficiency of the lipid nanoparticle after nebulization is about the same as the encapsulation efficiency of the lipid nanoparticle before nebulization.

Lipid Nanoparticle Size

The processes for preparing a lipid nanoparticle in the compositions of the invention referred to above yield compositions with a well-defined particle size. In some embodiments, the lipid nanoparticle has a size less than about 150 nm (e.g., pre-nebulization). In specific embodiments, the lipid nanoparticle has a size less than about 100 nm (e.g., pre-nebulization). In particular embodiments, the lipid nanoparticle has a size (e.g., pre-nebulization) of 50-150 nm, e.g. 50-125 nm, 50-100 nm or 60-80 nm. In specific embodiments, the lipid nanoparticle has a pre-nebulization size of 50-100 nm. The inventors have found that a lipid nanoparticle in this size range can maintain a post-nebulization size of 50-150 nm, e.g., 50-125 nm (see WO 2012/170889). Lipid nanoparticles within these size ranges have been used successfully to delivery mRNA to the lungs of a subject via nebulization.

In some embodiments, the lipid nanoparticle has a size (e.g., pre-nebulization) of less than about 200 nm. In some embodiments, the lipid nanoparticle has a size (e.g., pre-nebulization) of less than about 150 nm. In some embodiments, the lipid nanoparticle has a size (e.g., pre-nebulization) of less than about 120 nm. In some embodiments, the lipid nanoparticle has a size (e.g., pre-nebulization) of less than about 110 nm. In some embodiments, the lipid nanoparticle has a size (e.g., pre-nebulization) of less than about 100 nm. In some embodiments, the lipid nanoparticle has a size (e.g., pre-nebulization) of less than about 80 nm. In some embodiments, the lipid nanoparticle has a size (e.g., pre-nebulization) of less than about 60 nm.

The size of a lipid nanoparticle may be determined by quasi-electric light scattering (QELS) as described in Bloomfield, Ann. Rev. Biophys. Bioeng., 10:421-150 (1981), incorporated herein by reference. For example, a Malvern Zetasizer can be used to measure the particle size in a lipid nanoparticle.

Lyophilization

In some embodiments, a composition of the invention is provided in lyophilized form and reconstituted in an aqueous solution prior to nebulization. The applicant hereby fully incorporates by reference their earlier patent application WO 2012/170889 filed on Jun. 8, 2012. The lyophilized compositions are suitable for long term storage. They can be reconstituted with purified water for administration to a subject in need thereof. In certain embodiments, upon reconstitution with an appropriate rehydration medium (e.g., purified water, deionized water, 5% dextrose (w/v), 10% trehalose (w/v) or normal saline), the reconstituted composition demonstrates pharmacological or biological activity comparable with that observed prior to lyophilization. For example, in certain embodiments, the pharmacological and biological activity of an encapsulated mRNA is equivalent to that observed prior to lyophilization of the composition; or alternatively demonstrates a negligible reduction in pharmacological and biological activity (e.g., less than about a 1%, 2%, 2.5%, 3%, 4%, 5%, 6%, 7%, 8% 9% or 10% reduction in the biological or pharmacological activity of an encapsulated polynucleotide).

In certain embodiments, the lyophilized lipid nanoparticles are characterized as being stable (e.g., as stable as an equivalent unlyophilized lipid nanoparticle). Lyophilization of the lipid nanoparticles does not appreciably change or alter the particle size of the lipid nanoparticles following lyophilizaiton and/or reconstitution. For example, disclosed herein are compositions comprising lyophilized lipid nanoparticles, wherein upon reconstitution (e.g., with purified water) the lipid nanoparticles do not flocculate or aggregate, or alternatively demonstrated limited or negligible flocculation or aggregation (e.g., as determined by the particle size of the reconstituted lipid nanoparticles).

Accordingly, in certain embodiments, upon reconstitution of a lyophilized lipid nanoparticle, the lipid nanoparticles have a Dv50 of less than about 100 nm (e.g., less than about 90 nm, 80 nm, 70 nm, 60 nm, 50 nm, 40 nm or smaller). In a specific embodiment, upon reconstitution of a lyophilized lipid nanoparticle the lipid nanoparticles have a Dv50 of between 90 nm and 50 nm. Similarly, in certain embodiments, upon reconstitution of a lyophilized lipid nanoparticle the lipid nanoparticles have a Dv90 of less than about 400 nm (e.g., less than about 300 nm, 200 nm, 150 nm, 125 nm, 100 nm, 75 nm, 50 nm, 25 nm, or smaller). In a specific embodiment, upon reconstitution of a lyophilized lipid nanoparticle, the lipid nanoparticles have a Dv90 of between 300 nm and 100 nm.

In other embodiments, compositions comprising lyophilized lipid nanoparticles are characterized as having a polydispersion index of less than about 1 (e.g., less than 0.95, 0.9, 0.8, 0.75, 0.7, 0.6, 0.5, 0.4, 0.3, 0.25, 0.2, 0.1, 0.05, or less). In some embodiments, compositions comprising lyophilized lipid nanoparticles demonstrate a reduced tendency to flocculate or otherwise aggregate (e.g., during lyophilization or upon reconstitution). For example, upon reconstitution the lipid nanoparticles (e.g., pre-nebulization) may have an average particle size (Zave) of less than 200 nm, (e.g., less than about 175 nm, 150 nm, 125 nm, 100 nm, 75 nm, or smaller in a PBS solution). Typically, the average particle size (Zave) of lipid nanoparticles for use with the invention is between 60 nm and 100 nm. In a specific embodiment, the average particle size (Zave) of lipid nanoparticles for use with the invention is between 50 nm and 100 nm.

In some embodiments, the lyophilized lyophilized lipid nanoparticles further comprise or are alternatively prepared using one or more lyoprotectants (e.g., sugars and/or carbohydrates). In certain embodiments, the inclusion of one or more lyoprotectants in the lipid nanoparticle may improve or otherwise enhance the stability of the lyophilized lipid nanoparticles (e.g., under normal storage conditions) and/or facilitate reconstitution of the lyophilized lipid nanoparticles using a rehydration media, thereby preparing an aqueous formulation. For example, in certain embodiments the lipid nanoparticles are prepared and prior to lyophilization the buffer present in the liposomal formulation may be replaced (e.g., via centrifugation) with a lyoprotectant such as a sucrose solution or suspension (e.g., an aqueous solution comprising between about 1-50% (w/v) or 10-25% (w/v) sucrose). In some embodiments, the lyoprotectant in trehalose. In some embodiments, the lyoprotectant comprises 10-50% (w/v), or 10-25% (w/v) or 10-20% (w/v) or 10-15% (w/v) trehalose. Other lyoprotectants that may be used to prepare the lyophilized compositions described herein include, for example, dextran (e.g., 1.5 kDa, 5 kDa and/or 40 kDa) and inulin (e.g., 1.8 kDa and/or 4 kDa). The lyophilized lipid nanoparticles have an encapsulation efficiency of greater than about 80%.

A composition comprising a lyophilized lipid nanoparticle is stable at 4 °C for at least 1 month, at least 2 months, at least 3 months, at least 4 months, at least 5 months, at least 6 months, or for at least 1 year. In some embodiments, the lyophilized lipid nanoparticles may be stored under refrigeration and remain stable (e.g., as demonstrated by minimal or no losses in their intended pharmaceutical or biological activity) for extended periods of time (e.g., stable for at least about 1, 2, 3, 4, 5, 6, 9, 12, 18, 24, 36 months or longer upon storage at about 4 °C). In other embodiments, the lyophilized lipid nanoparticles may be stored without refrigeration and remain stable for extended periods of time (e.g., stable for at least about 1, 2, 3, 4, 5, 6, 9, 12, 18, 24, 36 months or longer upon storage at about 25 °C).

The composition in lyophilized form can be stored in frozen condition for 1, 2, 3, 4, 5 or 10 years without loss of pharmacological or biological activity.

Pulmonary Delivery

Compositions of the inventions are typically administered by pulmonary delivery. Accordingly, the invention also provides methods for delivering mRNA in vivo by administering a composition of the invention via pulmonary delivery to a subject. In some embodiments, pulmonary delivery is done via intranasal administration or inhalation. Intranasal administration may be achieved through the use of a device that generates a nasal spray. Nasal spray devices are well-known in the art.

Nebulization

In a typical embodiment, a composition of the invention is nebulized prior to inhalation. Nebulization results in an aerosolized composition which can be inhaled. Upon inhalation, the lipid nanoparticles are distributed throughout the nose, airways and the lungs and taken up by the epithelial cells of these tissues. As a consequence, the mRNA encapsulated in the lipid nanoparticles is delivered into the cells and expressed, e.g., in the nasal cavity, trachea, bronchi, bronchioles, and/or other pulmonary system-related cells or tissues. Additional teaching of pulmonary delivery and nebulization are described, e.g., in WO 2018/089790 and WO 2018/213476, each of which is incorporated by reference in its entirety.

Inhaled aerosol droplets of a particle size of less than 8 μm (e.g., 1-5 μm) can penetrate into the narrow branches of the lower airways. Aerosol droplets with a larger diameter are typically absorbed by the epithelial cells lining the oral cavity and upper airway, and are unlikely to reach the lower airway epithelium and the deep alveolar lung tissue. Accordingly, in particular in the context of pulmonary delivery to the lung epithelium, methods that comprise administering an mRNA encapsulated in lipid nanoparticles of the invention as an aerosol may include steps of generating droplets of a particle size of less than 8 μm (e.g., 1-5 μm), typically by nebulization of a composition of the invention, e.g. by using a nebulizer that is suitable for use with the compositions of the invention.

In a specific embodiment, a composition of the invention is nebulized to generate nebulized particles for inhalation by the subject. In particular embodiments, the lipid nanoparticle of the present invention is capable of being nebulized at a nebulization output rate of greater than about 12 ml/h. In particular embodiments, the lipid nanoparticle of the present invention is capable of being nebulized at a nebulization output rate of greater than about 15 ml/h. In other particular embodiments, the lipid nanoparticle of the present invention is capable of being nebulized at a nebulization output rate of greater than about 30 ml/h. In some embodiments, the lipid nanoparticle of the present invention is capable of being nebulized at a nebulization output rate of 12-50 ml/h. In some embodiments, the lipid nanoparticle of the present invention is capable of being nebulized at a nebulization output rate of 12-40 ml/h. In some embodiments, the lipid nanoparticle of the present invention is capable of being nebulized at a nebulization output rate of 15-50 ml/h. In some embodiments, the lipid nanoparticle of the present invention is capable of being nebulized at a nebulization output rate of 15-40 ml/h. In a typical embodiment, the lipid nanoparticle of the present invention is capable of being nebulized at a nebulization output rate of between 12 ml/h and about 30 ml/h, e.g., between 15 ml/h and about 30 ml/h. For example, a lipid nanoparticle of the present invention is capable of being nebulized with a nebulization output rate of about 12 ml/h or about 15 ml/h. In particular embodiments, a lipid nanoparticle of the present invention can be nebulized at a nebulization output rate of about 30 ml/h.

Typically, in the context of the present invention, a lipid nanoparticle that is capable of being nebulized at a higher nebulization output rate retains the capability of effectively encapsulating the mRNA after nebulization, such that the majority of the lipid nanoparticles (e.g., at least 80%, e.g., at least 85%, particularly at least 90% of the lipid nanoparticles) in a composition of the invention encapsulate mRNA after they have been nebulized. Accordingly, in some embodiments, the encapsulation efficiency of the lipid nanoparticle of the present invention changes less than about 20% upon nebulization. In particular embodiments, the encapsulation efficiency of the lipid nanoparticle of the present invention changes less than about 15% upon nebulization. In a specific embodiment, the encapsulation efficiency of the lipid nanoparticle of the present invention changes less than about 10% upon nebulization. For example, in some embodiments, the encapsulation efficiency of the lipid nanoparticle of the present invention after nebulization is no more than about 20% lower than the encapsulation efficiency of the lipid nanoparticle before nebulization. In particular embodiments, the encapsulation efficiency of the lipid nanoparticle of the present invention after nebulization is no more than about 15% lower than the encapsulation efficiency of the lipid nanoparticle before nebulization. In a specific embodiment, the encapsulation efficiency of the lipid nanoparticle of the present invention after nebulization is no more than about 10% lower than the encapsulation efficiency of the lipid nanoparticle before nebulization.

Nebulized particles for inhalation by a subject typically have an average size less than 8 μm. In some embodiments, the nebulized particles for inhalation by a subject have an average size between approximately 1-8 μm. In particular embodiments, the nebulized particles for inhalation by a subject have an average size between approximately 1-5 μm. In specific embodiments, the mean particle size of the nebulized composition of the invention is between about 4 μm and 6 μm, e.g., about 4 μm, about 4.5 μm, about 5 μm, about 5.5 μm, or about 6 μm.

Particle size in an aerosol is commonly described in reference to the Mass Median Aerodynamic Diameter (MMAD). MMAD, together with the geometric standard deviation (GSD), describes the particle size distribution of any aerosol statistically, based on the weight and size of the particles. Means of calculating the MMAD of an aerosol are well known in the art.

For example, the MMAD output of a nebulizer using a composition of the invention can be determined using a Next Generation Impactor. Another parameter to describe particle size in an aerosol is the Volume Median Diameter (VMD). VMD also describes the particle size distribution of an aerosol based on the volume of the particles. Means of calculating the VMD of an aerosol are well known in the art. A specific method used for determining the VMD is laser diffraction, which is used herein to measure the VMD of a composition of the invention (see, e.g., Clark, 1995, Int J Pharm. 115:69-78).

Accordingly, in some embodiments, nebulization in accordance with the invention is performed to generate a Fine Particle Fraction (FPF), which is defined as the proportion of particles in an aerosol which have an MMAD or a VMD smaller than a specified value. In one specific embodiment, the FPF of a nebulized composition of the invention with a particle size<5 μm is at least about 30%, more typically at least about 40%, e.g., at least about 50%, more typically at least about 60%. In another specific embodiment, nebulization is performed in such a manner that the mean respirable emitted dose (i.e., the percentage of FPF with a particle size<5 μm; e.g., as determined by next generation impactor with 15 L/min extraction) is at least about 30% of the emitted dose, e.g., at least about 31%, at least about 32%, at least about 33%, at least about 34%, or at least about 35% the emitted dose. In yet another specific embodiment, nebulization is performed in such a manner that the mean respirable delivered dose (i.e., the percentage of FPF with a particle size<5 μm; e.g., as determined by next generation impactor with 15 L/min extraction) is at least about 15% of the emitted dose, e.g. at least 16% or 16.5% of the emitted dose.

In some embodiments, nebulization is performed with a nebulizer. One type of nebulizer is a jet nebulizer, which comprises tubing connected to a compressor, which causes compressed air or oxygen to flow at a high velocity through a liquid medicine to turn it into an aerosol, which is then inhaled by the subject. Another type of nebulizer is the ultrasonic wave nebulizer, which comprises an electronic oscillator that generates a high frequency ultrasonic wave, which causes the mechanical vibration of a piezoelectric element, which is in contact with a liquid reservoir. The high frequency vibration of the liquid is sufficient to produce a vapor mist. Exemplary ultrasonic wave nebulizers are the Omron NE-U17 and the Beurer Nebulizer IH30. A third type of nebulizer comprises vibrating mesh technology (VMT). A VMT nebulizer typically comprises a mesh/membrane with 1000-7000 holes that vibrates at the top of a liquid reservoir and thereby pressures out a mist of very fine aerosol droplets through the holes in the mesh/membrane. Exemplary VMT nebulizers include: eFlow (PARI Medical Ltd.), i-Neb (Respironics Respiratory Drug Delivery Ltd), Nebulizer IH50 (Beurer Ltd.), AeroNeb Go (Aerogen Ltd.), InnoSpire Go (Respironics Respiratory Drug Delivery Ltd), Mesh Nebulizer (Shenzhen Homed Medical Device Co, Ltd.), Portable Nebulizer (Microbase Technology Corporation) and Airworks (Convexity Scientific LLC). In some embodiments, the mesh or membrane of the VMT nebulizer is made to vibrate by a piezoelectric element. In some embodiments, the mesh or membrane of the VMT nebulizer is made to vibrate by ultrasound.

VMT nebulizers have been found to be particularly suitable for practicing the invention because they do not affect the mRNA integrity of the mRNA encapsulated within lipid nanoparticles of the composition of the present invention. Typically, at least about 60%, e.g., at least about 65% or at least about 70%, of the mRNA in the compositions of the invention maintains its integrity after nebulization.

In some embodiments, nebulization is continuous during inhalation and exhalation. More typically, nebulization is breath-actuated. Suitable nebulizers for use with the invention have nebulization rate of greater than 0.2 mL/min. In some embodiments, the nebulization rate is >0.25 mL/min. In other embodiment, the nebulization rate is greater than 0.3 mL/min. In certain embodiments, the nebulization rate is greater than 0.45 mL/min. In a typical embodiment, the nebulization rate ranges between 0.2 mL/min and 0.5 mL/min. In some embodiments, the nebulization rate is at least 0.8 mL/min, is at least 0.16 mL/min or is at least 0.25 mL/min.

Therapeutic Use of Compositions

The invention provides methods of delivering mRNA in vivo comprising administering the compositions of the invention via pulmonary delivery to a subject. In some embodiments, the subject is human. In certain embodiments, the pulmonary delivery can be by intranasal administration or inhalation. In certain embodiments, the composition is nebulized prior to inhalation.

The encapsulated mRNA in compositions of the invention encodes a protein. In some embodiments, the mRNA is delivered to the lungs. In particular embodiments, the protein encoded by the mRNA is expressed in the lung. The protein can, for example, be a secreted protein, such as an antibody. In some embodiment, the protein can be a membrane protein, such as a viral surface antigen, a cell surface receptor, or a membrane channel (e.g., cystic fibrosis transmembrane conductance regulator (CFTR)). The protein expressed by the mRNA typically has therapeutic activity. For example, the expressed protein can be used to treat or prevent a disease or disorder. Accordingly, the lipid nanoparticles and compositions of the invention are for use in the treatment or prevention of a disease or disorder. Typically, such use comprises pulmonary administration of the lipid nanoparticles or compositions, e.g., via nebulization. In some embodiments, the lipid nanoparticles and compositions are for use in the manufacture of a medicament for the treatment or prevention of a disease or disorder. In a typical embodiment, such manufacture includes the formulation of the lipid nanoparticles in compositions, which are suitable for pulmonary administration, e.g., via nebulization. The invention also provides methods of treating or preventing a disease or disorder in a subject, the method comprising administering the composition of the invention via pulmonary delivery to the subject. In some embodiments, the pulmonary delivery is via nebulization.

The methods of the invention can be used to treat a variety of diseases and disorders in a subject. In some embodiments, the invention provides methods of treating or preventing a disease or a disorder in a subject, wherein the method comprises administering the compositions of the invention via pulmonary delivery to a subject.

In particular embodiments, the disease or disorder is a pulmonary disease or disorder, e.g., chronic respiratory diseases; protein deficiencies, e.g., protein deficiencies affecting the lungs; neoplastic diseases, e.g., tumours; and infectious disease. In particular embodiments, the disease or disorder is a protein deficiency. In some embodiments, the subject is healthy, in which case treatment is for the prevention of a disease or disorder (e.g., by immunisation with an mRNA-encoded antigen to prevent an infectious disease). In other embodiments, the subject is suffering from a disease or disorder, in which case the treatment may be aimed at reducing or ameliorating one or more symptoms of the disease or disorder, and/or at addressing the underlying cause of the disease, e.g., by providing a deficient protein through delivery of an mRNA encoding the same, or by supplying an agent that targets the diseased tissue, such as an antibody that interferes with tumour growth. In some embodiments, the invention provides methods of treating comprising administering the compositions of the invention via pulmonary delivery to a subject.

Expression of the mRNA in the lungs may partially or totally restore the level of the protein in the subject. For example, the methods of the invention result in a subject having protein levels that are comparable to a healthy subject. In certain embodiments, the methods of the invention result in a 20%, 30%, 40%, 50%, 60%, 70%, 80%, 90% or 100% in production of the protein.

In some embodiments, the invention provides methods of treating cystic fibrosis in a subject, the method comprising administering the compositions of the invention via pulmonary delivery to the subject. In some embodiments, the mRNA encodes CFTR. In some embodiments, the invention provides methods of treating primary ciliary dyskinesia in a subject, the method comprising administering the compositions of the invention via pulmonary delivery to the subject. In some embodiments, the mRNA encodes DNAI1. In some embodiments, the invention provides methods of treating a surfactant deficiency in a subject, the method comprising administering the compositions of the invention via pulmonary delivery to the subject. In some embodiments, the mRNA encodes a surfactant protein.

In some embodiments, the invention provides methods of treating a chronic respiratory disease in a subject, the method comprising administering the compositions of the invention via pulmonary delivery to the subject. Examples of chronic respiratory diseases that can be treated with the methods of the invention include chronic obstructive pulmonary disease (COPD), asthma, pulmonary arterial hypertension or idiopathic pulmonary fibrosis. In some embodiments, the mRNA encodes a protein for treating a symptom of a pulmonary disease or disorder. In certain embodiments, the mRNA encodes an antibody directed against a pro-inflammatory cytokine.

In some embodiments, the invention provides methods of treating or preventing a neoplastic disease, e.g., a tumour, in a subject, the method comprising administering the compositions of the invention via pulmonary delivery to the subject. In some embodiments, the tumour is a lung tumour or lung cancer, for example non-small cell lung cancer or small cell lung cancer. In certain embodiments, the mRNA encodes an antibody that targeting a protein expressed on the surface of cells making up the tumour. In other embodiments, the mRNA encodes an antigen derived from the tumour, e.g., a tumour neoantigen.

In some embodiments, the invention provides methods of treating an infectious disease in a subject, the method comprising administering the compositions of the invention via pulmonary delivery to the subject. In some embodiments, the infectious disease is caused by a virus. In some embodiments, the infectious disease is a pulmonary infectious disease or disorder. In some embodiments the mRNA encodes a soluble decoy receptor that binds a surface protein of the virus. In some embodiments the mRNA encodes an antibody directed to a surface protein of the virus. In some embodiments, the infectious disease is caused by a bacterium. In particular embodiments, the mRNA encodes an antibody directed to a surface protein of the bacterium. In some embodiments, the mRNA encodes an antigen derived from a causative agent of the infections disease (e.g., a surface protein derived from a virus or a bacterium which causes the infectious disease). For example, a lipid nanoparticle of the invention encapsulating an mRNA encoding the antigen, or a composition comprising the lipid nanoparticle may be used to immunize a subject to prevent the infectious disease in the subject.

EXAMPLES

While certain compositions and methods of the present invention have been described with specificity in accordance with certain embodiments, the following examples serve only to illustrate them and are not intended to limit them.

Example 1. Formulation of mRNA Lipid Nanoparticle

An mRNA encoding either firefly luciferase (FFL), mCherry, cystic fibrosis transmembrane conductance regulator (CFTR) or dynein axonemal intermediate chain 1 (DNAI1) protein were synthesized by in vitro transcription from a plasmid DNA template, which was followed by the addition of a 5' cap structure (Cap 1) and a 3' poly(A) tail. The mRNA encoding the protein also comprised 5' and 3' untranslated regions (UTRs). The final mRNA construct had a 3' poly(A) tail of approximately 400 to 700 nucleotides in length, as determined by gel electrophoresis.

To prepare lipid nanoparticles for encapsulation of the mRNA, four lipid components were dissolved in ethanol to provide an ethanol-based lipid solution. The first component was an ionizable cationic lipid (either SY-3-E14-DMAPr or TL1-01D-DMA). This component is positively charged at low pH which facilitates efficient encapsulation of the negatively charged mRNA. It may also play a key role in cell surface interaction to allow for cellular uptake. The second component was 1,2-dioleoyl-sn-glycero-3-phosphoethanolamine (DOPE). DOPE is a zwitterionic lipid that has been reported to have fusogenic properties. The third component was 1,2-dimyristoyl-sn-glycerol, methoxypolyethylene glycol (DMG-PEG-2K), a PEGylated/PEG-modified lipid. The addition of this PEGylated lipid provides control over particle size and stability of the resulting lipid nanoparticle and may provide enhanced mucopentrating properties for lung uptake. The fourth component was cholesterol. An aqueous-based solution comprising either the FFL, mCherry, CFTR or DNAI1-encoding mRNA in a citrate buffer was combined with the ethanol-based lipid solution to form lipid nanoparticles encapsulating the mRNA.

Example 2. Nebulization of Lipid Nanoparticles

To identify mRNA-lipid nanoparticle formulations that can be efficiently nebulized while retaining characteristics important for in vivo delivery and expression of the encapsulated mRNA, combinations of various excipients were tested in over 300 different conditions. The excipients tested included 10 different buffers, 5 different salts, two different sugars, various viscosity regulators, and 10 different surfactants/solubilizers. Test conditions included varying buffers strengths and pH ranges; varying salt concentrations; varying sugar concentrations; and varying surfactant concentrations. The test formulations were nebulized using a vibrating mesh nebulizer (Aerogen Solo). The following parameters were analyzed to determine whether a formulation was useful for nebulizing the mRNA-lipid nanoparticle compositions:

Mass median aerodynamic diameter (MMAD), which indicates the average aerosol particle size. A MMAD of 1-5 μm is desirable.

Polydispersity index (PDI). A PDI of less than 0.25 is desirable.

Nebulization output rate. A rate of 12-15 ml/h is desirable.

Nebulization dose. A higher dose of mRNA is desirable.

Size of the lipid nanoparticle post-nebulization. A particle size of less than 150 nm is desirable.

Loss in post-nebulization encapsulation efficiency (EE %). A loss of no greater than 20% is desirable.

Test surfactants/solubilizers included various PEGs such as 0.1-5% w/v PEG 400. Their presence was found to have no appreciable effect on the above nebulization parameters. Surprisingly. TPGS, a surfactant consisting of an antioxidant moiety covalently linked via a linker moiety to a PEG moiety was identified as being suitable to maintain the lipid nanoparticle size before and after nebulization (see Example 3). Combining such a surfactant with a sugar, buffer and/or salt may, under certain conditions, further improve nebulization (see Examples 5-8).

Example 3. Improved Nebulization of mRNAA-Lipid Nanoparticle Compositions Comprising TPGS

Introduction

This examples illustrates that the presence of TPGS as an excipient in compositions comprising mRNA encapsulated in a lipid nanoparticle increases nebulization output rates.

Materials and Methods mRNA was encapsulated in lipid nanoparticles as described in Example 1. The lipid nanoparticle compositions and the compositions that were nebulized are summarized in Table 1. The compositions were nebulized as described in Example 2.

TABLE 1

The components of the lipid nanoparticles and the nebulization compositions.

| Groups | Lipid nanoparticle | Nebulization composition |
|---|---|---|
| Control | 5% DMG-PEG2K, 40% SY-3-E14-DMAPr, 25% cholesterol and 30% DOPE | 6% trehalose |
| S1 | | 6% trehalose, 0.2% TPGS (w/v) |
| S2 | | |
| Control | 3% DMG-PEG2K, 40% TL1-01D-DMA, 25% cholesterol and 32% DOPE | 4% trehalose |
| S3 | | 4% trehalose, 0.2% TPGS |

Results

Figure 2A:
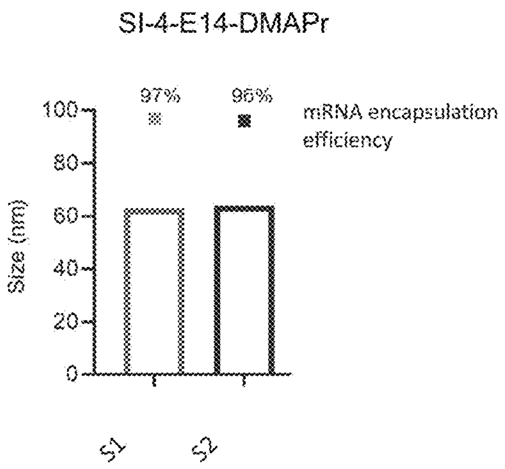
FIG. 2A and FIG. 2B demonstrate the pre-nebulization characteristics of lipid nanoparticles that contain the cationic lipids SI-4-E14-DMAPR and TL1-01D-DMA, respectively.
Figure 2B:
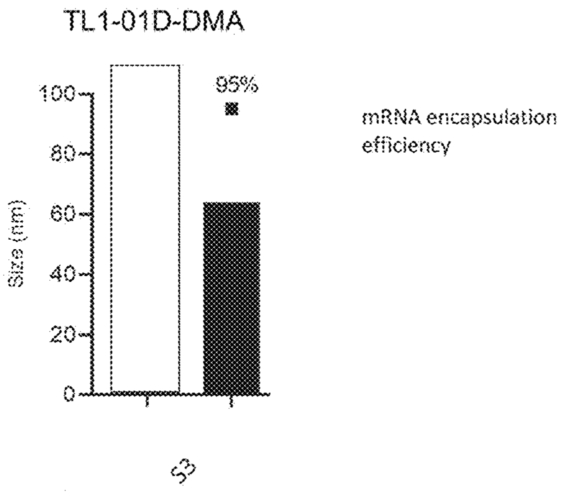

As shown in FIG. 2A and FIG. 2B, the lipid nanoparticles that comprised either SY-3-E14-DMAPr or TL1-01D-DMA had a pre-nebulization size of approximately 60 nm, an mRNA encapsulation efficiency of over 95%.

Table 2 demonstrates that the presence of 0.2% (w/v) TPGS in the test compositions resulted in 80%-140% improvement of the nebulization output rate compared to the respective control compositions. This effect was independent of the composition of the lipid nanoparticle.

The presence of 0.2% (w/v) TPGS in the compositions resulted in a smaller difference in lipid nanoparticles size between pre- and post-nebulization compared to the control.

The addition of 0.2% (w/v) TPGS to the composition also resulted in improved doses of mRNA, which is desirable in mRNA therapy.

TABLE 2

| Nebulization rates and post-nebulization characteristics of the lipid nanoparticles. | | | | |
|---|---|---|---|---|
| Groups | Nebulization rates (ml/h) | Improvement in rate (%) | Nebulized dose (mg of mRNA/h) | Size (nm) |
| Control | 7.5 | — | 4.5 | 165 |
| S1 | 13.8 | 84 | 8.3 | 115 |
| S2 | 17.8 | 137 | 10.7 | 124 |
| Control | 7.1 | — | 2.8 | 180 |
| S3 | 16.2 | 128 | 6.5 | 104 |

In summary, these data demonstrate that compositions which comprise one or more surfactants consisting of an antioxidant moiety covalently linked via a linker moiety to a PEG moiety (such as TPGS) can increase nebulization output rates. This effect was independent of the composition of the lipid nanoparticle.

Example 4. Optimizing the TPGS Concentration

Introduction

This example illustrates that increasing the TPGS concentration to improve nebulization output rates can help in maintaining the pre-nebulization characteristics of the lipid nanoparticle after nebulization.

Materials and Methods mRNA was encapsulated in a lipid nanoparticle as described in Example 1. The lipid composition was 5% DMG-PEG2K, 40% SY-3-E14-DMAPr, 25% cholesterol and 30% DOPE. Compositions were prepared as shown in Table 3.

Results

Pre-nebulization the lipid nanoparticles had a size of 67 nm, a PDI of 0.194 and an EE % of 93. The post nebulization characteristics of the lipid nanoparticles are summarized in Table 3. These data demonstrate that as the concentration of TPGS in the composition is increased the difference in size of the lipid nanoparticle between pre- and post-nebulization is reduced.

TABLE 3

| The effect of different percentages of TPGS on post nebulization characteristics | |
|---|---|
| Nebulization composition | |
| 6% trehalose (control) | 164.3 |
| 6% trehalose, 1% TPGS (w/v) | 77.81 |
| 6% trehalose, 0.5% TPGS (w/v) | 93.72 |
| 6% trehalose, 0.1% TPGS (w/v) | 126.5 |

Figure 3B:
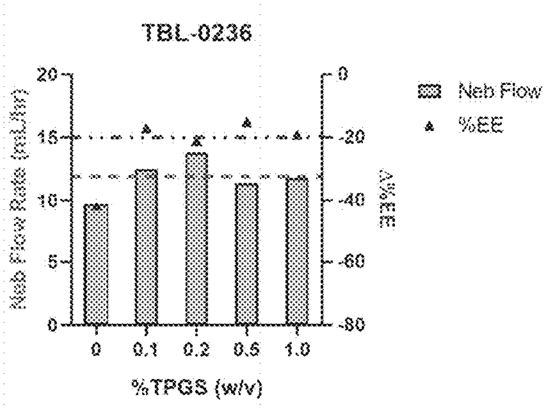

An additional composition was tested which contained 6% trehalose and 0.2% TPGS (w/v). FIG. 3A demonstrates that all four of the TPGS concentrations tested the difference in size of the lipid nanoparticle between pre- and post-nebulization was smaller compared to the control (without TPGS). FIG. 3B shows that compositions that comprised 0.1-1% TPGS (w/v) were able to increase nebulization flow rates and reduce the difference in post-nebulization encapsulation efficiency compared to the control. The composition that comprised 0.2% TPGS (w/v) produced the highest nebulization flow rate. All TPGS concentrations tested had a change in encapsulation efficiency (EE %) after nebulization of approximately 20%, which is desirable.

It was expected that for compositions to achieve high nebulization rates they would need to have a lower viscosity and reduced surface tension, for example compared to a composition that comprises saline. These properties were thought to be required in order to more easily aerosolize the composition. The presence of TPGS in the composition did not alter the viscosity and led only to a small drop in surface tension (e.g., from 65 mN/m to 58 mN/m), but its presence was still able to improve nebulization rates. It was therefore surprising that compositions which comprise one or more surfactants consisting of an antioxidant moiety covalently linked via a linker moiety to a PEG moiety (such as TPGS) were able to increase nebulization output rates.

In summary, these data demonstrate that compositions which comprise one or more surfactants consisting of an antioxidant moiety covalently linked via a linker moiety to a PEG moiety (such as TPGS) can increase nebulization output rates, while maintaining important pre-nebulization characteristics of the lipid nanoparticle, in particular encapsulation efficiency and size, at concentrations ranging from about 0.2% to about 1% w/v.

Example 5. Optimizing the Sugar and TPGS Concentrations

Introduction

This example illustrates the effect of altering the sugar concentration in compositions which comprise TPGS on nebulization rates and the post-nebulization characteristics of the lipid nanoparticles in these compositions.

Materials and Methods mRNA was encapsulated in a lipid nanoparticle as described in Example 1. The lipid composition was 5% DMG-PEG2K, 40% SY-3-E14-DMAPr, 25% cholesterol and 30% DOPE. Compositions to be nebulized were prepared as shown in Table 4.

TABLE 4

| Nebulization compositions tested | |
|---|---|
| Group | Nebulization composition |
| B1 | 6% trehalose, 0.2% TPGS |
| B2 | 6% trehalose, 0.3% TPGS |
| B3 | 6% trehalose, 0.5% TPGS |
| B4 | 8% trehalose, 0.2% TPGS |
| B5 | 8% trehalose, 0.3% TPGS |
| B6 | 8% trehalose, 0.5% TPGS |
| B7 | 10% trehalose, 0.2% TPGS |
| B8 | 10% trehalose, 0.3% TPGS |
| B9 | 10% trehalose, 0.5% TPGS |

Results

When the composition contained a higher concentrations of trehalose (8-10% w/v), a higher concentration of TPGS was required to maintain a high nebulization flow rate (FIG.

Figure 4A:
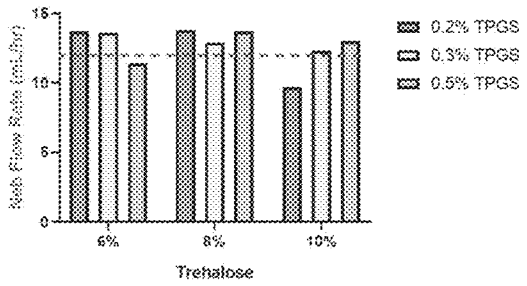
FIG. 4A and FIG. 4B demonstrate the effect of TPGS concentration and sugar concentration on nebulization flow rate and encapsulation efficiency (EE %), respectively.
Figure 4B:
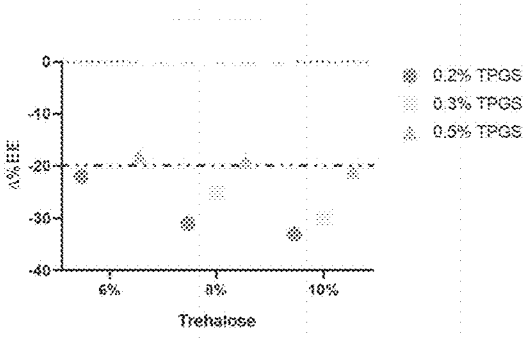

4A) and to minimize a drop in encapsulation efficiency post-nebulization (FIG. 4B). Based on these data, a particularly suitable composition amongst the test compositions was B6 which comprised 8% (w/v) trehalose and 0.5% (w/v) TPGS. As shown in Table 5 below, B6 had desirable characteristics including a high nebulization rate, a MMAD of between 1-5 μm, a post-nebulization change in encapsulation efficiency (EE %) of less than 20%, a lipid nanoparticle size of less than 150 nm and a low change in mRNA integrity.

TABLE 5

| Post-nebulization characteristics | |
|---|---|
| Nebulization rate (ml/h) | 13 |
| MMAD | 4.1 |
| Change in EE% | 18% |
| Size (nm) | 102 |
| PDI | 0.34 |
| Change in mRNA integrity | <5% |

In summary, if the sugar concentration in the composition is increased this alters the ability of a surfactant, which consists of an antioxidant moiety covalently linked via a linker moiety to a PEG moiety, to improve nebulization rates. If higher concentrations of sugar are used in the composition, then a higher concentration of surfactant is required to retain the positive nebulization effects.

Example 6. Improved Nebulization with Low Sugar Concentrations

Introduction

This example illustrates that lowering the sugar concentration can improve the nebulization output rates of mRNA-lipid nanoparticle compositions.

Materials and Methods mRNA was encapsulated in lipid nanoparticles as described in Example 1. The components of the lipid nanoparticles are described in Table 6. Table 6 also summarizes the components in the compositions tested, which were nebulized with an Aerogen Solo-vibrating mesh nebulizer.

TABLE 6

The effect of sugar concentration on post nebulization characteristics

| Lipid nanoparticle composition | Nebulization composition | Nebulization rate (ml/h) |
|---|---|---|
| 5% DMG-PEG2K, 60% HGT4002 and 35% DOPE | 10% Trehalose | 16.2 |
| | 6% Trehalose | 21.7 |
| 3% DMG-PEG2K, 40% TL1-01D-DMA, 25% cholesterol and 32% DOPE | 10% Trehalose | 7.3 |
| | 4% Trehalose | 10.6 |

Table 6 demonstrate that lower concentrations of sugar in the composition (for example 4-6%) can increase nebulization rates. This ability to increase the nebulization rate is independent of the lipid nanoparticle in the composition.

Example 7. The Effect of a Salt and Buffer on Nebulization Rates

Introduction

This example illustrates that the presence of a salt can improve the nebulization output rates of mRNA-lipid nanoparticle compositions.

Materials and Methods mRNA was encapsulated in lipid nanoparticles as described in Example 1. The components of the lipid nanoparticles are described in Table 7, which also summarizes the components in the compositions.

TABLE 7

Lipid nanoparticles and compositions tested

| Group | Lipid nanoparticle composition | Composition |
|---|---|---|
| A1 | Reference standard | 10% Trehalose |
| A2 | 3% DMG-PEG2K, 40% TL1-01D-DMA, 25% cholesterol and 32% DOPE | 4% Trehalose + 75mM NaCl |
| A3 | 3% DMG-PEG2K, 40% TL1-01D-DMA, 25% cholesterol and 32% DOPE | 4% Trehalose + 10mM Phosphate buffer (pH 5.5), 150 mM NaCl |

Results

Table 8 demonstrate that compositions which comprise a salt (A2 and A3) have higher nebulization rates compared to a control composition that does not salt (A1). Furthermore, a higher concentration of salt results in a higher nebulization rate. For example, composition A3, which contained 150 mM of sodium chloride, respectively, had a higher nebulization rate compared to composition A2, which contained only 75 mM of salt. As demonstrated in Table 8 the presence of a buffer in the composition does not alter the ability of higher salt concentrations to increase nebulization rates.

TABLE 8

The effect of salt concentration on nebulization

| Group | Nebulization rate (ml/h) | LOR (g/min) | Delivered mRNA dose (mg/ml) | % TA nebulized |
|---|---|---|---|---|
| A1 | 12 | — | | — |
| A2 | 17.2 | 0.281 | 0.5 (87%) | 98 |
| A3 | 17.9 | 0.284 | 0.5 (88%) | 96 |

These data demonstrate that it is advantageous for mRNA-lipid nanoparticle compositions to contain a salt, and in particular higher concentrations of salt (e.g. at about 100 nM-200 nM), because this results in improved nebulization rates.

Example 8. The Effect of pH and Salt Concentration on Nebulization Output Rates

Introduction

This example illustrates the effect of pH on the nebulization output rates of mRNA-lipid nanoparticle compositions.

Materials and Methods mRNA was encapsulated in lipid nanoparticles as described in Example 1. The components of the lipid nanoparticles are described in Table 9, which also summarizes the components in the compositions.

TABLE 9

Compositions tested

| Group | Lipid nanoparticle composition | Composition |
|---|---|---|
| C1 | Reference standard | 10% Trehalose |
| C2 | 5% DMG-PEG2K, 40% SY-3-E14-DMAPr, 25% cholesterol and 30% DOPE | 6% Trehalose, 10 mM Phosphate buffer (pH 5.5), 50mM NaCl |
| C3 | 5% DMG-PEG2K, 40% SY-3-E14-DMAPr, 25% cholesterol and 30% DOPE | 6% Trehalose, 10 mM Phosphate buffer (pH 7), 50 mM NaCl |
| C4 | 3% DMG-PEG2K, 40% TL1-01D-DMA, 25% cholesterol and 32% DOPE | 4% Trehalose + 10 mM Phosphate buffer (pH 5.5), 150mM NaCl |
| C5 | 3% DMG-PEG2K, 40% TL1-01D-DMA, 25% cholesterol and 32% DOPE | 4% Trehalose + 1xPBS |

Results

Composition C2 contained a phosphate buffer at pH 5.5, while composition C3 contained a phosphate buffer at pH 7. Although these two compositions had similar nebulization output rates, composition C2 had a much higher post-nebulization encapsulation efficiency than composition C3 (Table 10). Further combining a low pH with a high salt concentration resulted in a higher nebulization rate and a higher post-nebulization encapsulation efficiency (composition C4).

TABLE 10

The effect of salt concentration on nebulization

| Group | Nebulization rate (ml/h) | EE % | % TA nebulized |
|---|---|---|---|
| C1 | 12 | | — |
| C2 | 10.7 | 75% | 95.9 |
| C3 | 12.2 | 47% | 98 |
| C4 | 17.9 | 88% | 96 |
| C5 | 15.1 | 43% | 96 |

These data demonstrate that mRNA-lipid nanoparticle compositions with a low pH, for example about pH 5.5, can have improved nebulization rates, in particular when combined with a high salt concentration (100 mM-200 mM).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

I claim:

1. A composition comprising
an mRNA encapsulated in a lipid nanoparticle, and
one or more surfactants consisting of an antioxidant moiety covalently linked via a linker moiety to a PEG moiety, wherein:
the antioxidant moiety covalently linked via the linker moiety to the PEG moiety is present in the composition at a concentration of at least 0.1% weight to volume (w/v); and
the antioxidant moiety covalently linked via the linker moiety to the PEG moiety is present in the composition as an excipient that is distinct from any component forming the lipid nanoparticle.

2. The composition according to claim 1, wherein the PEG moiety is unmodified PEG, methoxy-PEG (mPEG) or carboxylic acid-functionalized PEG (COOH-PEG).

3. The composition according to claim 1, wherein the PEG moiety has an average molecular weight between 1 kDa and 5 kDa.

4. The composition according to claim 1, wherein the linker moiety is succinate, oxalate, adipate, malonate, fumarate, malate, glutarate or maleate.

5. The composition according to claim 1, wherein the antioxidant moiety is a lipophilic vitamin.

6. The composition according to claim 5, wherein the lipophilic vitamin is selected from vitamin A, D, E or K.

7. The composition according to claim 1, wherein the antioxidant moiety covalently linked via the linker moiety to the PEG moiety is at least one of:
(i) D-α-tocopheryl polyethylene glycol 1000 succinate (TPGS),
(ii) mPEG-2K-succinate-vitamin E,
(iii) COOH-PEG-3.4 k-succinate-vitamin E,
(iv) mPEG-2K-succinate-vitamin D,
(v) mPEG-2K-succinate-vitamin D, or
(vi) COOH-PEG-3.4 k-succinate-vitamin D.

8. The composition according to claim 7, wherein the antioxidant moiety covalently linked via the linker moiety to the PEG moiety is TPGS.

9. The composition according to claim 1, wherein the antioxidant moiety covalently linked via the linker moiety to the PEG moiety is present at a concentration of at least 0.2% w/v.

10. The composition according to claim 1, wherein the antioxidant moiety covalently linked via the linker moiety to the PEG moiety is present at a concentration of 0.1-5% w/v.

11. The composition according to claim 1, wherein the composition further comprises a buffer.

12. The composition according to claim 11, wherein the buffer is a phosphate buffer, MES buffer, PIPES buffer, HePES buffer, maleate buffer or succinate buffer.

13. The composition according to claim 1, wherein the composition further comprises a salt.

14. The composition according to claim 13, wherein the salt is at a concentration of 50 mM-200 mM.

15. The composition according to claim 13, wherein the salt is at a concentration of at least 10 mM.

16. The composition according to claim 13, wherein the salt is sodium chloride.

17. The composition according to claim 1, wherein the composition further comprises a sugar.

18. The composition according to claim 17, wherein the sugar is a disaccharide.

19. The composition according to claim 18, wherein the disaccharide is sucrose or trehalose.

20. The composition according to claim 17, wherein the sugar is at a concentration of 1%-20% w/v.

21. The composition according to claim 1, wherein the lipid nanoparticle comprises one or more cationic lipids, one or more non-cationic lipids, and one or more PEG-modified lipids.

22. The composition according to claim 21, wherein the one or more cationic lipids comprise imidazole cholesterol ester, GL-TES-SA-DMP-E18-2, GL-TES-SA-DME-E18-2, TL1-01D-DMA, TL1-04D-DMA, SY-3-E14-DMAPr, SI-4-E14-DMAPr, SY-010, TL1-10D-DMA, HEP-E3-E10, HEP-E4-E10, or Guan-SS-Chol.

23. The composition according to claim 21, wherein the one or more non-cationic lipids comprise DOPE, DEPE, DPPC or DOPC.

24. The composition according to claim 21, wherein the one or more PEG-modified lipids comprise DMG-PEG2K.

25. The composition according to claim 21, wherein the lipid nanoparticle further comprises one or more cholesterol-based lipids.

26. The composition according to claim 1, wherein the lipid nanoparticle has a size less than about 100 nm.

27. A method for delivering RNA-mRNA in vivo comprising administering the composition according to claim 1 via pulmonary delivery to a subject.

28. The method according to claim 27, wherein the pulmonary delivery is intranasal administration or inhalation.

29. The method according to claim 28, wherein the composition is nebulised prior to inhalation.

30. The method according to claim 29, wherein the composition is provided in lyophilized form and reconstituted in an aqueous solution prior to nebulization.

31. A method of treating a pulmonary disease or disorder in a subject, the method comprising administering the composition according to claim 1 via pulmonary delivery to the subject.

32. The method according to claim 31, wherein the pulmonary delivery is via nebulization.

33. The method according to claim 27, wherein the mRNA encodes a protein deficient in the subject.

34. The method according to claim 27, wherein the mRNA encodes CFTR or DNAI1.

35. The composition according to claim 17, wherein the sugar is trehalose.

36. The composition according to claim 35, wherein trehalose is at a concentration of 2-10% w/v.

37. The composition according to claim 21, wherein the one or more cationic lipids comprise GL-TES-SA-DMP-E18-2, GL-TES-SA-DME-E18-2, TL1-01D-DMA, TL1-04D-DMA, SY-3-E14-DMAPr, SI-4-E14-DMAPr, SY-010, TL1-10D-DMA, HEP-E3-E10, or HEP-E4-E10.

38. The composition according to claim 37, wherein the one or more cationic lipids comprise TL1-01D-DMA or SY-3-E14-DMAPr.

* * * * *